US012599515B2

(12) United States Patent
Motsch et al.

(10) Patent No.: US 12,599,515 B2
(45) Date of Patent: Apr. 14, 2026

(54) RECYCLABLE ABSORBENT ARTICLE PACKAGES

(71) Applicant: The Procter & Gamble Company, Cincinnati, OH (US)

(72) Inventors: Andreas Peter Motsch, Taunus (DE); Jonathan Hodgetts, Taunus (DE); Jürgen Hügel, Liederbach Deutschland (DE); Paul Thomas Weisman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 18/419,616

(22) Filed: Jan. 23, 2024

(65) Prior Publication Data

US 2024/0245561 A1     Jul. 25, 2024

Related U.S. Application Data

(60) Provisional application No. 63/514,817, filed on Jul. 21, 2023, provisional application No. 63/441,001, filed on Jan. 25, 2023.

(51) Int. Cl.
A61F 13/551 (2006.01)
B65D 65/38 (2006.01)
(Continued)

(52) U.S. Cl.
CPC .... A61F 13/5511 (2013.01); A61F 13/55115 (2013.01); B65D 65/38 (2013.01);
(Continued)

(58) Field of Classification Search
CPC ........ B65D 75/28; B65D 65/38; B65D 75/20; B65D 85/62; A61F 13/551;
(Continued)

(56) References Cited

U.S. PATENT DOCUMENTS

| | | | |
|---|---|---|---|
| 2,146,308 A | 2/1939 | Maxfield | |
| 2,290,564 A | 7/1942 | Krueger | |

(Continued)

FOREIGN PATENT DOCUMENTS

| | | |
|---|---|---|
| EP | 0439209 A1 | 7/1991 |
| EP | 0450114 A1 | 10/1991 |

(Continued)

OTHER PUBLICATIONS

"ASTM F1249 Water Vapor Transmission Rate (WVTR) Measurement With Amodulatedinfraredsensor", Online retrieved from"https://www.ametekmocon.com/servicessupport/astm-f1249";2024; 03 pages.

(Continued)

Primary Examiner — Anthony D Stashick
Assistant Examiner — Raven Collins
(74) Attorney, Agent, or Firm — Gregory P. Habiak; Daniel S. Albrecht; Christian M. Best

(57) ABSTRACT

The present disclosure is directed to a package of one or more absorbent articles. The package comprises a package material comprising natural fibers. The package comprises a plurality of panels comprising a consumer-facing panel. The package is sealed such that the one or more absorbent articles are enclosed therein. The package material exhibits a HuBa value of greater than about 5 hours, according to the HuBa Test. The package is recyclable. The package comprises a vertical side seal having a side seal strength that is in the range of about 5.1 N/15 mm to about 15 N/15 mm, according to Seal Tensile Strength Test. The package material comprises a barrier film comprising a first layer and a second layer. The first layer comprises a first polymer material and the second layer comprises a second polymer material. The first polymer material is different than the second polymer material.

18 Claims, 33 Drawing Sheets

(51) Int. Cl.
 *B65D 75/26* (2006.01)
 *B65D 75/56* (2006.01)

(52) U.S. Cl.
 CPC ........... *B65D 75/26* (2013.01); *B65D 75/563*
 (2013.01); *B65D 2565/385* (2013.01); *B65D*
 *2565/387* (2013.01)

(58) Field of Classification Search
 CPC . A61F 13/5511; B32B 2770/00; B32B 27/20;
 B32B 1/00; B32B 27/32
 USPC ...................................................... 206/524.1
 See application file for complete search history.

(56) References Cited

U.S. PATENT DOCUMENTS

| | | | |
|---|---|---|---|
| 2,821,337 A | 1/1958 | Morgan, Jr. | |
| 3,312,339 A | 4/1967 | Million | |
| 3,462,026 A | 8/1969 | MacCherone | |
| 3,519,197 A | 7/1970 | Campbell | |
| 3,640,450 A | 2/1972 | Lieberman | |
| 3,741,778 A | 6/1973 | Rowe | |
| 3,979,049 A | 9/1976 | Achelpohl | |
| 4,691,368 A | 9/1987 | Roessiger | |
| 4,951,824 A | 8/1990 | Kuchenbecker | |
| 4,988,332 A | 1/1991 | Mattle | |
| 5,065,868 A | 11/1991 | Cornelissen | |
| 5,419,956 A | 5/1995 | Roe | |
| 5,457,944 A | 10/1995 | Lipes | |
| 5,468,206 A | 11/1995 | Buchanan | |
| 5,509,915 A | 4/1996 | Hanson | |
| 5,722,774 A | 3/1998 | Hartz | |
| 5,830,118 A | 11/1998 | Nicholson | |
| 5,897,542 A | 4/1999 | Lash et al. | |
| 5,908,113 A | 6/1999 | Takemasa et al. | |
| 5,934,470 A | 8/1999 | Bauer et al. | |
| 6,033,112 A | 3/2000 | Sorenson et al. | |
| 6,446,796 B1 | 9/2002 | Schmidt | |
| 6,698,928 B2 | 3/2004 | Miller | |
| 6,854,600 B1 | 2/2005 | Persson | |
| 7,004,320 B1 | 2/2006 | Schmidt et al. | |
| 7,721,887 B2 | 5/2010 | Hancock-cooke et al. | |
| 7,780,353 B2 | 8/2010 | Yoffe | |
| 8,074,801 B2 | 12/2011 | Slayton et al. | |
| 8,097,313 B2 | 1/2012 | Wallat | |
| 8,240,915 B2 | 8/2012 | Sargin et al. | |
| 8,348,916 B2 | 1/2013 | Fujikawa et al. | |
| 8,631,939 B2 | 1/2014 | Benson et al. | |
| 8,794,443 B2 | 8/2014 | Ueda | |
| 8,899,418 B2 | 12/2014 | Francis | |
| 9,382,043 B2 | 7/2016 | Rummo | |
| 9,468,566 B2 | 10/2016 | Rosati et al. | |
| 9,827,150 B1 | 11/2017 | Sheehan | |
| 9,878,839 B2 | 1/2018 | Santos | |
| 9,914,562 B2 | 3/2018 | Fox et al. | |
| 9,932,149 B2 | 4/2018 | Puccini | |
| 9,994,376 B2 | 6/2018 | De Soto-burt et al. | |
| 10,378,152 B2 | 8/2019 | Kinast | |
| 10,760,219 B2 | 9/2020 | Niemi | |
| 10,786,404 B2 | 9/2020 | Cheng et al. | |
| 11,396,170 B2 | 7/2022 | Knauf et al. | |
| 11,420,784 B2 | 8/2022 | Parker et al. | |
| 11,794,976 B2 | 10/2023 | Remus | |
| 11,833,019 B2 | 12/2023 | Remus et al. | |
| 2001/0056270 A1 | 12/2001 | Mizutani et al. | |
| 2002/0148749 A1 | 10/2002 | Briseboi et al. | |
| 2003/0106825 A1 | 6/2003 | Molina et al. | |
| 2004/0232024 A1 | 11/2004 | Guerreschi | |
| 2004/0238393 A1 | 12/2004 | Ohi et al. | |
| 2004/0241359 A1 | 12/2004 | Miksic et al. | |
| 2006/0051603 A1 | 3/2006 | Cleveland et al. | |
| 2006/0191985 A1 | 8/2006 | Norcom | |
| 2007/0099542 A1 | 5/2007 | Sakaguchi et al. | |
| 2007/0230834 A1 | 10/2007 | Schneider | |
| 2009/0084698 A1 | 4/2009 | Ito et al. | |

| | | | |
|---|---|---|---|
| 2009/0145792 A1 | 6/2009 | Lewis | |
| 2009/0157033 A1 | 6/2009 | Toro et al. | |
| 2009/0249751 A1 | 10/2009 | Hyttel et al. | |
| 2010/0150479 A1 | 6/2010 | Smith | |
| 2010/0273377 A1 | 10/2010 | Files et al. | |
| 2011/0046591 A1 | 2/2011 | Warner | |
| 2011/0257616 A1 | 10/2011 | Lakso et al. | |
| 2012/0288693 A1 | 11/2012 | Stanley et al. | |
| 2013/0046271 A1 | 2/2013 | Pittet et al. | |
| 2013/0156352 A1 | 6/2013 | Koehn | |
| 2013/0220860 A1 | 8/2013 | Bacon | |
| 2014/0099455 A1 | 4/2014 | Stanley et al. | |
| 2014/0319003 A1 | 10/2014 | Hawighorst et al. | |
| 2014/0348445 A1 | 11/2014 | Siesto Casanova et al. | |
| 2015/0266663 A1 | 9/2015 | Joseph | |
| 2016/0038628 A1 | 2/2016 | Klofta et al. | |
| 2017/0057721 A1 | 3/2017 | Lee et al. | |
| 2017/0105889 A1 | 4/2017 | Nishimura et al. | |
| 2017/0260694 A1 | 9/2017 | Torniainen et al. | |
| 2017/0274613 A1 | 9/2017 | Stafford, III | |
| 2017/0350074 A1 | 12/2017 | Kinast | |
| 2018/0187377 A1 | 7/2018 | Ziegenbein | |
| 2018/0228675 A1 | 8/2018 | Hou | |
| 2018/0289564 A1 | 10/2018 | Sheehan | |
| 2018/0304607 A1 | 10/2018 | Öhman et al. | |
| 2018/0334292 A1 | 11/2018 | Tan | |
| 2019/0091077 A1 | 3/2019 | Cheng et al. | |
| 2019/0126603 A1 | 5/2019 | Zerial | |
| 2019/0135515 A1 | 5/2019 | Jasso | |
| 2019/0343695 A1* | 11/2019 | Ide .......................... A61F 13/49 | |
| 2020/0030162 A1 | 1/2020 | Lindner et al. | |
| 2020/0231365 A1 | 7/2020 | Veiseh | |
| 2020/0354129 A1 | 11/2020 | Sheehan et al. | |
| 2020/0368082 A1 | 11/2020 | Cheng et al. | |
| 2021/0043023 A1 | 2/2021 | Coder et al. | |
| 2021/0108371 A1 | 4/2021 | Oshima et al. | |
| 2021/0114789 A1 | 4/2021 | Kuiper et al. | |
| 2021/0221544 A1 | 7/2021 | Wallenius et al. | |
| 2022/0031531 A1 | 2/2022 | Remus et al. | |
| 2022/0031532 A1 | 2/2022 | Remus et al. | |
| 2022/0031533 A1 | 2/2022 | Remus et al. | |
| 2022/0033158 A1 | 2/2022 | Boswell et al. | |
| 2022/0033159 A1 | 2/2022 | Remus et al. | |
| 2022/0034040 A1 | 2/2022 | Boswell et al. | |
| 2022/0079819 A1 | 3/2022 | Houben et al. | |
| 2022/0110801 A1* | 4/2022 | Remus ................. B65D 65/466 | |
| 2022/0110802 A1 | 4/2022 | Remus et al. | |
| 2022/0112663 A1 | 4/2022 | Boswell | |
| 2022/0112664 A1* | 4/2022 | Boswell ................. D21H 19/12 | |
| 2022/0204234 A1 | 6/2022 | Chapjian | |
| 2022/0266563 A1 | 8/2022 | Schlarp et al. | |
| 2022/0304867 A1 | 9/2022 | Giovanni et al. | |
| 2022/0362073 A1 | 11/2022 | Shimizu et al. | |
| 2023/0011142 A1 | 1/2023 | Yoshiba | |
| 2023/0036459 A1 | 2/2023 | Yoshiba | |
| 2023/0060828 A1 | 3/2023 | Yoshiba | |
| 2023/0165737 A1 | 6/2023 | Remus et al. | |
| 2023/0166488 A1 | 6/2023 | Kohlweyer et al. | |
| 2024/0148570 A1 | 5/2024 | Remus | |
| 2024/0269014 A1 | 8/2024 | Remus | |
| 2024/0366438 A1 | 11/2024 | Remus | |
| 2025/0248866 A1 | 8/2025 | Motsch et al. | |
| 2025/0262102 A1 | 8/2025 | Motsch et al. | |

FOREIGN PATENT DOCUMENTS

| | | | |
|---|---|---|---|
| EP | 1291290 A1 | 3/2003 | |
| EP | 1618860 A1 | 1/2006 | |
| EP | 2276673 B1 | 1/2014 | |
| EP | 2730698 A1 | 5/2014 | |
| EP | 2796384 A1 | 10/2014 | |
| EP | 2704963 B1 | 9/2016 | |
| EP | 3561178 A1 | 10/2019 | |
| EP | 3575233 B1 | 3/2021 | |
| EP | 3643634 B1 | 7/2021 | |
| EP | 3865421 A1 | 8/2021 | |
| EP | 3954535 A1 | 2/2022 | |
| EP | 3901054 B1 | 8/2022 | |
| EP | 4070929 A1 | 10/2022 | |

(56)                 References Cited

FOREIGN PATENT DOCUMENTS

| | | | |
|---|---|---|---|
| GB | 823855 | A | 11/1959 |
| GB | 829215 | A | 3/1960 |
| GB | 1520492 | A | 8/1978 |
| GB | 2545456 | A | 6/2017 |
| JP | S58160033 | A | 9/1983 |
| JP | H05168660 | A | 7/1993 |
| JP | 3094949 | B2 | 10/2000 |
| JP | 2003128081 | A | 5/2003 |
| JP | 2005145561 | A | 6/2005 |
| JP | 2007262603 | A | 10/2007 |
| JP | 2010222006 | A | 10/2010 |
| JP | 2014198588 | A | 10/2014 |
| JP | 2015227517 | A | 12/2015 |
| JP | 2017218157 | A | 12/2017 |
| KR | 20080111808 | A | 12/2008 |
| NZ | 264733 | A | 4/1997 |
| WO | 9210412 | A1 | 6/1992 |
| WO | 9723186 | A1 | 7/1997 |
| WO | 02094678 | A1 | 11/2002 |
| WO | 02096331 | A2 | 12/2002 |
| WO | 2004103841 | A1 | 12/2004 |
| WO | 2011073808 | A2 | 6/2011 |
| WO | 2013008938 | A1 | 1/2013 |
| WO | 2013160199 | A1 | 10/2013 |
| WO | 2015088037 | A1 | 6/2015 |
| WO | 2019056351 | A1 | 3/2019 |
| WO | 2020121160 | A1 | 6/2020 |
| WO | 2021165317 | A1 | 8/2021 |
| WO | 2021199600 | A1 | 10/2021 |
| WO | 2021200656 | A1 | 10/2021 |
| WO | 2021200657 | A1 | 10/2021 |
| WO | 2022022884 | A1 | 2/2022 |
| WO | 2022059324 | A1 | 3/2022 |
| WO | 2022129674 | A1 | 6/2022 |
| WO | 2022158102 | A1 | 7/2022 |
| WO | 2023117604 | A1 | 6/2023 |

OTHER PUBLICATIONS

"Standard Test Method for Water Vapor Transmission Rate Through Plastic Film and Sheeting Using a Modulated Infrared Sensor Designation", 2013, 06 Pages.

"Standard Test Method for Water Vapor Transmission Rate Through Plastic Film and Sheeting Using a Modulated Infrared Sensor Designation", 2020; 04 Pages.

All Office Actions; U.S. Appl. No. 18/762,844, filed Jul. 3, 2024.

Unpublished U.S. Appl. No. 18/762,844, filed Jul. 3, 2024, to Andreas Peter Motsch et al.

"Axello Tough White White MF Kraft Paper", Online retrieved from "https://www.billerudkorsnas.com/packaging-materials/kraft-paper-bags/axello" ,2019, 01 page.

All Office Actions; U.S. Appl. No. 17/389,403, filed Jul. 30, 2021.

All Office Actions; U.S. Appl. No. 18/419,600, filed Jan. 23, 2024.

All Office Actions; U.S. Appl. No. 18/419,609, filed Jan. 23, 2024.

Jonathan Fowle et al. "Paper-based flexible packaging", 2003, pp. 91-123.

Mark J. Kirwan, "Paper and Paperboard Packaging Technology ", Available on https://www.booksfree.org/wp-content/uploads/2022/02/paper_and_paperboard_packaging_technology-signed.pdf, 2005, pp. 453.

Mespack Horizontal pouch machine, Available on https://www.youtube.com/watch?v=J6FKMopcMN8, Copy not provided.

Mespack Innovative Packaging Technologies, Available on https://www.e-morenos.com/wp-content/uploads/2017/06/NOU_cataleg_general_ENG.pdf, No Known Date, pp. 48.

Richard Coles et al. "Food Packaging Technology", available on https://kasianparto.ir/wp-content/uploads/2022/03/Food-Packaging-Technology.pdf, vol. 5, 2003, pp. 362.

Thorsten Schmidt et al. "Reliability of evaluations for the choice of system solutions at the example of automated order pickingsystems for bagged goods", May 30, 2014, pp. 14.

Unpublished U.S. Appl. No. 18/419,600, filed Jan. 23, 2024, to Andreas Peter Motsch et al.

Unpublished U.S. Appl. No. 18/419,609, filed Jan. 23, 2024, to Andreas Peter Motsch et al.

PCT Search Report and Written Opinion for PCT/US2024/012479; dated Jun. 12, 2024, 14 pages.

"Aegis Paper", Online retrieved from "https://www.nspackaging.com/news/mondi-aegispaper-barrier/";2021; 02 pages.

"Kraft paper", Online retrieved from "https://en.wikipedia.org/wiki/Kraft_paper"; Unknown date; 03 pages.

"Wax Paper", Online retrieved from "https://en.wikipedia.org/wiki/Waxed_paper"; Unknown date; 02 pages.

All Office Actions; U.S. Appl. No. 18/776,430, filed on Jul. 18, 2024.

All Office Actions; U.S. Appl. No. 19/184,293, filed on Apr. 21, 2025.

All Office Actions; U.S. Appl. No. 19/198,498, filed on May 5, 2025.

All Office Actions; U.S. Appl. No. 19/312,937, filed on Aug. 28, 2025.

U.S. Unpublished U.S. Appl. No. 19/312,937, filed on Aug. 28, 2025, to Andreas Peter Motsch et al.

* cited by examiner

1480

1400

1411

1460

1413

1450

1440

1415

1414

1412

1420

1430

1410

RECYCLABLE ABSORBENT ARTICLE PACKAGES

CROSS REFERENCE TO RELATED APPLICATIONS

This application claims the benefit, under 35 U.S.C. § 119(e), of U.S. Provisional Patent Application No. 63/441,001, filed on Jan. 25, 2023, and U.S. Provisional Patent Application No. 63/514,817, filed on Jul. 21, 2023, the entire disclosures of both of which are fully incorporated by reference herein.

FIELD

The present disclosure relates to packages of disposable absorbent articles, and more particularly, to packages of disposable absorbent articles that are recyclable, exhibit required seal strengths, barrier properties, and shelf life, and are processable on high speed manufacturing equipment.

BACKGROUND

Products and packaging which are environmentally friendly are at the forefront of many consumer's minds at this point in our history. There is an increased focus on products and packaging which are sustainably sourced. For example, there is a strong desire in the marketplace to create consumer products and packaging which comprise natural materials, bio-sourced materials, and/or recycled materials. On the disposal end, there is an increased focus on products and packaging which are bio-degradable, compostable, recyclable, reusable, and/or otherwise cause minimal landfill waste.

There are absorbent articles packages which utilize carton board as their on shelf package. Carton board, as it is derived from wood pulp, may be sustainably sourced and recyclable. And, where the products within the package cannot form a shelf stable surface on their own, carton board is useful because of its structural integrity. The problem with carton board alone is it does not prevent atmospheric moisture from reaching the absorbent articles and causing issues like preactivation of SAP and/or wetness indicators.

There are absorbent articles packages which utilize plastic films as their on shelf package. Plastic can exhibit barrier properties protecting the absorbent articles within the plastic packaging from atmospheric moisture. However, plastic films may not be viewed as environmentally friendly by consumers.

As such, there is growing public demand for alternatives to plastic and carton board packaging materials for absorbent articles that exhibit sufficient barrier properties to atmospheric moisture and that are environmentally friendly.

SUMMARY

The packages of the present disclosure provide packaging material for absorbent articles that exhibit sufficient barrier properties to atmospheric moisture and that are environmentally friendly. The packages may comprise natural fibers and one or more barrier film layers. The packages may also comprise a certain HuBa factor which equates to long lasting shelf life when absorbent articles are placed within the packages.

Packages of the present disclosure comprise one or more absorbent articles therein and comprise a package material comprising natural fibers. Each of the packages comprises a plurality of panels, including a consumer-facing panel, wherein the package is sealed such that the one or more absorbent articles are enclosed by the package material. Additionally, the packages of the present disclosure are recyclable.

The present disclosure is directed, in part, to a package of one or more absorbent articles. The package comprises a package material comprising natural fibers. The package comprises a plurality of panels comprising a consumer-facing panel. The package is sealed such that the one or more absorbent articles are enclosed therein. The package material exhibits a HuBa value of greater than about 5 hours, according to the HuBa Test herein. The package material and/or the package is recyclable. The package comprises a side seal having a side seal strength that is greater than about 5.1 N/15 mm to about 15 N/15 mm, according to the Seal Tensile Strength Test. The package material comprises a barrier film layer comprising a first layer and a second layer. The first layer comprises a first polymer material or a first polyolefin material and the second layer comprises a second polymer material or a second polyolefin material. The first polymer material or the first polyolefin material is different than the second polymer material or the second polyolefin material. The first polymer material or the first polyolefin material may at least partially comprise post-consumer recycle "PCR" or post-industrial recycle "PIR". The second polymer material or the second polyolefin material may at least partially comprise PCR or PIR. At least some of the natural fibers may at least partially comprise PCR and/or PIR natural fibers.

The present disclosure is directed, in part, to a package of one or more absorbent articles. The package comprises a package material, wherein the package material comprises natural fibers. The package comprises a plurality of panels comprising a consumer-facing panel. The package is sealed such that the one or more absorbent articles are enclosed therein. The package material exhibits a HuBa value of greater than about 5.3 hours to about 20 hours, according to the HuBa Test. The package material or the package is recyclable. Each of the one or more absorbent articles comprises super absorbent polymer (SAP) in an amount of greater than about 5 grams per article.

The present disclosure is directed, in part, to a package of one or more absorbent articles. The package comprises a package material, wherein the package material comprises natural fibers. The package comprises a plurality of panels comprising a consumer-facing panel, wherein the package is sealed such that the one or more absorbent articles are enclosed therein. The package material exhibits a HuBa value of greater than about 5.3 hours, according to the HuBa Test. The package material and/or the package is recyclable. The package comprises a vertical side seal having a side seal strength that is greater than about 5.1 N/15 mm and less than about 15 N/15 mm, according to Seal Tensile Strength Test.

DETAILED DESCRIPTION

Figure 1A:
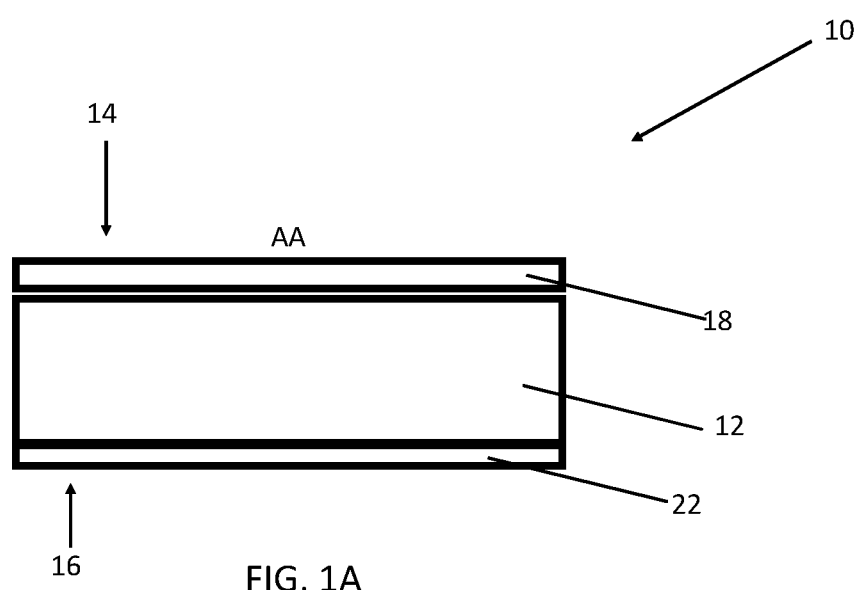
FIG. 1A is a schematic representation of a portion of a package material in accordance with the present disclosure.

The term "absorbent article" as used herein refers to devices which absorb and contain bodily exudates, and, more specifically, refers to devices which are placed against or in proximity to the body of the wearer to absorb and contain the various bodily exudates discharged from the body. Absorbent articles of the present disclosure include, but are not limited to, diapers, adult incontinence briefs, training pants, swim pants, diaper holders, diaper outer covers, absorbent inserts for the diaper outer covers, menstrual pads, incontinence pads, liners, pantiliners, tampons, durable menstrual pants, and the like.

The term "cross-machine direction" or "CD", as used herein, refers to the path that is perpendicular to the machine direction in the plane of the web.

The term "machine direction" or "MD", as used herein, refers to the path that material, such as a web, follows through a manufacturing process.

The term "colorant", as used herein, refers to inks, dyes, pigments, or the like, used to create color in a substrate.

The term "natural fibers" as used herein, refers to fibers which comprise cellulose-based fibers, bamboo based fibers, and the like. Natural fibers also refers to nonwoody fibers, such as cotton, abaca, kenaf, sabai grass, flax, esparto grass, straw, jute hemp, bagasse, milkweed floss fibers, and pineapple leaf fibers; and woody, wood, or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. The natural fibers of the present disclosure may be recycled natural fibers, virgin natural fibers or mixes thereof. Additionally, for good mechanical properties in natural fibers, it can be desirable that the natural fibers be relatively undamaged and largely unrefined or only lightly refined. The fibers can have a Canadian Standard Freeness of at least 200, more specifically at least 300, more specifically still at least 400, and most specifically at least 500.

The term "cellulose-based fibers," as used herein, may include cellulose fibers such as wood fiber, cotton, regenerated cellulose fiber such viscose, lyocell, rayon or cuprammonium rayon, and high pulping yield fibers, unless specified differently. The term "cellulose-based fibers" also includes chemically treated natural fibers, such as mercerized pulps, chemically stiffened or crosslinked fibers, or sulfonated fibers. Also included are mercerized natural fibers, regenerated natural cellulosic fibers, cellulose produced by microbes, the rayon process, cellulose dissolution and coagulation spinning processes, and other cellulosic material or cellulosic derivatives. Other cellulose-based fibers included are paper broke or recycled fibers and high yield fibers. High yield pulp fibers are those fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin but are still considered to be natural fibers. High yield fibers are well known for their stiffness in both dry and wet states relative to typical chemically pulped fibers.

Package materials or packages for one or more absorbent articles, especially premium absorbent article products, generally should meet certain requirements including the following: 1) reliable running on a high speed converting line; 2) provide protection to the absorbent articles during distribution in a supply chain; 3) withstand the handling associated with stocking on a retail shelf or in the e-commerce shipping system; 4) provide protection to the housed absorbent articles while in transit to a consumer's home and before they are actually worn; and 5) meet items 1-4 for the extent of the package life or life of the product through the distribution system from the manufacturer until the product is actually used. A problem facing absorbent article manufacturers when using packaging materials comprising natural fibers, wood fibers, and/or paper substrates with a barrier film layer is simultaneously realizing the required combination of side seal strength, recyclability, and barrier film layer properties, as these are the design options for the manufacturer to meet the items 1-5 above. One could meet recyclability requirements by decreasing the barrier film layer basis weight, but then the side seam strength and/or barrier film layer properties may be compromised. If the barrier film layer basis weight was increased, side seam strength and/or barrier layer film properties may meet the requirements, but recyclability may not meet requirements or targets. Consequently, there exists a need for improved packages of one or more absorbent articles comprising package materials comprising natural fibers and one or more barrier film layers which simultaneously meet side seal strength, recyclability, and barrier film layer requirements.

The barrier film layer properties of packages and package materials were designed using approaches including ones involving various Water Vapor Transmission Rates (WVTR) methods. The inventors have discovered the WVTR approach to assess the barrier film layer properties may not be a reliable predictor of the actual shelf life of a package and actual survivability of the products within the package. Therefore, there exists a need for more predictive methods, package materials, and packages for more accurately assessing and designing the package life and to use in designing improved packages of one or more absorbent articles comprising package materials comprising natural fibers and barrier film layers.

So, there is a need for packages of one or more absorbent articles comprising package materials comprising natural fibers and one or more barrier film layers, wherein the package material also exhibits a high performance combination of recyclability, side seam strength, and barrier film layer properties as measured by a HuBa factor (which equates to package shelf life). Furthermore, there is a need for packages of one or more absorbent articles comprising package materials comprising natural fibers and one or more barrier film layers, wherein the package materials also exhibit select ranges of barrier film layer properties as measured by a HuBa factor, recyclability, and super absorbent polymer level per absorbent article. There is also a need for packages of one or more absorbent articles comprising a package material comprising natural fibers and one or more barrier film layers, wherein the package materials also exhibit a high performance combination of recyclability, side seam strength, and the barrier film layer properties as measured by a HuBa factor. The one or more barrier film layers optionally comprise a first barrier film layer and a second barrier film layer where the two layers comprise different materials, such as polymers or polyolefins. The one or more barrier film layers are self-scalable, meaning that they will melt to form a seal when an inside surface of one portion of a package is joined with an inside surface of another portion of the package. Meeting these unmet needs are of the utmost commercial importance particularly as it relates to packages of one or more absorbent articles made on high speed converting lines and having acceptable product shelf life.

While not wishing to be bound by theory, the inventors have unexpectedly discovered packages of one or more absorbent articles comprising package materials comprising natural fibers and one or more barrier film layers, wherein the package materials also exhibit a high performance combination of recyclability, side seam strength, and barrier film layer properties may be achieved by designing the barrier film layer as two or more layers. The composition of the two or more barrier film layers facilitates the simultaneous use of different materials in each layer, where the different materials separately deliver against the overall package requirements, including barrier film layer requirements. For example, one barrier film layer may deliver superior side seam strength and the other barrier film layer may deliver superior barrier film layer properties or HuBa factor. With the performance requirements for side seam strength and barrier film layer properties divided between the two barrier film layers, the total level (or basis weight) of the two combined layers may be decreased, leading to meeting of recyclability requirements. This creates a select novel domain of package designs.

The inventors have surprisingly found select ranges of recyclability, side seam strength, and barrier film layer properties as measured by a HuBa factor and when these ranges are exhibited, a package with superior performance and package life is realized. The inventors have separately found that when the packages comprising package materials comprising natural fibers and barrier film layers, and exhibiting select ranges of barrier properties as measured by a HuBa factor, recyclability, and super absorbent polymer level per absorbent article, the resulting packages are superior in performance and product life. The inventors also have unexpectedly found that when the barrier film layer comprises two layers, each barrier film layer comprising polymer materials or polyolefin materials which are different than one other, the resulting packages are superior in performance and package life. The inventors have further unexpectedly found when the barrier film layer comprises two layers, one layer comprising low density polyethylene and the other comprises high density polyethylene, the resulting packages are superior in performance and package shelf life. Importantly, the superior package performance may include having absorbent articles contained therein with substantially unactivated wetness indicators and super absorbent polymers without moisture content and the overall side seal or same strength and recyclability requirements are also met.

While not wishing to be bound by theory, the inventors have discovered and describe herein a HuBa method for assessing the true barrier performance of packages of one or more absorbent articles comprising package material comprising natural fibers and one or more barrier film layers. This method provides an output time measure which the inventors have found to be more predictive of actual package shelf life compared to WVTR methods. The package shelf life may be a measure of how long the packages of one or more absorbent articles retain superior performance before potentially beginning to see negatives associated with humidity exposure, such as a loss of absorbent capacity, stiffening of the absorbent cores, and/or premature activation of wetness indicators. These negatives manifest the most for absorbent articles comprising higher levels of super absorbent polymer or for absorbent articles comprising greater than about 5 grams of super absorbent polymer per article. Upon information and belief, previous methods for measuring barrier properties involving WVTR type methods lacked awareness of the problem associated with delivering against product shelf life requirements. These WVTR methods provide a flux rate of moisture transmission through a given package or package material, but may not provide perspective on the subject of package life or product life. The inventors have found the time kinetics and time measurement output of the HuBa method may be more predictive and correlating with the ultimate shelf life of packages of one or more absorbent articles comprising package material containing natural fibers and one or more barrier film layers.

Packages of the present disclosure may comprise absorbent articles therein which comprise super absorbent polymer, i.e., SAP therein. The packages of the present disclosure may comprise one or more barrier film layers which reduces the rate of transfer of moisture through the package material to the SAP of the absorbent articles within the package. Additionally, the absorbent articles of the present disclosure may comprise a wetness indicator which indicates when the absorbent article has incurred a liquid insult. The one or more barrier film layers of the packages of the present disclosure slows moisture from being absorbed by the absorbent articles therein such that these wetness indicators can stay unactivated for a much longer period of time on shelf as compared to the absence of the one or more barrier film layers.

The inventors have surprisingly found that some absorbent articles are more susceptible to water or moisture vapor absorption than others. As an example, absorbent articles which include a moisture sensitive indicator or wetness indicator, e.g. diapers and/or training pants. These wetness indicators may be triggered in their packages prior to use depending on the environmental conditions in which the package of absorbent articles is situated. Additionally, absorbent articles which have high amounts of SAP, typically absorbent gelling material, may also present problems with humid environments. As an example, the SAP in these absorbent articles may change color after absorbing an amount of moisture, in the form of water vapor, from the environment. Unfortunately, this color change can cause concern amongst wearer or caregivers alike.

Additionally, the inventors have surprisingly found that while SAP is effective at absorbing moisture from its environment in the form of water vapor, its absorption of water vapor does not continue until the capacity of the SAP is depleted. Instead, the SAP will absorb water vapor for a period of time, e.g. weeks under stress conditions (described hereafter), and approaches steady state. Steady state for the amount of water vapor absorbed by SAP is much lower than the overall capacity of the SAP. So, the SAP within the absorbent article still has capacity to absorb liquid insults during use. As an example, steady state can be less than about 10 percent of the total capacity of the absorbent article. However, even at under 10 percent, enough water vapor may be absorbed to activate wetness indicators prior to wear and/or cause a color change in the SAP.

A myriad of factors can impact the absorption of moisture by SAP in an absorbent article. As an example, the inventors, while not wishing to be bound by theory, have found the cellulose within absorbent articles is not as susceptible to absorption of moisture of water vapor as is SAP. It is theorized that cellulose material within the absorbent article does not absorb as much water vapor from the environment as does SAP. As such, it is theorized that absorbent articles having a high ratio of cellulose to SAP by weight may not absorb as much moisture vapor from the environment as those absorbent articles with a lower ratio of cellulose to SAP by weight. Similarly, it is theorized that absorbent articles with a high weight or grams of SAP per absorbent article may also absorb more water vapor that absorbent articles with very low weight or grams of SAP.

For example, menstrual pads typically have much less SAP per article than do diapers or training pants. And similarly, menstrual pads typically have much less SAP per article than do adult incontinence pads and/or pants. It is theorized that absorbent articles comprising SAP in an amount of greater than 5 grams per article, greater than 8 grams per article, or greater than 10 grams per article, would potentially benefit from the packages of the present disclosure.

Additionally, it is theorized that the amount of breathability of the backsheet of the absorbent article may similarly contribute to or influence the amount of water vapor absorbed by SAP while in an absorbent article package. As an example, a non-breathable film may provide a high barrier to moisture absorption by SAP, while the SAP containing articles are in a package. However, for diapers, pants, and adult incontinence pants with breathable films as a backsheet component, such breathable films are theorized to allow humidity to traverse the space between or diffuse between adjacent absorbent articles within a package. Therefore, it is believed that absorbent article packaging materials of the present disclosure are particularly needed for absorbent articles comprising breathable films as a backsheet component.

Another feature which can impact the amount of moisture vapor absorbed by SAP in an absorbent article is the package. While plastic films can make great moisture barriers and hinder the absorption of moisture vapor by the SAP, plastic films are generally seen as contaminants in a recycling process which is meant for natural fibers, e.g. wood pulp and/or cellulosic materials. However, the inventors have surprisingly found a packaging material which comprises a natural fiber layer and one or more barrier film layers and yet is still recyclable. The one or more barrier film layers may be disposed on an inner surface of the natural fiber layer or on an outer surface. The one or more barrier film layers may comprise plastic or comprise polymeric materials. In an example, the one or more barrier film layers may comprise a polymer, a polyolefin, e.g. polyethylene, polypropylene, or combinations thereof. As another example, a first barrier film layer may comprise low density polyethylene and a second barrier film layer may comprise high density polyethylene. In another example, both the first barrier film layer and the second barrier film layer may comprise low density polyethylene or both may comprise high density polyethylene. For the sake of clarity, the one or more barrier film layers while likely not recyclable in the same recycling process as the natural fiber, may be recyclable via other recycling means, e.g. plastic film, plastic bag recycling.

Regarding the recyclability of the package material and/or the package, there is no uniform standard which determines the recyclability of a material. In general, the higher the percent yield of natural material, the more likely the material is able to be recycled in a paper recycling stream. In order to accommodate the higher percent yield of natural material, e.g. wood pulp and/or cellulose, the weight percentage of the film compared to that of the natural fiber should be substantially less. As an example, the one or more barrier film layers can make up about 40 percent by weight or less, about 30 percent by weight or less, about 20 percent by weight or less, about 10 percent by weight or less, about 5 percent by weight or less, or about 5 percent to about 20 percent, of the overall package material. As another example, the one or more barrier film layers can make up from between about 3 percent by weight to about 40 percent by weight, from about 3 percent by weight to about 30 percent by weight, or from about 3 percent by weight to about 20 percent by weight. In one specific example, the one or more barrier film layers may make up about 5 percent by weight or less of the overall package material weight, about 4 percent or less, or about 3 percent or less. In another specific example, the film may make up from between about 1 percent by weight to about 5 percent by weight, from about 1 percent by weight to about 4 percent by weight, or from about 1 percent by weight to about 3 percent by weight.

The basis weight of the package material can have a basis weight of from between about 50 gsm to about 220 gsm, about 50 gsm to about 120 gsm, between about 60 gsm to about 100 gsm, between about 70 gsm to about 90 gsm, about 75 gsm, about 80 gsm, or about 85 gsm. The basis weight can be determined via ISO 536 as modified herein.

The basis weight of the one or more barrier film layers should be at least about 2 gsm to less than about 25 gsm. It is theorized that below this basis weight, the film may not cover a sufficient enough portion of the bag to provide a suitable barrier property. However, aside from the foregoing, the one or more barrier film layers may be any suitable basis weight so long as the one or more barrier film layers' basis weight is within the weight percentages described herein.

It is worth noting that the one or more barrier film layers laminated, coated, or otherwise joined to the natural fiber layer forms a synergistic relationship particularly where the one or more barrier film layers are desired to be a smaller weight percentage of the overall package material. For example, where the one or more barrier film layers is 5 percent by weight or less of the overall package material, this can be a very small basis weight barrier film layer for the basis weight of package materials described heretofore. At this very low basis weight, it is believed that the one or more barrier film layers would not be able to be processed reliably without being coated, laminated, or otherwise joined to the natural material layer. And similarly, without the addition of the one or more barrier film layers, the natural material layer may not be able to provide much, if any, inhibition to the absorption of moisture vapor by the SAP within the absorbent articles in the package.

Regarding a method by which the one or more barrier film layers may be joined to the natural fiber layer, an example method is described hereafter. The one or more barrier film layers can be a polymer that is water insoluble. The polymer may be obtained from a manufacturer as a pre-made dispersion/emulsion of the polymer, or a dispersion/emulsion may be formed if a pre-made dispersion/emulsion is not available. The aqueous polymeric system is then coated onto the natural fiber layer and the water (or other solvent e.g. alcohol) may then be removed via convective or diffusive drying process. Afterwards, enough heat may be applied to form a continuous polymeric layer.

Without being limited to theory, it is believed that the most important material properties of the aqueous polymeric system are: a) the ability of the polymer to be made into an emulsion in water; b) the resulting viscosity of the aqueous polymeric system at that temperature, higher viscosity being better for maximum distinction/separation between the layers; c) the wetting of the aqueous polymeric system either onto a substrate to be coated, higher wetting being better.

Another example involves thermal extrusion coating. Thermal extrusion coating is used to apply a composition that is not water-borne. In this method, the polymeric composition may be melted within an extruder; the molten polymeric composition is thermally extruded onto the surface of the natural fiber layer followed by cooling to form the package material.

In yet another example, the one or more barrier film layers may be applied to the natural fiber layer via adhesive lamination. If such an execution is performed, care should be taken regarding the type of adhesive as well as the amount of adhesive used as this could impact the overall recyclability of the package material. If such an arrangement was used, an adhesive layer can be applied directly to the natural fiber layer, and a pre-made barrier film layer or layers would then be applied to the adhesive layer. A polymeric composition can be made into a pre-made barrier film layer or layers by a variety of methods including solution casing, thermal cast film extrusion and thermal blown film extrusion. In yet another example, heat lamination may be used to adhere the polymeric barrier film layer or layers to the natural fiber layer.

Regarding suitable polymeric compositions that can be utilized in the one or more barrier film layers, there are many that could be either biodegradable or could be non-biodegradable. Some examples of biodegradable options include aliphatic aromatic polyesters (e.g., ECOFLEX® from BASF), certain thermoplastic starches (e.g., MATER-BI from Novamont's or PLANTIC® from Plantic/Kuraray), polybutylene succinate and copolymers thereof (e.g., BION-OLLE® from ShoWa High polymer Co. or PBSA from Mitsubishi Chemicals), polycaptralactone and mixtures thereof. Other suitable polymers include polhydroyxalkoanates (PHA) and PHA copolymers such as poly(beta-hydroxyalkanoate), poly(3-hydroxybutyrate-co-3-hydroxyhexanoate) NODAX™ from Danimer, and poly(3-hydroxybutyrate-co-3-hydroxyhexanoate) from Kaneka. Non-limiting examples of PHA copolymers include those described in U.S. Pat. No. 5,498,692. Other PHA copolymers can by synthesized by methods known to one skilled in the art, such as, from microorganisms, the ring-opening polymerization of beta-lactones, the dehydration-polycondensation of hydroxyalkanoic acid, and the de-alcoholization-polycondensation of the alkyl ether of hydroxyalkanoic acid, as described in Volova, "Polyhydroxy Alkanoates Plastic Materials of the 21" Century: Production, Properties, and Application, Nova Science Publishers, Inc., (2004), incorporated herein by reference. Another example is poly-lactic acid (PLA). Additional examples of non-biodegradable options include polyolefin materials, for example: polyethylene (PE), polypropylene (PP), and polyethylene terephthalate (PET). Examples of polyethylene could include high density polyethylene, low density polyethylene, linear low density polyethylene, medium density polyethylene—including all homopolymers and copolymers of those materials. Other examples of non-biodegradable options could include various Surlyn's; copolymers of styrene-butadiene e.g. acrylo-nitrile-butadiene; acrylic copolymers; acrylate copolymers (including methyl methacrylate); acetate copolymers including EVA (ethylene vinyl acetate). The polymers could in some cases include fillers additives such as clays (e.g. kaolin) and other mineral additives such as $CaCO_3$ or $TiO_2$.

Ideally, the package materials of the present disclosure would provide unlimited protection inhibiting the absorption of moisture vapor by the SAP in the absorbent articles therein. However, as explained previously, the addition of one or more barrier film layers to the natural fibers can negatively impact the recyclability of the natural fibers. So, careful selection of the one or more barrier film layers and thus the package material should be taken.

The barrier properties of the package material of the present disclosure can be measured via the Humidity Barrier Rapid Test described herein, i.e., also known as the "HuBa Test". This HuBa Test can provide useful information regarding the humidity transmission of a package material.

In order to reduce the likelihood of the wetness indicators being activated prematurely, stiffening of absorbent cores, and SAP with partial absorption of moistures, the inventors have surprisingly found that the package materials should have a HuBa value of greater than about 5 hours, greater than about 5.1 hours, greater than about 5.2 hours, greater than about 5.3 hours, about 5 hours to about 20 hours, about 5.1 hours to about 15 hours, about 5.2 hours to about 15 hours, about 5.3 hours to about 20 hours, about 5.3 hours to about 15 hours, about 5.3 hours to about 14 hours, about 5.3 hours to about 13 hours, about 5.3 hours to about 12 hours, about 5.3 hours to about 11 hours, about 5.3 hours to about 10 hours, about 5.3 hours to about 9 hours, about 5.3 hours to about 8.8 hours, about 5.3 hours, about 8.8 hours, or about 6 hours. The HuBa values above equate to months of shelf life from when the package is sealed to when the product inside the package is used. The shelf life (with the absorbent articles having wetness indicators unactivated) may range from about 5 months to about 18 months, about 6 months to about 16 months, about 6 months to about 15 months, about 6 months, about 11 months, or about 15 months.

Data for package material samples 1-4 is provided below in Table 1.

natural fibers. The low density polyethylene is in contact with the high density polyethylene.

Present Disclosure Example: Sample 4 is an 80 gsm advanced smooth white paper with a single barrier film layer on one side. The low density polyethylene is in contact with the natural fibers.

Of the above tested Samples 1-4, the inventors have found that only Samples 2-4 satisfy the prerequisites described herein. Namely, Samples 2-4 provide an adequate barrier to atmospheric moisture as described herein as well as have a high recyclability percentage, and a high seam or seal strength. The mechanical properties of the package material of the present disclosure are described hereafter.

Instead of having a 100% coating of LDPE across the entire inner surface of the packaging material, only certainly regions may have the LDPE. HDPE has more desirable barrier properties than LDPE, but LDPE has more desirable sealing and/or seaming properties. As such, it may be desirable to include the HDPE at a higher basis weight across all of, or most of, the inner surface of the packaging material and provide the LDPE only at seams and/or sealing areas where the LDPE has the most functionality. As an example, instead of having the coatings of Present Disclosure Example, Sample 2, the inner surface of the packaging material may be coated with 10 g of HDPE at 100% area of the inner surface and 6 g of LDPE at about 5% to about 35% area, about 5% to about 25% area, about 10% to about 20% area, or about 15% area of the inner surface of the package material. The LDPE may be placed in areas of the seams or where seaming or scaling occurs. Stated different, the LDPE may not overlap all of the HDPE. For example, the LDPE may be placed in, or only placed in, areas of the vertical left side seam 40, the vertical right side seam 42, the first left side angled seam 44, the second left side angled seam 46, the first right side angled seam 48, the second right side angled seam 50, and in other seaming or scaling areas. See e.g., FIGS. 2A-2F. This would allow the package to have improved barrier properties, with adequate seaming and/or scaling properties, and while still meeting the recyclability guidelines. Instead of LDPE being present in the sealing and/or seaming areas, other bonding enhancement agents with desirable heat scalability and sufficient seal and/or

TABLE 1

| Sample No. | Basis Weight of Natural Fibers (gsm) | Basis Weight of HDPE (gsm) | Basis Weight of LDPE (gsm) | HuBa (hours) | Side Seal Strength (N/15 mm) | 45° Seal Strength (N/15 mm) | PTS % | Overall Recyclability Score |
|---|---|---|---|---|---|---|---|---|
| 1 | 80 | 0 | 4 | 2.1 | 4.8 | 4.3 | 92.3 | Pass |
| 2 | 80 | 5 | 6 | 5.3 | 6.1 | 5.7 | 88 | Pass |
| 3 | 80 | 10 | 6 | 8.8 | 7.6 | 7.2 | 82.8 | Pass |
| 4 | 80 | 0 | 14 | 6 | 7.8 | 6.7 | 82 | Pass |

Comparative Example: Sample 1 is an 80 gsm advanced smooth white paper with a single barrier film layer on one side. The low density polyethylene is in contact with the natural fibers.

Present Disclosure Example: Sample 2 is an 80 gsm advanced smooth white paper with two barrier film layers on one side. The high density polyethylene is in contact with the natural fibers. The low density polyethylene is in contact with the high density polyethylene.

Present Disclosure Example: Sample 3 is an 80 gsm advanced smooth white paper with two barrier film layers on one side. The high density polyethylene is in contact with the seam strength may be used. An example of a bonding enhancement agent is a heat sealable adhesive. Bonding enhancement agents may be flexo-printed, dispersion coated, applied by ink jet printing, or applied using any other specific application technology.

Instead of using HDPE and LDPE as the barrier and/or sealing materials, the natural fibers may be coated with clay, hectorite, and/or PET that is not scalable, but does provide a suitable barrier. Another option would be to join metalized paper, or other inorganic barrier material, to the natural fibers, which again provides a suitable barrier. Aluminiumoxide barriers are also contemplated to be joined the natural fibers. The Aluminiumoxide barriers are transparent which may be desirable and/or less noticeable to consumers. With all of these options, bonding enhancement agents may be applied to seal and/or seam areas on the inner surface of the package material to allowed seals or seams to be formed when the package is made even though the initial barrier materials are not scalable. In general, the clay, hectorite, PET, metalized paper, inorganic barriers, and/or aluminiumoxide, including the bonding enhancement agents in the seal or seam areas may be less than about 15%, less than about 10%, less than about 5%, about 2% to about 10%, or about 3% to about 8%, by weight of the laminate of these materials and the natural fibers to meet recycling requirements.

Regarding the unactivated wetness indicator of the package of the one or more absorbent articles of the present disclosure, it is worth discussing the various types of wetness indicators. First, a wetness indicator may appear as a first color in its dry state and change to a second color as the wetness indicator becomes wet. As more liquid is introduced into the absorbent core of the absorbent article, more of the wetness indicator changes from the first to the second color. Where the absorbent article is completely full, the wetness indicator will typically show only the second color.

A second type of wetness indicator may involve graphics which only appear after wetness has been received by the wetness indicator. For example, in its dry state, the wetness indicator may not be visible or distinguishable from the surrounding color of the absorbent article. In such wetness indicators, much like the first type, once liquid is received by the wetness indicator, a color change may occur which is visible either through a wearer-facing surface and/or a garment-facing surface of the article. Depending on the amount of liquid received by the wetness indicator, only a small portion may be activated to produce a color change. Or, if a large amount of liquid is received, then a larger portion or all of the wetness indicator may be activated to produce the visible color change.

A third type of wetness indicator may involve disappearing graphics. As an example, a graphic of a full cartoon character, for example, may appear in the dry state of the article. Once the article begins to absorb liquid, the cartoon character will start to disappear. Once the article is full, the cartoon character may not appear at all of the majority of it may not appear.

Based on the foregoing discussion on wetness indicators, an unactivated wetness indicator is one in which the wetness indicator is substantially available to receive and indicate the level of liquid within the article. For example, in the case of color changing or appearing wetness indicators, a substantially unactivated wetness indicator is one in which 70 percent or more, 85 percent or more, or 95 percent or more, of the area of the wetness indicator (i) is the original (dry) color or (ii) has not appeared. As another example, regarding disappearing graphics, a substantially unactivated wetness indicator is one in which the disappearing graphic is present at about 70 percent or more, 85 percent or more, or 95 percent or more.

It is worth noting that where a desired recyclability percentage of the package materials of the present disclosure are between 60 percent and 70 percent, a much more restrictive barrier to moisture may be accommodated. It is theorized that for such constructions, the one or more barrier film layers may comprise from between about 30 percent by weight to 40 percent by weight and may exhibit a HuBa of about 22 hours to about 32 hours. Where the desired recyclability percentage of the package materials of the present disclosure are between 70 percent and 80 percent, the weight percentage of the one or more barrier film layers may be between 20 percent by weight and 30 percent by weight. It is believed that at such levels, the package material of the present disclosure may exhibit a HuBa of about 15 hours to about 22 hours. Where the desired recyclability percentage of the package material of the present disclosure is between 80 percent and 90 percent, the one or more barrier film layers may comprise from between 10 percent by weight and 20 percent by weight. It is believed that at such levels, the package material of the present disclosure may exhibit a HuBa of about 8 hours to about 15 hours. Where the desired recyclability percentage of the package material of the present disclosure is desired to be greater than 90 percent, the one or more barrier film layers may comprise 10 percent or less by weight. It is believed that at such levels, the package material of the present disclosure may exhibit a HuBa of about five hours to about 8 hours.

The inventors have also surprisingly found that the rate of moisture absorption could further be reduced via additional packaging. As an example, the package material of the present disclosure may be utilized as a primary package. The primary package is the package which comprises the absorbent articles therein. The primary package is typically what is placed on shelf and sold to consumers.

To ship primary packages to retailers, secondary packages may be utilized. Secondary packages typically comprise a plurality of primary packages therein. In order to reduce the rate at which moisture is absorbed by the absorbent articles, these secondary packages may similarly be provided with one or more barrier film layers either internally and/or externally. This internal and/or external one or more barrier film layers can reduce the rate at which moisture is absorbed by the absorbent articles within the primary package. Additionally or independently of the one or more barrier film layers of the secondary packages, a plurality of secondary packages may be shipped together on a pallet. This plurality of secondary packages may also comprise a film wrap which helps stabilize the plurality of secondary packages. However, in addition to stabilizing the plurality of secondary packages, this film wrap may further reduce the rate of water vapor absorption within the primary packages. These film wraps for pallet stabilization are generally polyolefin based.

The plurality of secondary packages can stay wrapped in the outer film wrap until required to unpack by a seller of the products. Similarly, the secondary packages may stay sealed until the primary packages therein are needed. Each of the secondary packages may comprise package information providing instructions on how and/or when to open. Such information can help reduce the overall amount of moisture absorbed by the SAP in the absorbent articles as the secondary packages would not be opened until needed.

Where the packages of the present disclosure have sufficient barrier to moisture absorption, wetness indicators as well as SAP within the absorbent articles will have a longer shelf life. For example, it is believed that under stress conditions, i.e., 40 degrees C. and 75 percent relative humidity, the absorbent articles within the packages of the present disclosure will absorb less than 4.5 grams of moisture per article for a sufficient period of time. Additionally, it is believed that absorbent articles within the packages of the present disclosure will absorb less than 7 grams, or less than 5 grams of moisture per article for an even longer period of time.

As noted previously, the one or more barrier film layers in the package material of the present disclosure is considered to be a contaminant in the recycling process for natural based materials, e.g. wood pulp and/or cellulose. Unfortunately, in addition to the one or more barrier film layers, other materials which may be utilized in the construction of the packages of the present disclosure may also be deemed contaminants. For example, the packages of the present disclosure comprise seals or seams. These seals ensure that the absorbent articles within the package have reduced likelihood of contamination from the environment external to the package. Additionally, colorant and/or coatings may be utilized to provide branding, background color, and/or package information on the package. The use of adhesives, coatings and/or colorants, are discussed in additional detail hereafter.

We now turn our focus to the recyclability of the packages of the present disclosure. The recycling process can determine the percent of recyclable material and also the amount of reject material, i.e. the amount of material which is not recyclable. Some specific examples of standards which may be useful in determining whether package material and/or the package is recyclable, the percent recyclable material, and the percent of non-recyclable material, include the PTS method and Western Michigan method, and each is described below in additional detail. These methods pertain to the recyclability of materials which comprise wood fibers and/or pulp fibers. These methods are discussed in additional detail hereafter.

Package materials of the present disclosure may comprise natural fibers which form a paper. The package material may comprise at least 50 percent by weight natural fibers, at least 70 percent by weight natural fibers, or at least 90 percent by weight natural fibers. As yet another example, the package material may comprise 95 percent by weight natural fibers. The package materials of the present disclosure may comprise between 50 percent by weight to 100 percent by weight natural fibers, between 70 percent by weight to 99.9 percent by weight, or between 90 percent by weight to 99.9 percent by weight natural fibers. It is worth noting that where the weight percentage of natural fibers is less than 100 percent, there is room for coatings, colorants, barrier film layers, and/or adhesives, if desired.

In order to increase the likelihood that the package material and/or the package is recyclable, the total weight percentage of non-recyclable material, e.g. adhesives, barrier film layers, coatings and/or colorants, in the package material of the present disclosure may be carefully selected. For example, the package material and/or the package of the present disclosure may comprise 50 percent by weight or less, 30 percent by weight or less, or about 10 percent by weight or less of non-recyclable material. As another example, the package material and/or package of the present disclosure may comprise from between about 0.1 percent to about 50 percent by weight, from about 0.1 percent to about 30 percent by weight, or from about 0.1 percent to about 10 percent by weight of non-recyclable material. If increased likelihood of recyclability is desired, the weight percentage of non-recyclable materials can be 5 percent by weight or less, or between 0.1 percent to 5 percent by weight.

The effectiveness of the recycling process on the package material and/or the package of the present disclosure may be determined via recyclable percentage. Package material and/or the package of the present disclosure can exhibit recyclable percentages of 60 percent or greater, 80 percent or greater, or 90 percent or greater. The packaging material and/or the package of the present disclosure can have a recyclable percentage of between 60 percent to about 99.9 percent, from about 80 percent to about 99.9 percent, or from about 90 percent to about 99.9 percent. In one specific example, the package material and/or the package of the present disclosure may exhibit a recyclable percentage of from about 80 percent to about 90 percent, about 90 percent to about 99.9 percent, from about 94 percent to about 99.9 percent, or from about 96 percent to about 99.9 percent. The recyclable percentage of the package material or the package of the present disclosure can be determined via test PTS-RH:021/97 (Draft October 2019) under category II, as performed by Papiertechnische Stiftung located at Pirnaer Strasse 37, 01809 Heidenau, Germany.

Along with recyclable percentage, the total reject percentage can be determined via the PTS-RH:021/97 (Draft October 2019) under category II test method. However, unlike the recyclable percentage, in order to increase the likelihood of recyclability, the total reject percentage can be decreased. For example, the total reject percentage of the package material and/or the package of the present disclosure can be 40 percent or less, about 20 percent or less, or less than about 10 percent or less. For example, the total rejection percentage of the package material and/or the package of the present disclosure can be from about 0.1 percent to about 40 percent, from about 0.1 percent to about 20 percent, from about 5 percent to about 20 percent, or from about 0.1 percent to about 10 percent. In one specific example, the total reject percentage can be less than about 6 percent, or between about 5 percent and about 20 percent, between about 0.1 percent to about 6 percent, about 0.1 to about 4 percent, or about 0.1 to about 3 percent.

For the sake of clarity, the percent non-recyclable material does not necessarily have a 1:1 correlation to the total reject percentage. For example, the use of dissolvable adhesives is disclosed herein. As these adhesives are designed to dissolve during the recycling process, it is theorized that these adhesive would not have an impact on the total reject percentage; however, they would contribute to the non-recyclable material weight percent.

It is worth noting that the test method PTS-RH:021/97 (Draft October 2019) under category II, comprises a handsheet inspection component. Trained screeners inspect one or more handsheets of recycled package material and/or package for visual imperfections and tackiness. If the number of visual imperfections is too great or if too tacky, then the package material and/or the package is rejected. If the number of visual imperfections is acceptable and the handsheet is not too tacky, in accordance with the PTS-RH:021/97 (Draft October 2019) method, then the package material and/or the package is approved for additional processing. The package material and/or the package of the present disclosure can yield an acceptable level of visual imperfections and tackiness during this step of the PTS method.

The package material and/or the package of the present disclosure can yield the recyclable percentages mentioned heretofore as well as pass the handsheet screening method. So the package material and/or the package of the present disclosure can achieve an overall score or final outcome of "pass" when subjected to the PTS-RH:021/97 (Draft October 2019) under category II, recycling test method.

It is also worth noting that there is an alternative method for determining the recyclable percentage of the package material and/or the package of the present disclosure. The test method performed by the University of Western Michigan called the Repulpability Test can provide a percent yield of recyclable material. The package material and/or the package of the present disclosure can achieve a percentage yield, in accordance with the Repulpability Test, which is greater than about 60 percent, greater than about 80 percent, or greater than about 90 percent. The packaging material and/or the package of the present disclosure can have a percent yield of between 60 percent to about 99.9 percent, from about 80 percent to about 99.9 percent, or from about 90 percent to about 99.9 percent. In one specific example, the package material and/or the package of the present disclosure can exhibit a percentage yield of recyclable material which is between 80 percent and 99.9 percent. In such example, the package material and/or the package may comprise a base color of brown. In another specific example, the package material and/or the package of the present disclosure can exhibit a percentage yield of recyclable material which is between 85 percent and 99.9 percent. In such example, the package material may comprise a base color of white. Base colors of package materials are discussed in additional detail herein.

It is contemplated that the package material and/or the package of the present disclosure, while being recyclable, may itself comprise recycled material. Such determination can be made from a visual inspection of the package material. For example, manufacturers typically advertise the use of recycled materials in an effort to demonstrate their eco-friendly packaging approach. To further expand on this example, some manufacturers may utilize a logo, e.g. a leaf, along with wording to indicate packaging which comprises recycled material. Often times, manufacturers may specify the percentage of recycled material utilized as well, e.g. over 50 percent, over 70 percent, etc. The package material and/or the package may comprise PIR and/or PCR.

Visual inspection can be as simple as utilizing the human eye to inspect packages for logos of the use of recycled material. Additionally or alternatively, visual inspection may include microscopy methods such as optical microscopy, scanning electron microscopy or other suitable methods known in the art. For example, package material and/or package comprising recycled paper fibers could look different under a microscope due to the presence of a much wider range of natural fiber types than if the package material and/or package comprised 100% non-recycled paper. As another example, under a microscope, potentially scanning electron microscope, recycled fibers, due to their processing may appear more fibrillated than their virgin fiber counterparts.

The package material of the present disclosure can be arranged as a package in a myriad of configurations containing one or more absorbent articles. For example, the package may comprise a plurality of panels, including a consumer-facing panel. The consumer-facing panel is the face of the package, when on shelf, that faces the consumer. In general, the consumer-facing panel comprises branding and/or package information, each of which is described in additional detail herein. Each of the plurality of panels comprises an inner surface and an outer surface.

Coatings and Colorants

Each of the plurality of panels comprises an inner surface and an outer surface. The outer surface and/or inner surface of one or more panels may comprise colorants and/or coatings, which create branding on the package, package information, and/or background color, etc. The branding and/or package information can be provided on an outer surface and/or inner surface of at least one panel, e.g. the consumer-facing panel. Branding can include logos, trade names, trademarks, icons, and the like, associated with the absorbent articles within the package. Branding can be utilized to inform a consumer of the brand of the absorbent articles within the package. As an example, branding for a package of diapers ay comprise the brand name Pampers®.

Package information can include the size of the absorbent articles, the number of absorbent articles within the package, an example image of the absorbent articles contained within the package, recyclability logos, and the like, associated with the absorbent articles within the package. Additionally, package information can include information regarding the package material itself, e.g. recyclability logos, certifications from various organizations, or the like. As an example, package information for a package of feminine hygiene pads may comprise a size indicator, e.g. "Size 1." Other panels of the package may similarly include branding, package information, and/or background color, along with that associated with the consumer-facing panel.

Additionally, one or more panels of the packages of the present disclosure may comprise colorants and/or coatings, to provide a background color to the packages of the present disclosure. To further clarify the background color, it is worth noting that the packaging material comprises a base color. A base color of the package material is the color of the package material without colorants and/or coatings. For example, bleached package material is white in color, unbleached is brown in color, and package material which includes recycled content is grey in color. A background color is any color that is not a base color, e.g. blue, red, green, yellow, purple, orange, black, or combinations thereof. However, background color can also include white, brown, or grey, if the background color is achieved via colorants and/or coatings.

As noted previously, the use of colorants and/or coatings may be considered to be contaminants in the recyclability stream. So the use of colorants and/or coatings should be carefully reviewed.

In order to reduce the use of colorants and/or coatings, for the benefit of the recycling process, a base color of the package material may be utilized. For example, packages where the consumer-facing panel comprises branding, package information, and/or background color, while one or more panels comprise a base color are contemplated. In one specific example, the bottom panel and/or back panel may utilize the base color of the package material instead of a background color. One or more of the bottom panel, top panel, left panel, right panel, back panel, or any combination thereof may utilize the package material base color instead of a background color. In another example, the consumer-facing panel independently or in conjunction with other panels may comprise a base color. To further build on this example, the package may comprise absorbent articles which comprise natural-based components, e.g. cotton topsheet and/or non-chlorine bleached pulp in an absorbent core. In such examples, the consumer-facing panel may comprise a base color of white. In this same example, in conjunction with the base color, the consumer-facing panel may further comprise branding, background color (associated with the branding), and/or package information. In still another example, one or more panels may comprise package information, which in part, comprises a base color. To further build on this example, the base color may be a first color, e.g. white, and a background color may be applied to a panel with a negative image of the package information, such that the package information, or a portion thereof, is not covered by the background color, and the package information comprises the first color.

Still in other examples, the seams of the packages of the present disclosure may comprise less colorant coverage than adjacent areas on the same panel. For example, a portion of a panel which is joined to another portion of the panel to form a seal, may comprise a seam area. The seam area may comprise less colorant or even no colorant than the portion of the panel adjacent thereto. Each seal may comprise a seam area which comprises less colorant or even no colorant than an adjacent area to the seal.

Still in other examples, a first panel may comprise a colorant percent coverage which is different than a second panel. Further elucidating this example, the consumer-facing panel may have a colorant percent coverage which is higher than another panel of the package, e.g. bottom panel. As noted, absorbent articles which are natural based, e.g. cotton topsheets or other components, non-chlorine bleached cores, no added colorants, and/or no added scents, may rely more on the base colors of the package material. As an example, such packages may comprise a consumer-facing panel comprising a colorant coverage of 75 percent or less, 50 percent or less, or 40 percent or less. Further the consumer-facing panel may comprise a colorant coverage of from between about 10 percent to about 75 percent, from about 15 percent to about 50 percent, or from about 20 percent to about 40 percent.

In such packages other panels may be configured having a higher percentage of colorant coverage, lower percentage, or a mix thereof. For example, in such configurations, a bottom panel may comprise a lower percentage of colorant coverage. A back panel, left panel, and/or right panel may comprise a higher percent colorant coverage percentage or a lower percentage of colorant coverage. These same values may apply for flow wrap package configurations described herein as well.

Natural based products as described are not necessarily limited to the foregoing colorant coverages; however, less colorant percentage can mean less colorant weight percentage which can be beneficial from a recyclability standpoint. In another example, absorbent article packaging in accordance with the present disclosure may comprise a consumer-facing panel having a colorant coverage of 100 percent, 99 percent or less, or 98 percent or less. For example, packages in accordance with the present disclosure may comprise a consumer-facing panel having a colorant coverage percentage of from between about 40 percent to about 100 percent, about 60 percent to about 100 percent, from about 60 percent to about 99 percent, or from about 60 percent to about 98 percent. In such configurations, other panels may comprise the same percentage of colorant coverage or may comprise a lower percent of colorant coverage. Colorant coverage percentage is determined via the Percentage of Colorant Coverage Measurement Method described herein.

It is worth nothing that careful selection of the paper may be required to achieve the desired recyclability percentage. For example, the inventors have surprisingly found that while the colorants and/or coating can play a very minor role in the overall weight percentage of the package material, the colorants and/or coatings, do form a portion of the overall percentage. Accordingly, where the desired recyclability percentage is 95 percent or greater, it may be advisable to utilize a package material having a white base color. Where packaging material having a white base color is utilized, the amount of colorant and/or coating may be reduced as the absorbent article manufacturer may be able to utilize the base color in the overall packaging color scheme. Such executions of packaging may be useful for absorbent articles comprising cotton components and/or other natural components. Where recyclability percentages desired are less than 95 percent, then any suitable base color may be utilized.

While any suitable colorants may be utilized, the inventors have surprisingly found that water based colorants typically dissolve more readily in water during the recycling process. So, water based colorants can facilitate the recycling process for the packages of the present disclosure. Any suitable water based colorant may be utilized. Water based colorants are well known in the art.

It is worth noting that solvent based colorants and/or energy curable colorants may also be utilized. However, the use of these types of colorants can add complication to the manufacturing of the package material. For example, solvent based colorants generally exhaust volatile organic compounds which are required to be removed from the air. Additionally, solvent based colorants may comprise components which do not readily dissolve in water during the recycling process which could negatively impact the recyclability of the package material and/or package.

Energy curable colorants may also be utilized; however, much like the solvent based colorants, energy curable colorants can add complication to the processing of the package material. And much like the solvent based colorants, the energy curable colorants may comprise components which are not readily dissolvable in water during the recycling process which could negatively impact the recyclability of the package material and/or the package.

Any suitable coating on an outside surface of the package material (i.e., opposite the one or more barrier film layers on the inside surface) may be utilized. Coatings can be utilized to protect the background color, branding, and/or package information. Additionally, coatings may be utilized to provide anti-static benefits, coefficient of friction benefits, and/or appearance benefits, e.g. gloss, matte, satin, high gloss, etc.) Much like water based colorants, the inventors have surprisingly found that water based coatings, if utilized, may facilitate the recycling process of the package material and/or the package. Suitable coatings comprise varnishes which are well known in the art. Any suitable coating/varnish may be utilized.

Package Seals

As noted previously, packages of the present disclosure may also comprise a plurality of seals. Seals are package material seams which have been attached to one another. Scams are areas of the package where at least two portions of the package material have the ability to overlap one another. Seals are created when the at least two portions of the package material in the seam are joined to one another. For example, a consumer facing panel be joined to a back panel via seals. One or more polymer or polyolefins, such as polyethylene, or an adhesive may be provided on an interior surface of a first portion of the consumer facing panel and an interior surface of the back panel to create one or more seals. The polymer or polyolefin may be at least partially melted in an area desired for the seal to form the seal. While the seals may be provided on any panel of the package, it is recommended that a consumer-facing panel not include seams or seals. Seams and seals can be visibly non-appealing for consumers.

It is worth noting that seams may comprise overlap areas of package material as described heretofore. Namely, one or more polymers, polyolefins, or adhesives may be applied on an inner surface of a first portion of the package material and/or an outer surface of a second portion of the package material. The first portion and the second portion can then be joined together to create an overlap seal. However, butt seals may also be created. Butt seals can be created where one or more polymers, polyolefins, or adhesives is applied to the inner surface of a first portion of the package material and/or the inner surface of a second portion of the package material. The inner surfaces of the first portion and the second portion may be joined to form a butt seal. Butt seals and overlap seals are discussed in additional detail hereafter. Where the one or more barrier film layers is/are polyethylene, seals may be created via heat sealing the film layer to itself with or without the use of adhesive The seals are important to ensure that the packages of the present disclosure have a reduced likelihood of exposure of the one or more absorbent articles therein to the environment outside of the package material. The use of seals, as described herein, can provide adequate sealing of the package material such that absorbent articles within the package are not exposed to the exterior environment. Simply folding or rolling of the package material does not form a seal and is not generally sufficient to protect the one or more absorbent articles therein from the external environment.

In order to survive the rigors of the shipping, stocking, and handling by the consumer, the seals should have a requisite strength. Complicating the requirement for the requisite seal strength are a few variables, i.e. the type of seal and the level of compression of the one or more absorbent articles within the package. An additional complication is that the one or more polyolefins or adhesives are considered non-recyclable material. However, the inventors have surprisingly found that with careful selection of the type of polymers, polyolefins, or adhesives as well as the weight percentage, the seal strength requirements can be met along with maintaining the recyclability of the package material.

Regarding the types of seals, the plurality of seals of the packages of the present disclosure may comprise an access seal, a gusset seal, a hoop seal, and a bottom seal. Flow wrap packages may be configured to comprise these seals as well. Or, the flow wrap packages may comprise a pair of opposing end seals and a hoop seal between the end seals. In this configuration, an access seal may similarly be provided.

The access seal may be provided as a seal which is opened by the consumer to access the one or more absorbent articles within the package. Access seals are described in additional detail in U.S. Patent Application Publication No. 2022/0110801, published on Apr. 14, 2022, entitled "Absorbent Article Packages with Natural Fibers and Opening Features."

Packages of the present disclosure may be configured such that the seals comprise similar tensile strengths. For example, each of the plurality of seals can have a tensile strength of at least 5.1N/15 mm. In such forms, each of the seals can have a tensile strength which is within 15% of the tensile strength of the remainder of the seals of the package. However, as noted previously, since polymers, polyolefins or adhesives are considered non-recyclable material, their use should be carefully reviewed to ensure that the package material and/or the package maintains its ability to be recycled. The tensile strengths of the seals mentioned herein can be determined by the tensile test method described in ASTM F88-06 as modified herein.

As was noted previously, where present, the type as well as amount of adhesive utilized for the seals of the packages of the present disclosure can impact the recyclability of the package. As an example, polyolefins or adhesives which can dissolve or disperse in water during the re-pulping stage of the disintegration step of the recycling process may be particularly suitable for the packages of the present disclosure. Such adhesives include starch based adhesives, polyvinyl alcohol based adhesives, and polyethylene oxide based adhesives. One suitable example of a starch based adhesive is available from LD Davis located in Monroe, North Carolina, under the trade name AP0420CR. One suitable example, of a polyvinyl alcohol based adhesive is available from Sekisui Chemical Company, located in Osaka, Japan, under the trade name Selvol 205. One suitable example of a polyethylene oxide based adhesive is available from Dow Chemicals Co. located in Midland, Michigan, under the trade name WSR N-80.

If the adhesive is not water-soluble, then water-dispersible adhesives may similarly be utilized. Suitable examples of water dispersible adhesives include thermoplastic elastomer based adhesives and polyvinyl acetate based adhesives. One suitable example of a thermoplastic elastomer based adhesive is available from Actega located in Blue Ash, Ohio, under the trade name Yunior 491. One suitable example of a polyvinyl acetate based adhesive is available from Bostik located in Milwaukee, Wisconsin, under the trade name Aquagrip 4419U01. Another suitable example of a polyvinyl acetate based adhesive is available from HB Fuller under the trade name PD-0330.

Any suitable pressure sensitive adhesives may be utilized as well. One suitable example of a pressure sensitive adhesives includes sold by Formulated Polymer Products Ltd. Located in Bury, Lancashire, England, and sold under the trade name FP2154. As one specific example, the access seal may comprise a pressure sensitive adhesive.

Without wishing to be bound by theory, it is believed that packages of the present disclosure which utilize adhesives dissolvable in water may comprise a higher weight percentage of such adhesives than adhesives which are only water dispersible. For example, packages comprising water dissolvable adhesives may comprise a first weight percentage of adhesive while packages comprising water dispersible adhesives may comprise a second weight percentage of adhesive. It is believed that the first weight percentage may be greater than the second weight percentage for the purposes of recycling the package material and/or the package.

As noted previously, the packages of the present disclosure may utilize a dissolvable adhesive, dispersible adhesive, pressure sensitive adhesive, or any combination thereof. However, the choice of adhesives should be considered carefully from a weight percentage standpoint. Where dissolvable adhesives are utilized, the adhesive may comprise at least one of the following: starch based, polyethylene oxide based, polyvinyl alcohol based, or combinations thereof.

It is worth noting that the characteristics of the seals of the packages of the present disclosure may depend on how the package material is processed. For example, an absorbent article manufacturer may purchase the package pre-formed. In such instances, the absorbent article manufacturer may receive from a paper package manufacturer essentially an open bag comprising a consumer-facing panel and a back panel having side seals.

It is also possible that the absorbent article manufacturer produces the packages themselves. For example, an absorbent article manufacturer may have the capability to produce the open bag, similar to above and subsequently fill it with one or more absorbent articles and thereafter seal it without the need for purchasing such bags from a supplier.

It is worth noting that adhesive may be utilized for additional reasons. For example, where the feature of resealability is desired, an adhesive may be provided near an access seal area to allow for resealability of the package. The ability to reclose the package can help to protect the articles within the package from contamination of the external environment and also inhibit moisture from the environment from being absorbed by the articles in the package. One suitable example of an adhesive which can be utilized is a pressure sensitive adhesive. One specific example of a pressure sensitive adhesive is available from Bostik and sold under the trade name Aquagrip® JB018. Additionally, the package on one or more of the plurality of panels may include instructions to the user to reseal the package when articles are not required to be accessed.

Now turning the focus to some of the mechanical properties of the package material. In order to withstand the rigors of a manufacturing process where a plurality of absorbent articles is disposed within the package, withstand the rigors of being shipped, provide protection from environmental insults during shipping and while on the store shelf, and provide for product protection while in the consumers home, the package material may have some level of strength, stretch, and resilience. As an example, package material of the present disclosure may exhibit an MD tensile strength of at least 4.7 kN/m, at least 7 kN/m, or at least 8 KN/m. The MD tensile strength may be between 4.7 kN/m to 9.0 kN/m, or between 5.2 kN/m and 8.2 kN/m, or between 5.5 kN/m and 8.0 kN/m. The MD tensile strength is measured using ISO 1924-3 as modified herein.

As another example, the package material of the present disclosure can exhibit a CD tensile strength of at least 2.7 kN/m, at least 4 kN/m, or at least 5.5 kN/m. The CD tensile strength may be between 2.7 to 6.5 kN/m, between 2.7 to 6.2 kN/m, or between 2.7 to 6 kN/m. The CD tensile strength is measured using ISO 1924-3 as modified herein.

As another example, the package material of the present disclosure can exhibit a burst strength of at least 185 kPa, at least 250 kPa, or at least 550 kPa. The burst strength of the package material of the present disclosure can be between 185 to 600 kPa, between 220 to 550 kPa, or between 250 to 500 kPa. The burst strength is measured using ISO 2758 as modified herein.

As another example, the package material of the present disclosure may exhibit an MD stretch at break, at least 3 percent, or at least 6 percent. The package material of the present disclosure can exhibit an MD stretch at break of between 3 to 6.5 percent, between 3.2 to 6.2 percent, or between 3.5 to 6 percent. The MD stretch at break is measured using ISO 1924-3 as modified herein.

As another example, the package material of the present disclosure can exhibit a CD stretch at break of at least 4 percent, at least 6 percent, or at least 9 percent. The package material of the present disclosure can exhibit a CD stretch at break of from 4 to 10 percent, from 4.5 to 9.5 percent, or from 5 to 9 percent. The CD stretch at break is measured using ISO 1924-3 as modified herein.

Regarding caliper, the package material of the present disclosure can exhibit caliper of at least 50 μm, at least 70 μm, or at least 90 μm. The package material of the present disclosure can exhibit caliper of between 50 to 120 μm, from 55 to 115 μm, or from 60 to 110 μm. The caliper is measured using ISO 534 as modified herein.

It is worth noting that the package material of the present disclosure is different than cartonboard, cardboard, and brown paper bags. For example, cartonboard is not as flexible as the package materials of the present disclosure. Cartonboard is designed and is inherently stiffer than the package materials of the present disclosure and can be more difficult to process on converting lines due to their stiffness. Additionally, cartonboard has a higher basis weight than do the package materials of the present disclosure.

Similarly, cardboard is also different than the package materials of the present disclosure. Cardboard has a much higher basis weight than the package materials of the present disclosure. Additionally, cardboard is much less flexible than the package materials of the present disclosure. Cardboard materials are commonly fluted and comprise three plies of a paper material and as such, is structurally different than the package materials of the present disclosure. Additionally, the package material of the present disclosure has a much lower basis weight than does cardboard.

Some advantages that the packaging material of the present disclosure have over cartonboard and cardboard include the flexibility as discussed herein. However, another advantage is that the package materials of the present disclosure take up less space than their more-bulky cartonboard and cardboard counterparts. Another advantage of the package materials of the present disclosure is that they allow the absorbent articles therein to be compressed within the package. This allows for more products to fit within a smaller volume package which also enable efficiency.

Regarding brown paper bags which were prevalent in grocery stores for carrying groceries, the packages of the present disclosure are also different. As discussed in additional detail herein, the package material of the present disclosure is polymer, polyolefin and/or adhesive sealed such that the absorbent articles are completely enclosed and protected from the external environment by the package material. More specifically, the package of absorbent articles in accordance with the present disclosure does not have an opening into which items can be placed. Instead, the package of absorbent articles in accordance with the present disclosure is sealed to reduce the likelihood of contamination of the absorbent articles during shipping, stocking, and sitting on store shelves. In contrast, the conventional brown paper bags widely used in grocery stores decades ago, comprise an opening into which items can be placed. Additionally, these brown paper bags do not offer any barrier to moisture vapor absorption.

Despite having reduced flexibility compared to plastic packaging and lower basis weight than cardboard and cartonboard, the inventors have surprisingly found the packaging material of the present disclosure can withstand the rigors of a manufacturing process where a plurality of absorbent articles is placed within the package as well as the rigors of being shipped, provide protection from environmental insults during shipping, and while on the store shelf, and provide for product protection while in the consumers home.

In addition, examples are contemplated where the absorbent article backsheet is in direct contact with the inner surface of the package material. Packages of the present disclosure comprising diapers may be configured in this manner. Feminine hygiene pads, including menstrual pads, liners, adult incontinence pads, and the like, may be individually wrapped in order to protect panty fastening adhesive on their respective backsheets. In packages with these articles, the individually wrapped article may be in direct contact with the inner surface of the package material. Forms are contemplated where the wrapper which wraps the individual articles may comprise natural fibers as described herein. Additionally, such wrappers may be recyclable as described herein.

As noted previously, absorbent article manufacturers may purchase the packaging material already preformed into open bags or may purchase rolls of packaging material. Regardless of whether the package material is on rolls or pre-formed to some extent, the packages of the present disclosure begin with paper stock.

In one example, FIG. 1A details the various layers a package material may comprise. A package material 10 may comprise natural fibers 12 that may comprise wood fibers or pulp fibers. The package material 10 may have an interior side 14 (facing absorbent articles (indicated as AA) within the package) and an exterior side 16 (facing away from the absorbent articles within the package). The package material 10 may comprise a first barrier film layer 18. The first barrier film layer 18 may comprise a polymer or a polyolefin, such as a low density polyethylene, for example. The low density polyethylene acts as a sealant and a barrier to atmospheric moisture. The natural fibers 12 may have a basis weight in the range of about 60 gsm to about 100 gsm, about 70 gsm to about 90 gsm, or about 80 gsm. The first barrier film layer 18 may have a basis weight in the range of about 10 gsm to about 18 gsm, about 12 gsm to about 16 gsm, or about 14 gsm. The first barrier film layer 18 may be in direct contact with the natural fibers 12 on the interior side 14 of the package 10. A portion of an exterior side 16 of the package material in the top panel may comprise a heat sealable lacquer 22 in dedicated areas to enable an exterior side 16 of the package to seal to an exterior side 16 of the package when forming a gusset seal in the top panel. The package material 10 may be free of adhesives or may include adhesives.

Figure 1B:
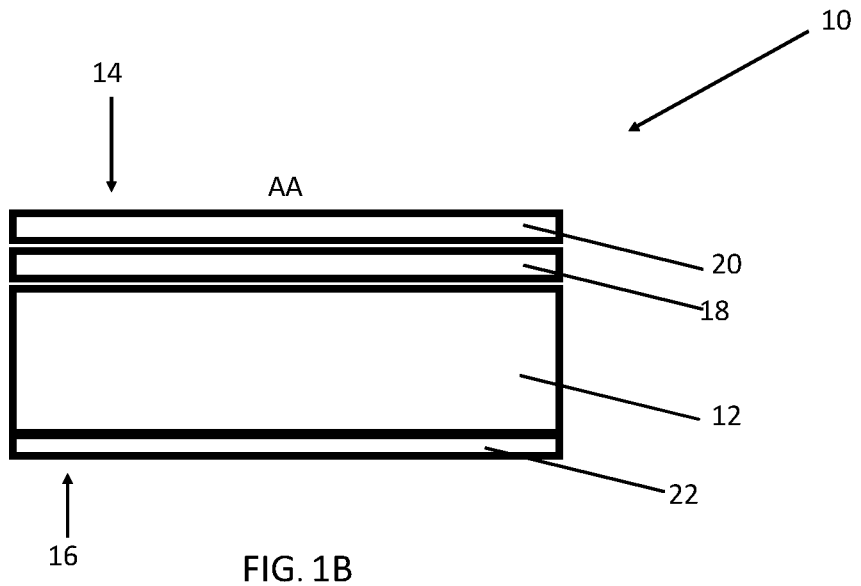
FIG. 1B is a schematic representation of a portion of a package material in accordance with the present disclosure.

In another example, FIG. 1B details the various layers a package material may comprise. A package material 10 may comprise natural fibers 12 that may comprise wood fibers or pulp fibers. The package material 10 may have an interior side 14 (facing absorbent articles (indicated as AA) within the package) and an exterior side 16 (facing away from the absorbent articles within the package). The package material 10 may comprise a first barrier film layer 18 and a second barrier film layer 20. The package material may also comprise a third barrier film layer, if desired. The first barrier film layer 18 may comprise a polymer or a polyolefin and the second barrier film layer 20 may comprise the same polymer or polyolefin or a different polymer or polyolefin. As one example, the polyolefin of the first barrier film layer 18 may comprise, consist essentially of, or consist of, high density polyethylene and the second polyolefin of the second barrier film layer 20 may comprise low density polyethylene. While not wishing to be bound by theory, the inventors have found that the low density polyethylene acts as sealant and a highly effective barrier to atmospheric moisture while the high density polyethylene acts as an effective barrier to atmospheric moisture. The first barrier film layer 18 may be in direct contact with the natural fibers 12. The second barrier film layer 20 may not be in contact the natural fibers or may have less contact with the natural fibers 12 compared to the first barrier film layer 18. If the first and second barrier film layers are desired, they may be co-extruded onto the natural fibers 12, or otherwise applied to the natural fibers. The natural fibers 12 may have a basis weight in the range of about 60 gsm to about 100 gsm, about 70 gsm to about 90 gsm, or about 80 gsm. The first barrier film layer 18 may have a basis weight in the range of about 3 gsm to about 15 gsm, about 4 gsm to about 12 gsm, about 5 gsm, or about 10 gsm. The second barrier film layer 20 may have a basis weight in the range of about 3 gsm to about 10 gsm, about 4 gsm to about 8 gsm, about 5 gsm to about 7 gsm, or about 6 gsm. A portion of an exterior side 16 of the package material in the top panel may comprise a heat sealable lacquer 22 to enable an exterior side 16 of the package to seal to an exterior side 16 of the package when forming a gusset seal in the top panel. The package material 10 may be free of adhesives or may include adhesives.

The inventors have found that by providing either a high level (e.g., 14 gsm) of a first barrier film layer 18 (LDPE) without a second barrier film layer 20 or a smaller level (e.g., 5 gsm or 10 gsm) of a first barrier film layer 18 (HDPE) with a second barrier film layer 20 (LDPE) of about 6 gsm, they can achieve a very high HuBa factor. The HuBa value corresponds to the shelf life in months of the package without the absorbent articles within the package being infiltrated with atmospheric moisture.

Figure 2A:
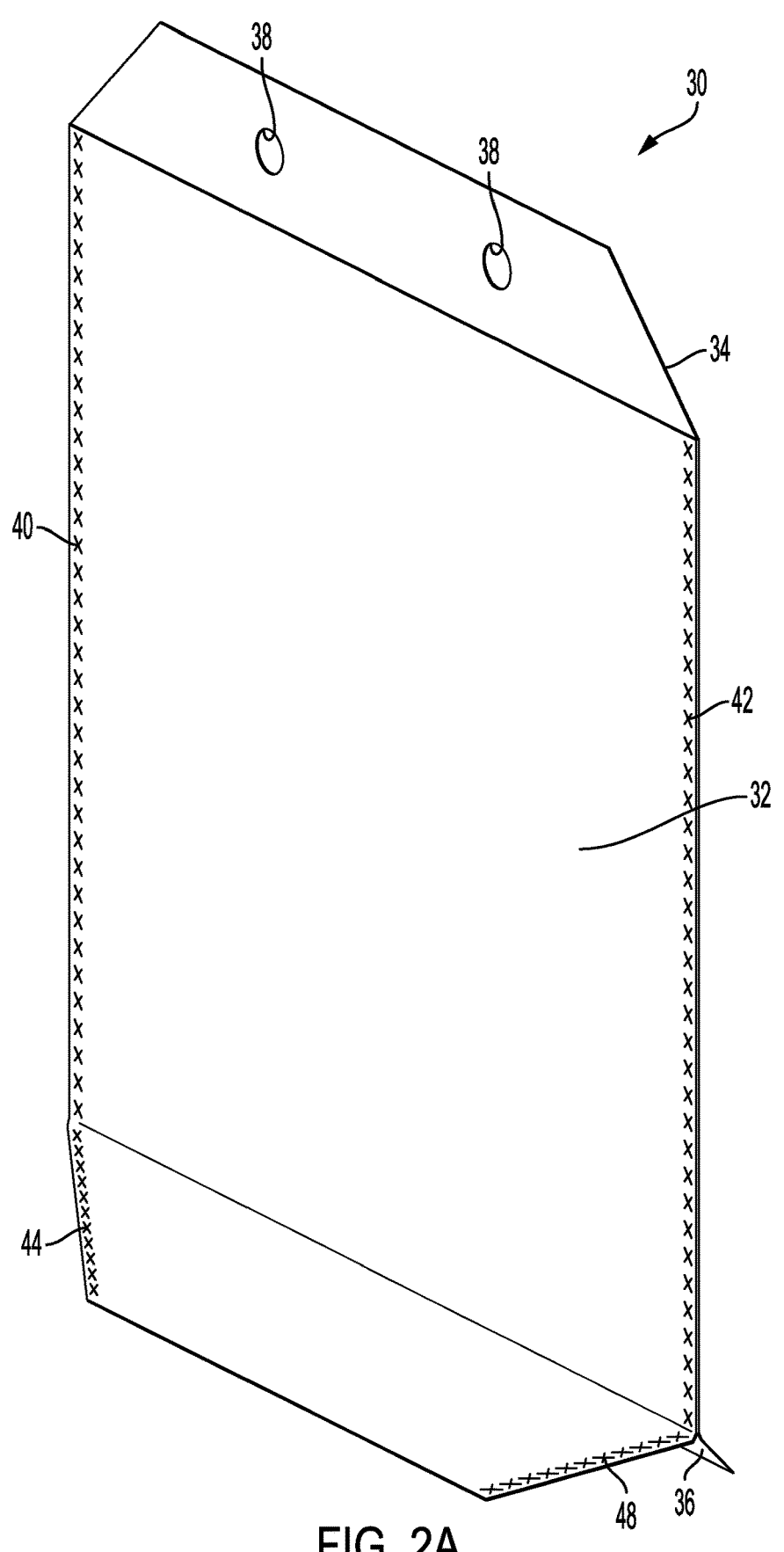
FIG. 2A is a perspective view of a package of the present disclosure in a partially flattened configuration and without one or more absorbent articles within the package.
Figure 2B:
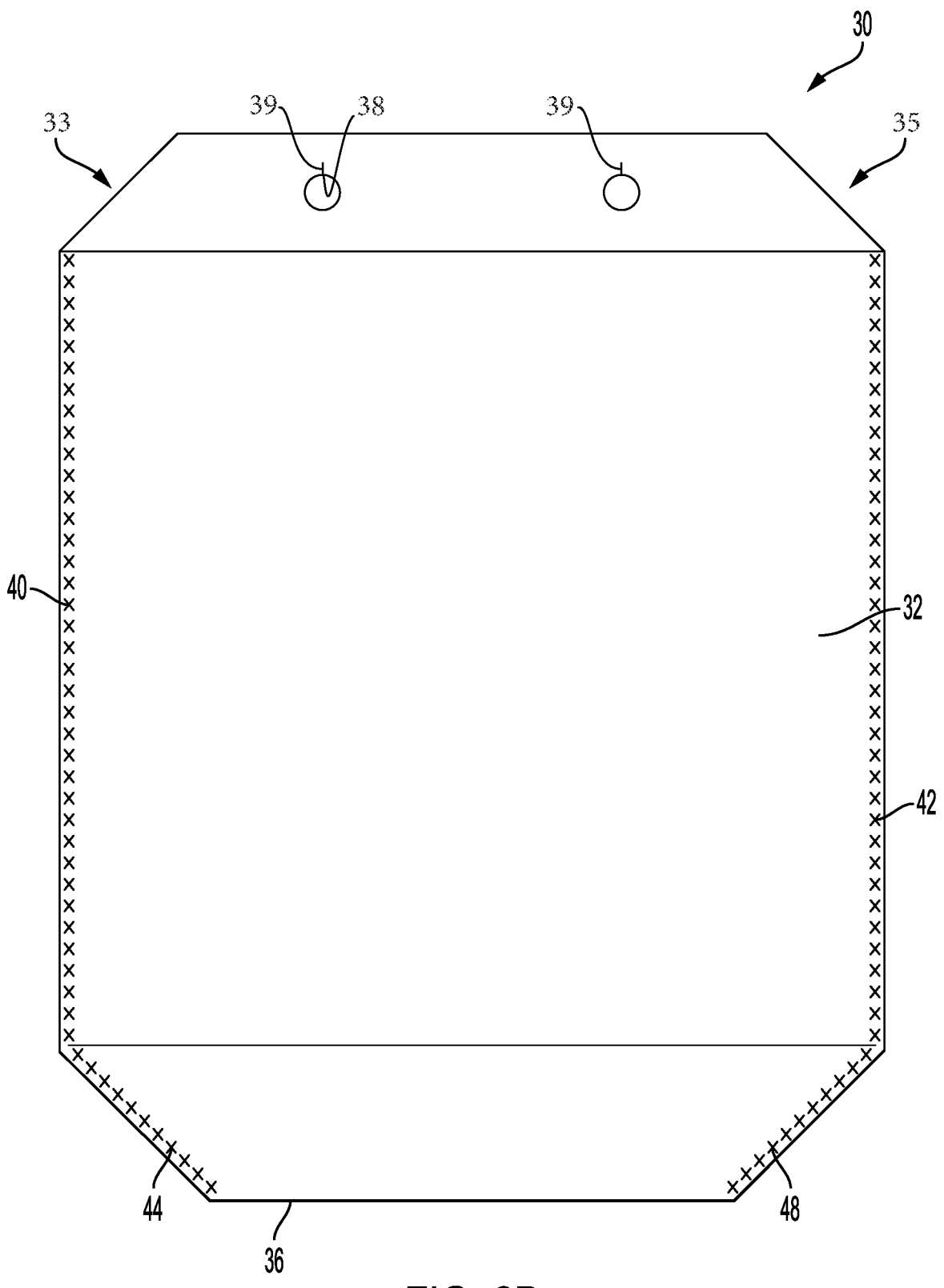
FIG. 2B is a front view of the package of FIG. 2A.
Figure 2C:
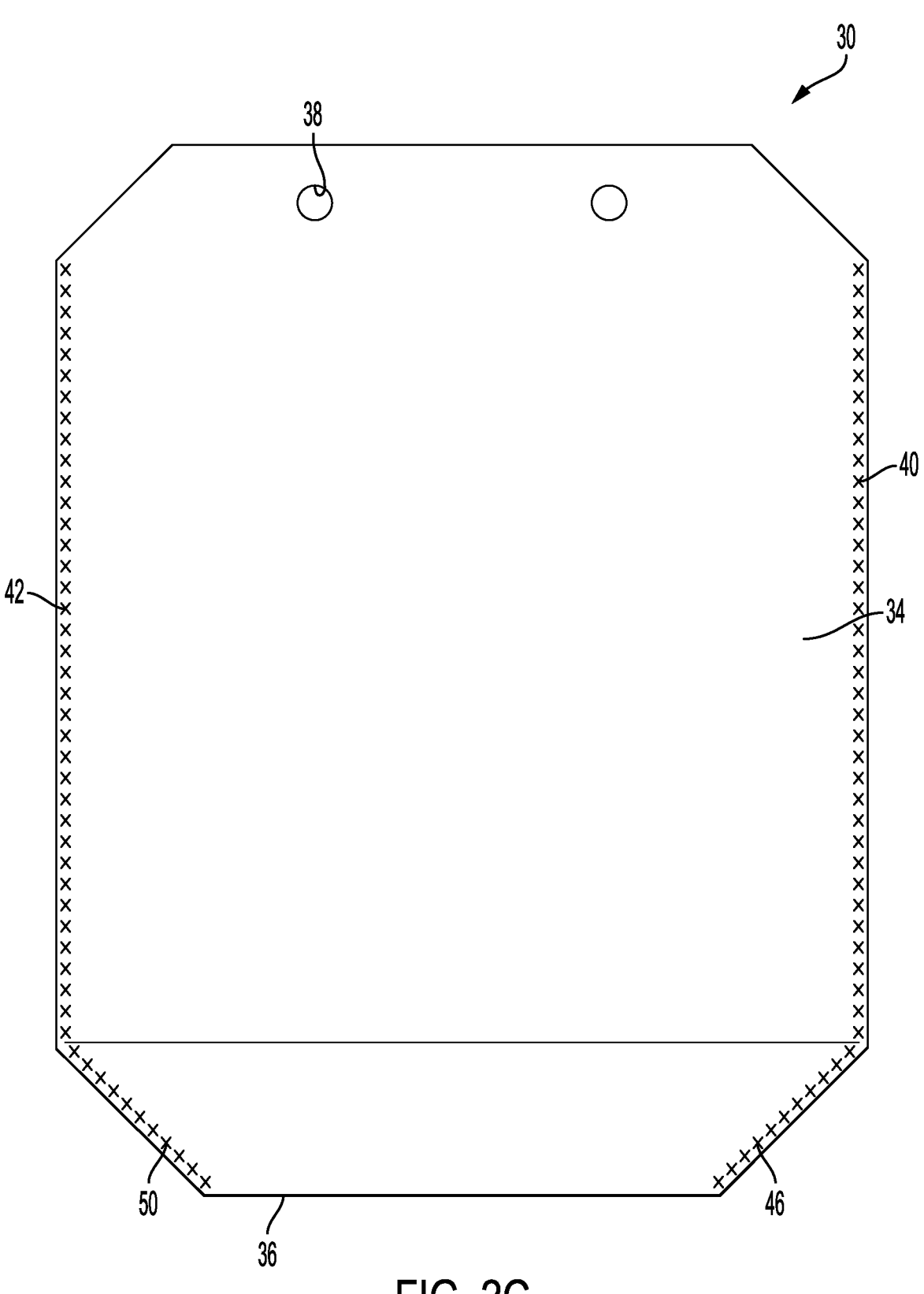
FIG. 2C is a back view of the package of FIG. 2A.
Figure 2D:
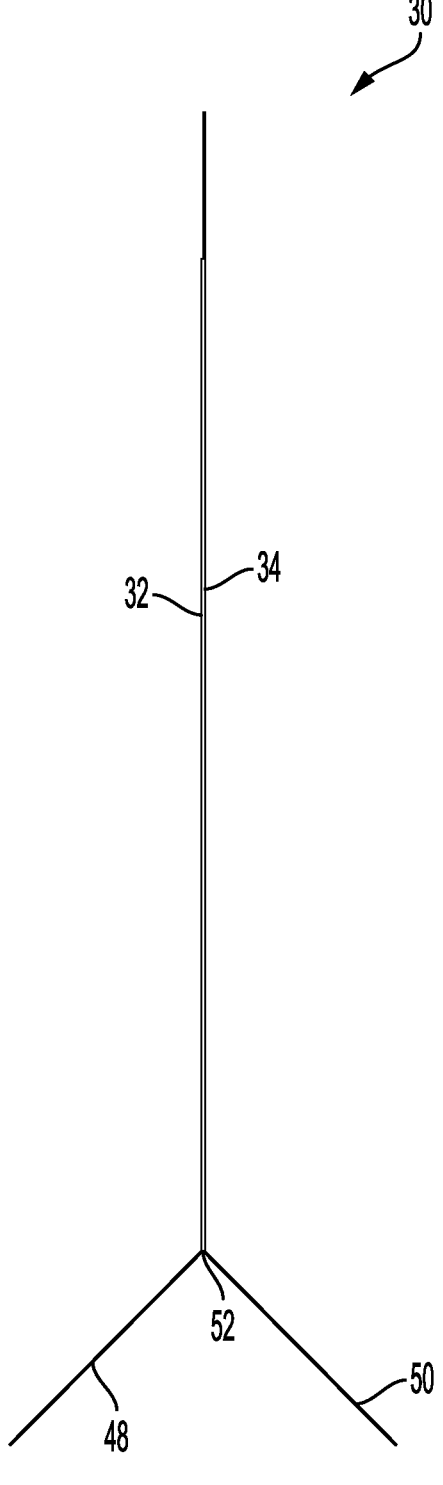
FIG. 2D is right side view of the package of FIG. 2A, with the left side view being identical.
Figure 2E:
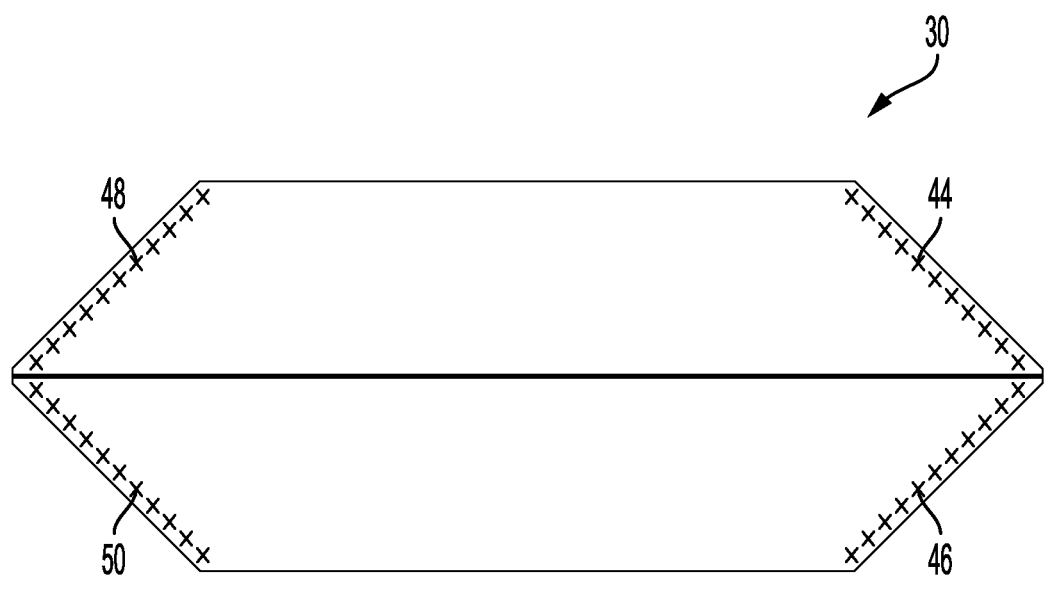
FIG. 2E is a top view of the package of FIG. 2A.
Figure 2F:
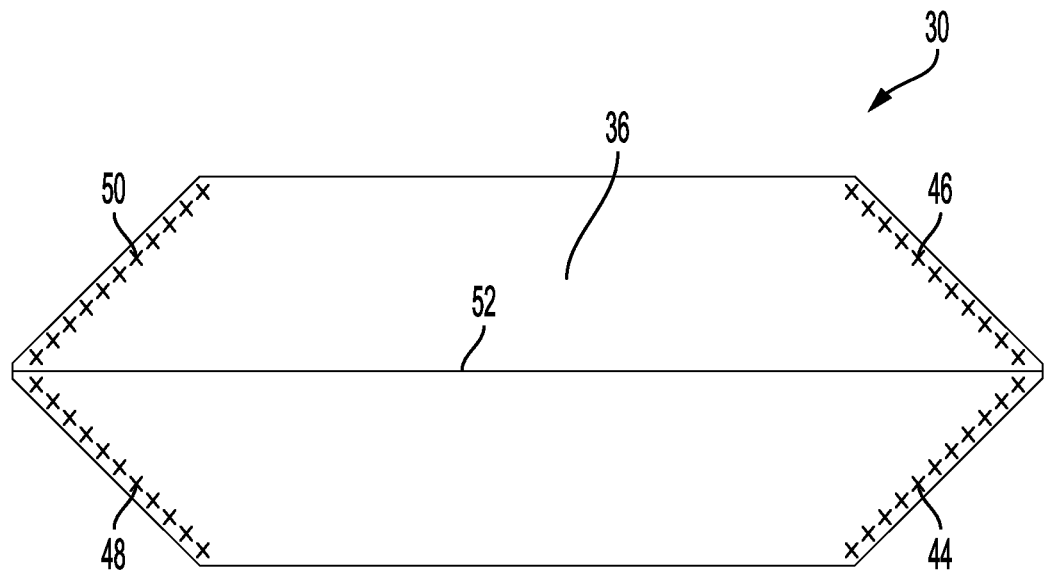
FIG. 2F is a bottom view of the package of FIG. 2A.
Figure 2G:
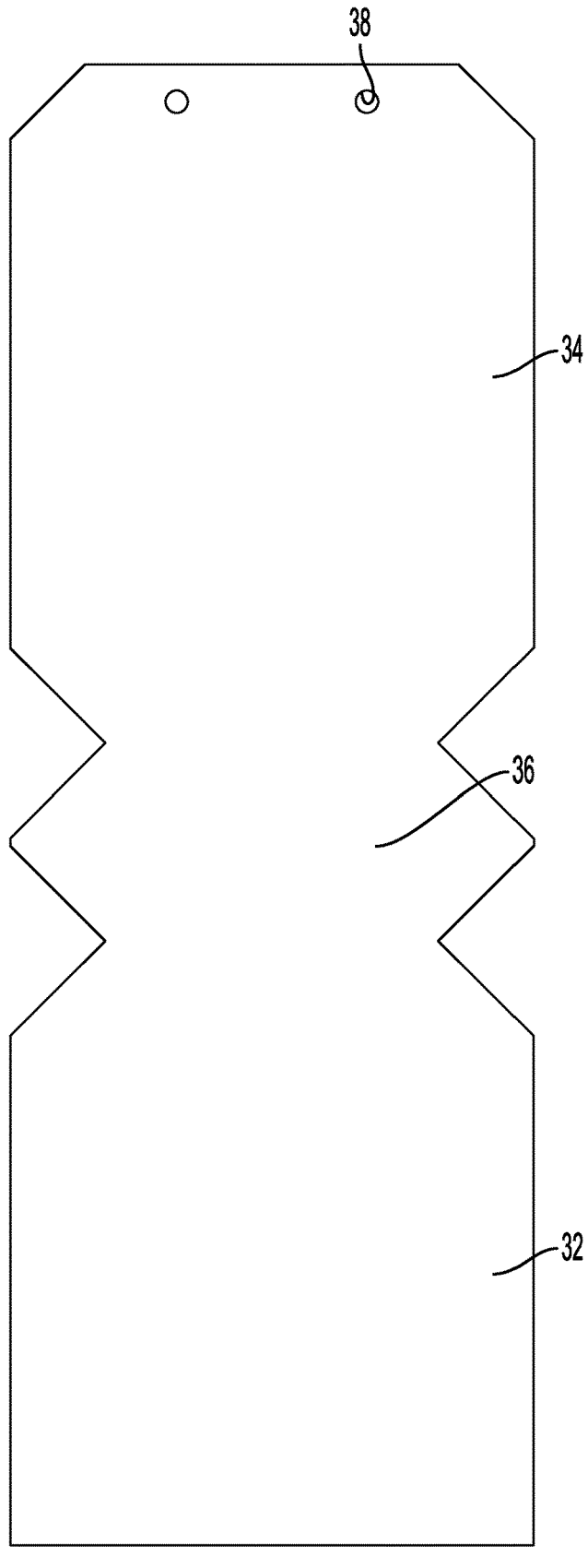
FIG. 2G is a view of a shape of the packaging material used to produce the package of FIG. 2A.

Prior to adding one or more absorbent articles an example flattened package of the present disclosure is disclosed. The package may have the configuration illustrated in FIGS. 2A-2F. FIG. 2A is a perspective view of a package of the present disclosure in a partially flattened configuration and without one or more absorbent articles within the package. FIG. 2B is a front view of the package of FIG. 2A. FIG. 2C is a back view of the package of FIG. 2A. FIG. 2D is right side view of the package of FIG. 2A, with the left side view being identical. FIG. 2E is a top view of the package of FIG. 2A. FIG. 2F is a bottom view of the package of FIG. 2A. FIG. 2G is a view of a shape of the packaging material used to produce the package of FIG. 2A.

Referring to FIGS. 2A-2F, the package 30 may comprise a consumer-facing panel 32, a back panel 34, a left side panel and a right side panel (that are only formed when absorbent articles are within the package), a bottom panel 36, and a first top panel and a second top panel (that are formed when absorbent articles are within the package 30 and the package is sealed). Portions of the consumer-facing panel 32 and the back panel 34 will eventually form the left and right side panels and the first and second top panels when the package is filled with absorbent articles. The back panel 34 may have a first chamfered left side edge 33 and a second chamfered right side edge 35 proximate to a portion of the back panel 34 containing one or more wicket holes 38 (see FIG. 2B). Having the chamfered side edges 33, 35 may improve the processing of the package 30 on a manufacturing line. Upon information and belief, processing of the package 30 on a manufacturing line without the chamfered side edges 33, 35 may create defects in the package and/or create runnability issues. The wicket holes 38 may be round or ovate or have another suitable shape.

Referring to FIG. 2B, one or more slits 39 or lines of perforation may extend from the wicket holes 38. The slits 39 or lines of perforation may extend in any suitable direction and may have a length in the range of about 1 mm to about 10 mm, about 2 mm to about 7 mm, about 2 mm to about 4 mm, about 2 mm, about 3 mm, or about 4 mm. The one or more slits 39 or lines of perforation help to induce a dedicated direction the material proximate to the wicket holes tears once the package is pulled away from the wicket. Without the one or more slits 39 or lines of perforation, forces of pulling the package from the wicket might be too high and could induce wear out of equipment. In some instances, the slits 39 or lines of perforation help the package material tear above the wicket holes 38 in a generally vertical direction and not tear in a horizontal direction. In some instances, the orientation of the fibers of the package material is generally in a horizontal direction, hence the need for a slit or line of perforation in a vertical direction to encourage vertical tearing instead of horizontal tearing. For purposes of clarity, one or more slits 39 or lines of perforation may extend from a single wicket hole 38. The slits 39 or lines of perforation may extend fully through the material of the package or partially through the material of the package. In an example, the slits 39 may extend in a vertical direction from an outer perimeter of the wicket holes (at 12 o'clock) a distance of about 3 mm. Score lines may also be used in the same manner as described herein with respect to the slits or lines of perforations.

The package 30 may be designed to have two wicket holes 38. At times, there may be one wicket hole or more than two wicket holes. In an instance, a single wicket hole may form an elongated hole. The portion of the package 30 having the wicket holes 38 may be cutaway when the package is sealed. As such, consumers will not see the wicket holes 38. In other instances, the package may be wicketless (i.e., not have one or more wicket holes). The package may comprise graphics, brand names, manufacturer information, instructions, and/or product information regarding the one or more absorbent articles positioned within the package.

The consumer-facing panel 32, the bottom panel 36, the back panel 34, and the first and second top panels may be formed of a continuous material. The continuous material may comprise natural fibers and one or more barrier film layers, as discussed with respect to FIGS. 1A and 1B. The natural fibers may form at least a portion of the outer surface of the package. A portion of the natural fibers in the top panel may comprise a heat scalable lacquer on their outermost surface which would form the outermost surface of the package. The heat sealable lacquer is for creating a gusset seal in the top panel and bonded an exterior surface of the top panel to an exterior surface of the top panel. The one or more barrier film layers may form the innermost surface of the package (i.e., the surface facing the absorbent articles), such that seals or seams may be created in the package. The one or more barrier film layers may comprise a polymer and/or a polyolefin. The polymers and/or polyolefins are capable of scaling or being seamed to each other to form seals or scams that join innermost surfaces of the package to innermost or outermost surfaces of the package. Typically, the seams or seals are formed using thermal energy and pressure, but may be formed in other ways, such as by ultrasonics, for example. A vertical left side seam 40 is formed at the location shown in FIGS. 2A-2C. The vertical left side seam 40, although illustrated in FIGS. 2A-2C as on the consumer-facing panel 32 and the back panel 34 will be on the left side panel when one or more absorbent articles are added to the package. A vertical right side seam 42 is formed at the location shown in FIGS. 2A-2C. The vertical right side seam 42, although illustrated in FIGS. 2A-2C as on the consumer-facing panel 32 and the back panel 34 will be on the right side panel when one or more absorbent articles are added to the package. A first left side angled seam 44 is formed between portions of the consumer-facing panel 32 and portions of the bottom panel 36. A second left side angled seam 46 is formed between portions of the back panel 34 and portions of the bottom panel 36. A first right side angled seam 48 is formed between portions of the consumer-facing panel 32 and portions of the bottom panel 36. A second right side angled seam 50 is formed between portions of the back panel 34 and portions of the bottom panel 36. When the package is filled with one or more absorbent articles, the angled seams 44 and 46 may be formed on the left side panel and the angled seams 48 and 50 may be formed on the right side panel. Any of the seals or seams may form overlap seams and/or butt seams as described herein. The various vertical and angled seams discussed herein may have a width in the range of about 2 mm to about 15 mm, about 3 mm to about 10 mm, about 4 mm to about 8 mm, about 4 mm, about 5 mm, about 6 mm, or about 7 mm.

The first left side angled seam 44 and the second left side angled seam 46 may each extend at an angle in the range of about 30 degrees to about 60 degrees, about 40 degrees to about 50 degrees, or about 45 degrees, relative to a longitudinal direction of extension of the vertical left side seam 40. The first right side angled seam 48 and the second right side angled seam 50 may each extend at an angle in the range of about 30 degrees to about 60 degrees, about 40 degrees to about 50 degrees, or about 45 degrees, relative to a longitudinal direction of extension of the vertical right side seam 42.

The vertical left side seam 40 may have a first length. The first left side angled seam 44 may have a second length. The second left side angled seam 46 may also have the same second length. The first length may be greater than the second length. In some instances, the first length may be at least twice as large as, three times as large as, or seven times as large as the second length. The vertical right side seam 42 may have a first length. The first right side angled seam 48 may have a second length. The second right side angled seam 50 may also have the same second length. The first length may be greater than the second length. In some instances, the first length may be at least twice as large as, three times as large as, or seven times as large as the second length. When the package is filled with one or more absorbent articles, the consumer-facing panel 32, the bottom panel 36, and the back panel 34 may be free of seams or seals. This is important as the consumer-facing panel 32 should be the most presentable panel to delight the consumer. Having a seam across the consumer-facing panel 32 would detract from the appearance of the package. When the package is filled with one or more absorbent articles, all of the panels may or may not be generally rectangular in shape. The bottom panel 34 may have a fold line 52, based on how the package is made.

FIG. 2G illustrates the package 30 prior to the seals being added and prior to the consumer-facing panel 32 being folded so that it is in a facing relationship with the back panel 36 (as shown in FIG. 2A). In FIG. 2G it is evident that the first and second top panels, the consumer-facing panel 32, the bottom panel 36, the and the back panel 34 are formed of a continuous material.

Figure 3A:
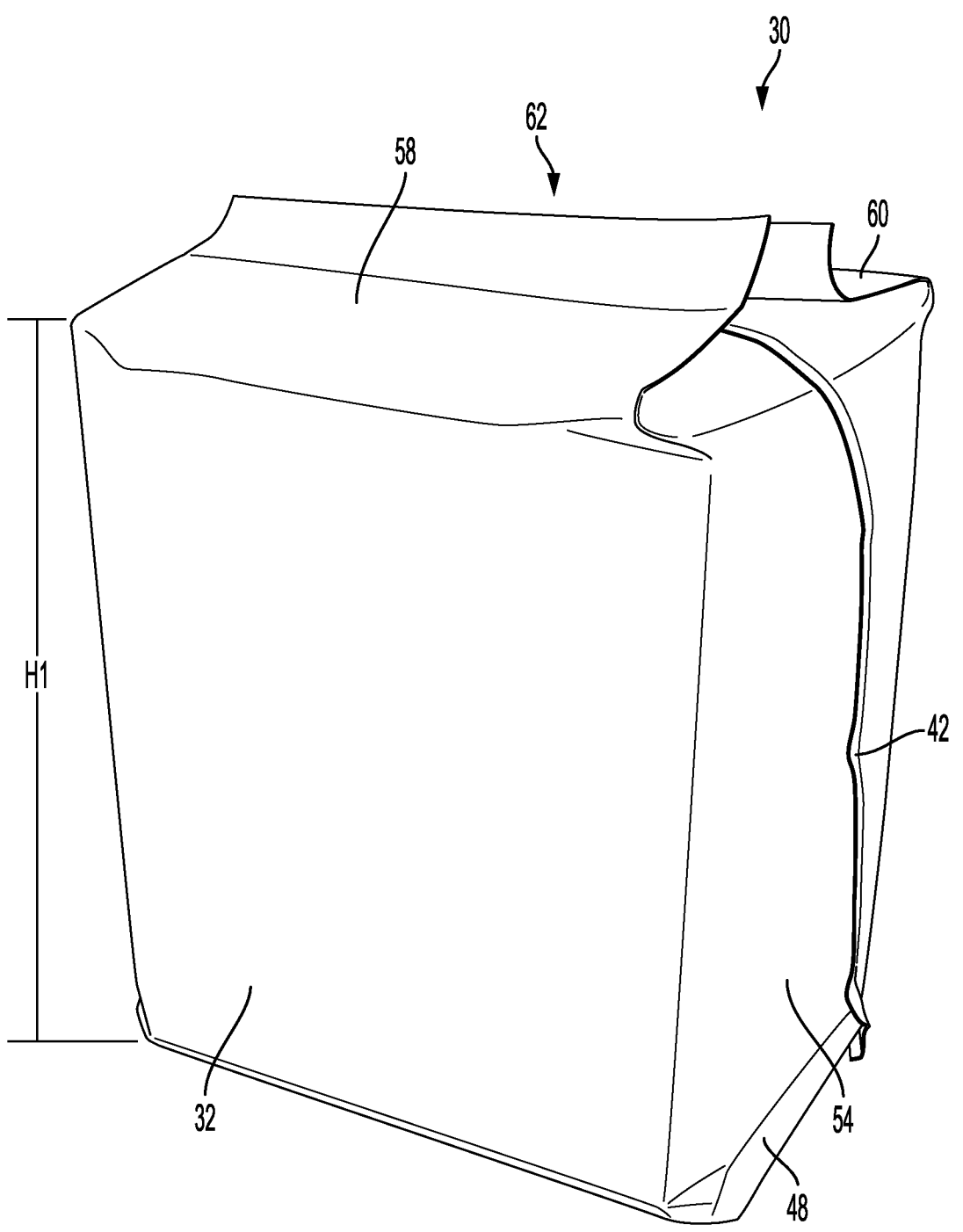
FIG. 3A is a front right side perspective view of an example package with a plurality of absorbent articles positioned therein of the present disclosure.
Figure 3B:
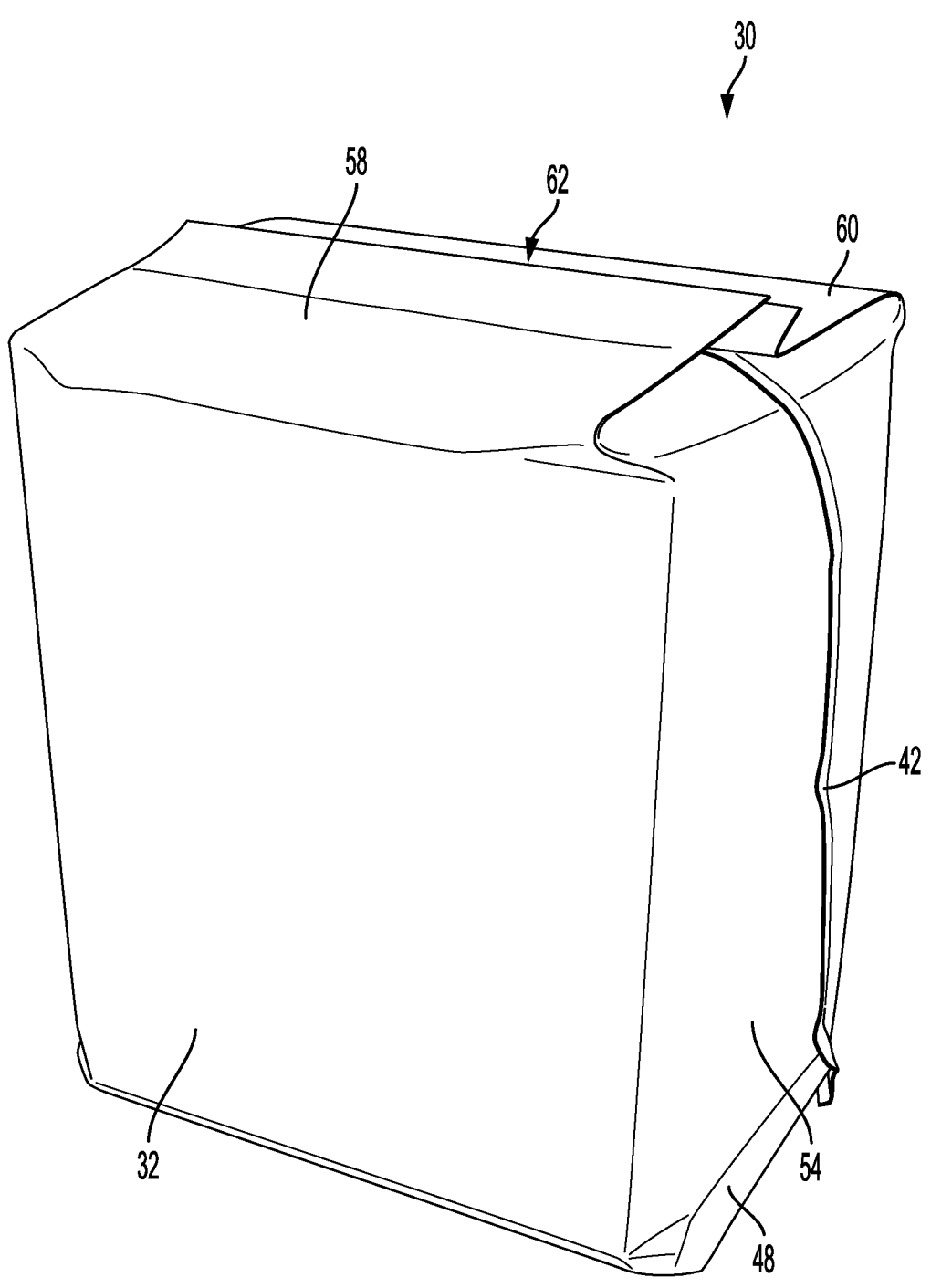
FIG. 3B is another front right side perspective view of the package of FIG. 3A.
Figure 3C:
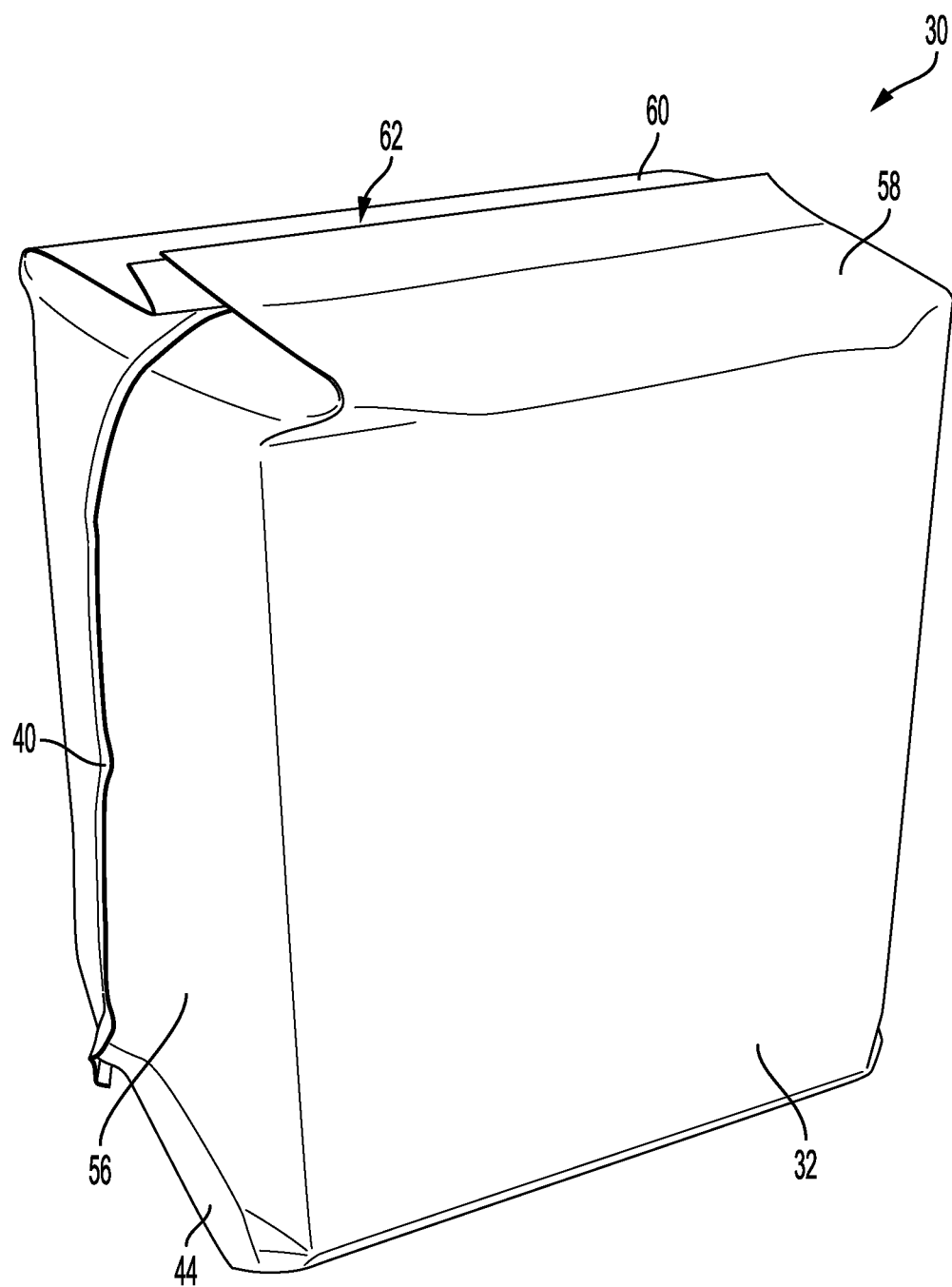
FIG. 3C is a front left side perspective view of the package of FIG. 3A.
Figure 3D:
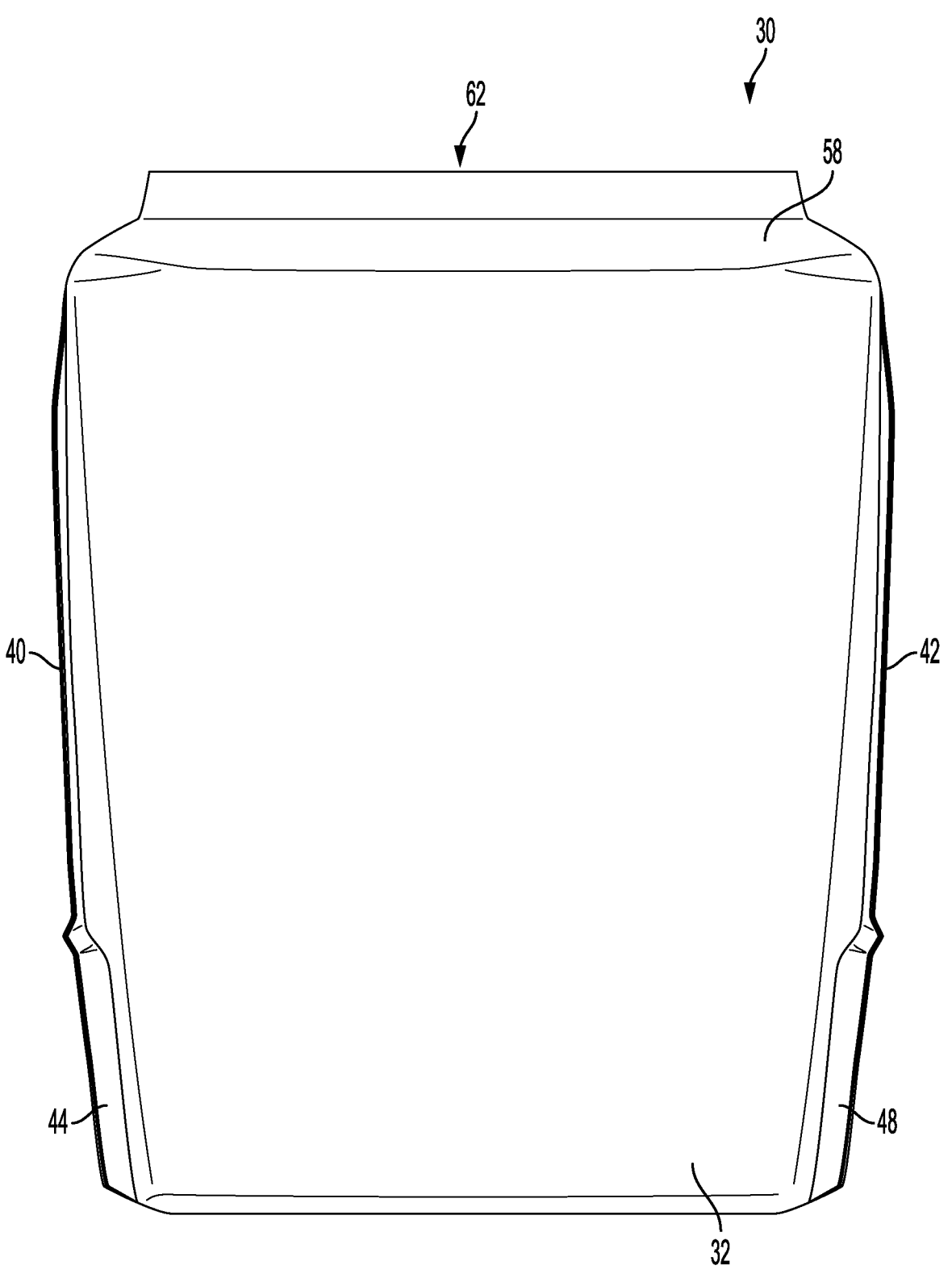
FIG. 3D is a front view of the package of FIG. 3A.
Figure 3E:
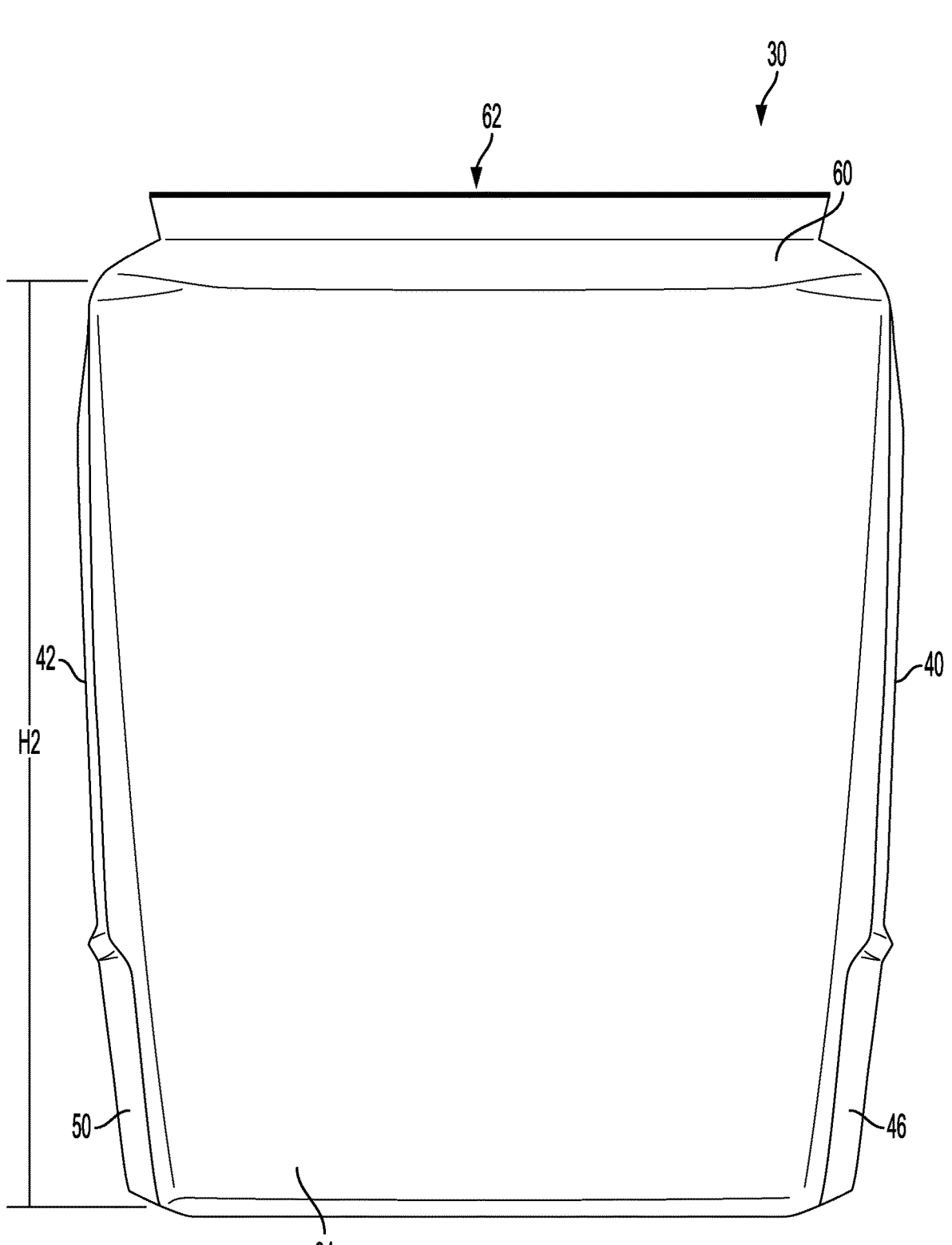
FIG. 3E is a rear view of the package of FIG. 3A.
Figure 3F:
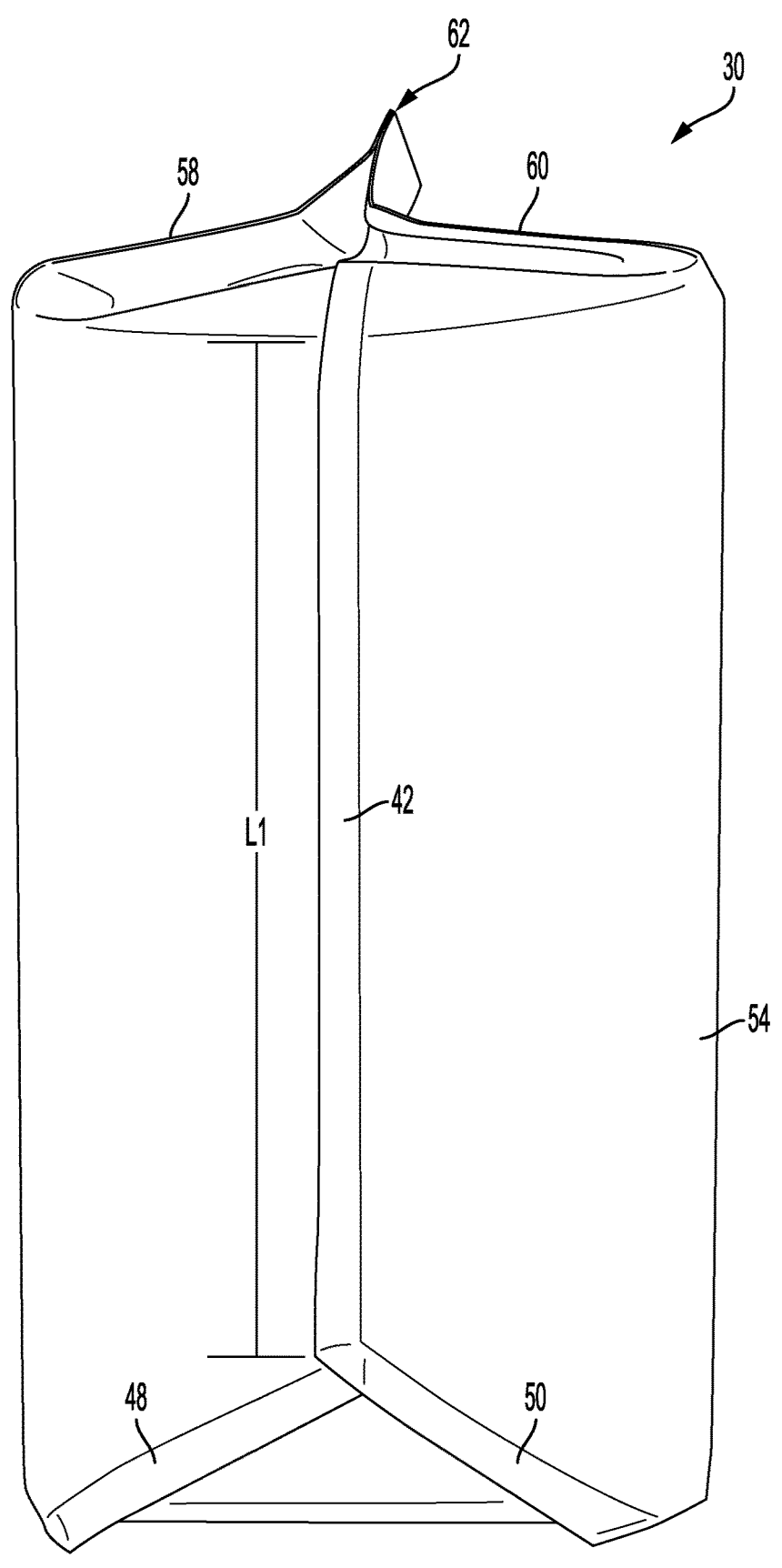
FIG. 3F is a right side view of the package of FIG. 3A.
Figure 3G:
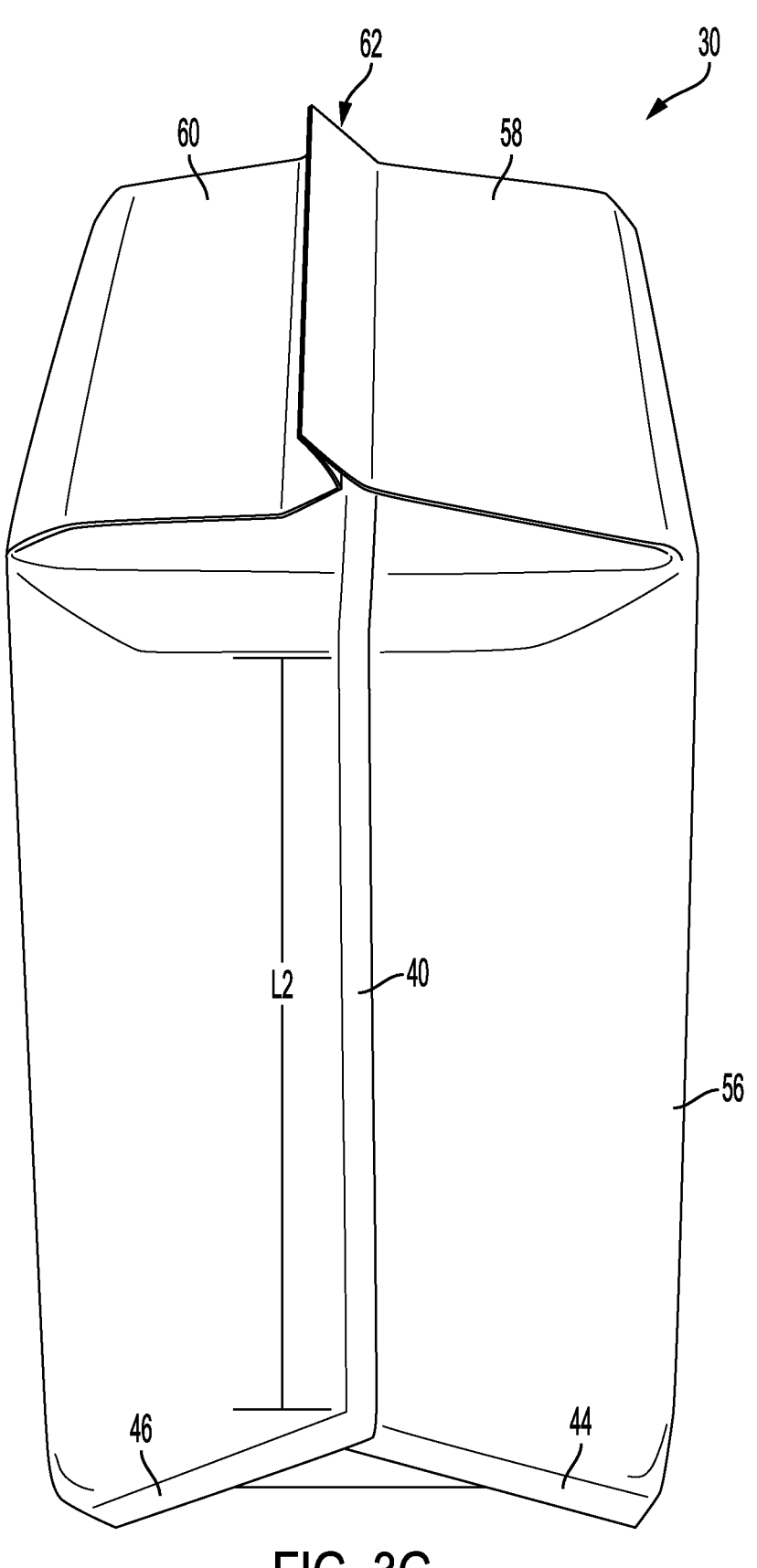
FIG. 3G is a left side perspective view of the package of FIG. 3A.
Figure 3H:
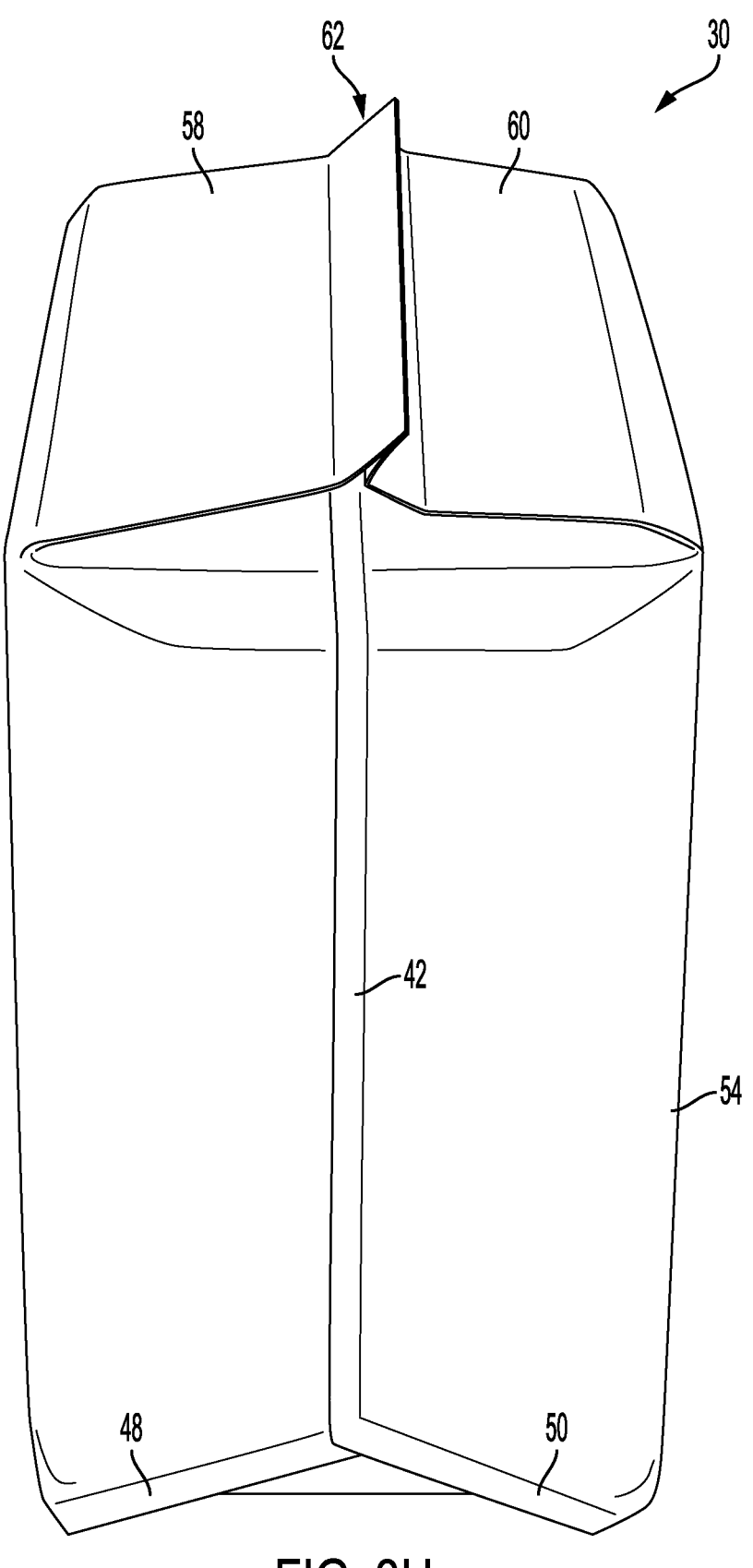
FIG. 3H is a right side perspective view of the package of FIG. 3A.
Figure 3I:
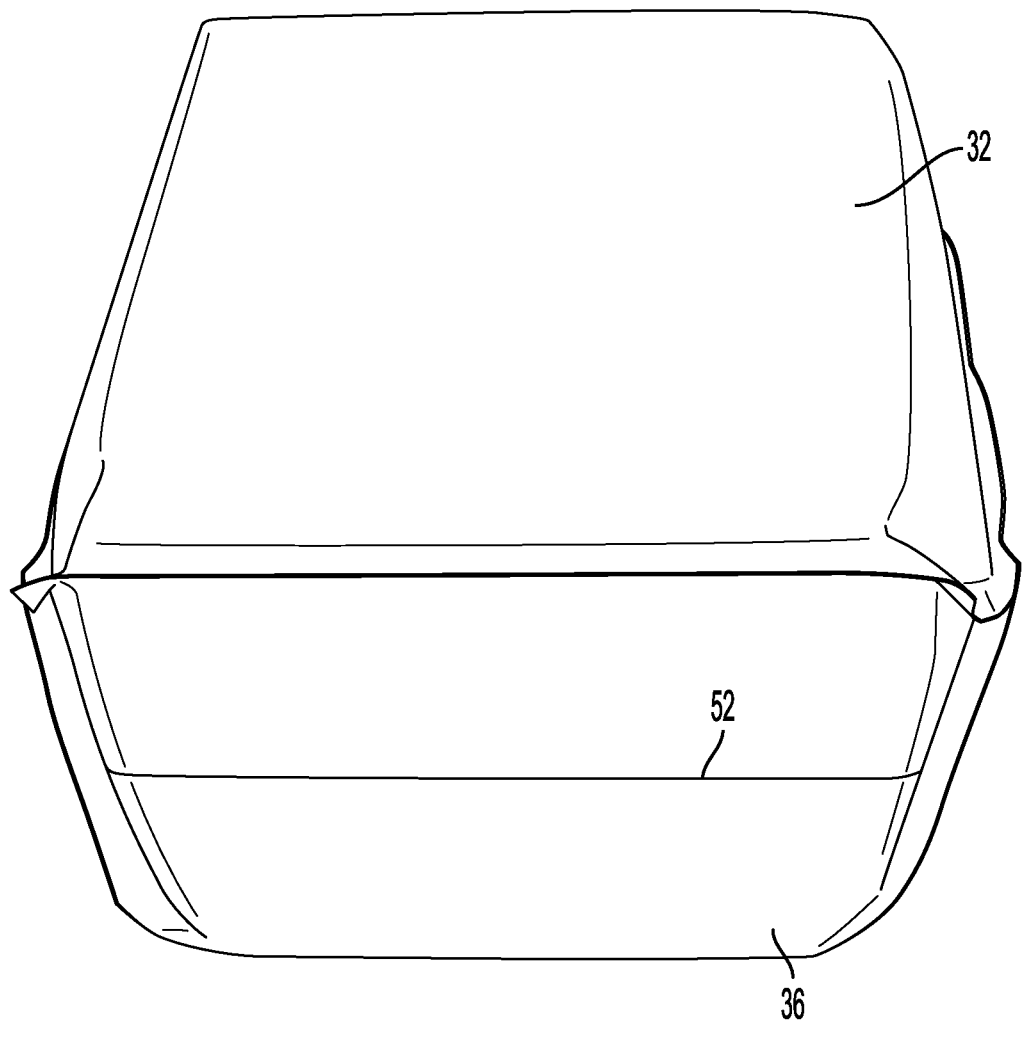
FIG. 3I is a bottom perspective view of the package of FIG. 3A.

An example package 30 containing one or more, or a plurality of absorbent articles is illustrated in FIGS. 3A-3I. FIG. 3A is a front right side perspective view of an example package with a plurality of absorbent articles positioned therein of the present disclosure. FIG. 3B is another front right side perspective view of the package of FIG. 3A. FIG. 3C is a front left side perspective view of the package of FIG. 3A. FIG. 3D is a front view of the package of FIG. 3A. FIG. 3E is a rear view of the package of FIG. 3A. FIG. 3F is a right side view of the package of FIG. 3A. FIG. 3G is a left side perspective view of the package of FIG. 3A. FIG. 3H is a right side perspective view of the package of FIG. 3A. FIG. 3I is a bottom perspective view of the package of FIG. 3A.

The package 30 may comprise a consumer-facing panel 32, a right side panel 54, a left side panel 56, a first top panel 58, a second top panel 60, a bottom panel 36, and a back panel 34. The first and second top panels 58, 60 together form a top panel. A portion of the first top panel 58 is sealed or seamed to a portion of the second top panel 60 to form a top seam 62. The first top panel 58 may be sealed to the second top panel 60 to form the top seam 62 using adhesives, the heat scalable lacquer, or the one or more barrier film layers discussed herein. The top seam 62 may be a thermal seal or other type of seal. It should be noted that in FIGS. 3A-3I, a portion of the second top panel 60 that contained the wicket holes 38 has been removed. The overall top seam of the package including the sides and top seam 62 is generally known as a gusset seal.

The package 30 may comprise a vertical left side seam 40, a vertical right side seam 42, a first left side angled seam 44, a second left side angled seam 46, a first right side angled seam 48, and a second right side angled seam 50. The seams or seals may be butt seams or overlap seams, for example. The vertical left side seam 40 may be longer than the first left side angled seam 44 and longer than the second left side angled seam 46. The vertical right side seam 42 may be longer than the first right side angled seam 48 and longer than the second right side angled seam 50. The package may also comprise a fold line 52 in the bottom panel 34. The consumer-facing panel 32 may have a consumer facing panel height "H2" that is greater than a length "L1" of the vertical right side seam 42 and a length "L2" of the vertical left side seam 40. The back panel 34 may have a back panel height "H1" that is greater than a length "L1" of the vertical right side seam 42 and a length "L2" of the vertical left side seam 40.

The vertical left side seam 40 and the vertical right side seam 42 may have a vertical side seal strength in the range of about 4.9 N/15 mm to about 18 N/15 mm, about 4.9 N/15 mm to about 15 N/15 mm, 5.1 N/15 mm to about 15 N/15 mm, about 5.1 N/15 mm to about 12 N/15 mm, about 5.1 N/15 mm to about 10 N/15 mm, about 5.5 N/15 mm to about 8.5 N/15 mm, about 6.1 N/15 mm, about 7.6 N/15 mm, or about 7.8 N/15 mm, according to the Seal Tensile Strength Test herein. This vertical side seal strength is acceptable for the entire distribution and shelf life of the packages.

The first left side angled seam 44, the second left side angled seam 46, the first right side angled seam 48, and the second right side angled seam 50 may have angled seam seal strength in the range of about 4.4 N/15 mm to about 12 N/15 mm, about 4.4 N/15 mm to about 10 N/15 mm, about 4.5 N/15 mm to about 10 N/15 mm, about 5 N/15 mm to about 10 N/15 mm, about 5.5 N/15 mm to about 8 N/15 mm, about 5.7 N/15 mm, about 7.2 N/15 mm, or about 6.7 N/15 mm, according to the Seal Tensile Strength Test herein. This angled seam seal strength is acceptable for the entire distribution and shelf life of the packages.

In such packages, the one or more absorbent articles may comprise diapers, pants, or adult incontinence pants or moderate to heavy use adult incontinence pads. Additional examples are contemplated wherein at least one seal comprises a higher, lower, or different seal tensile strength than another seal.

Figure 4A:
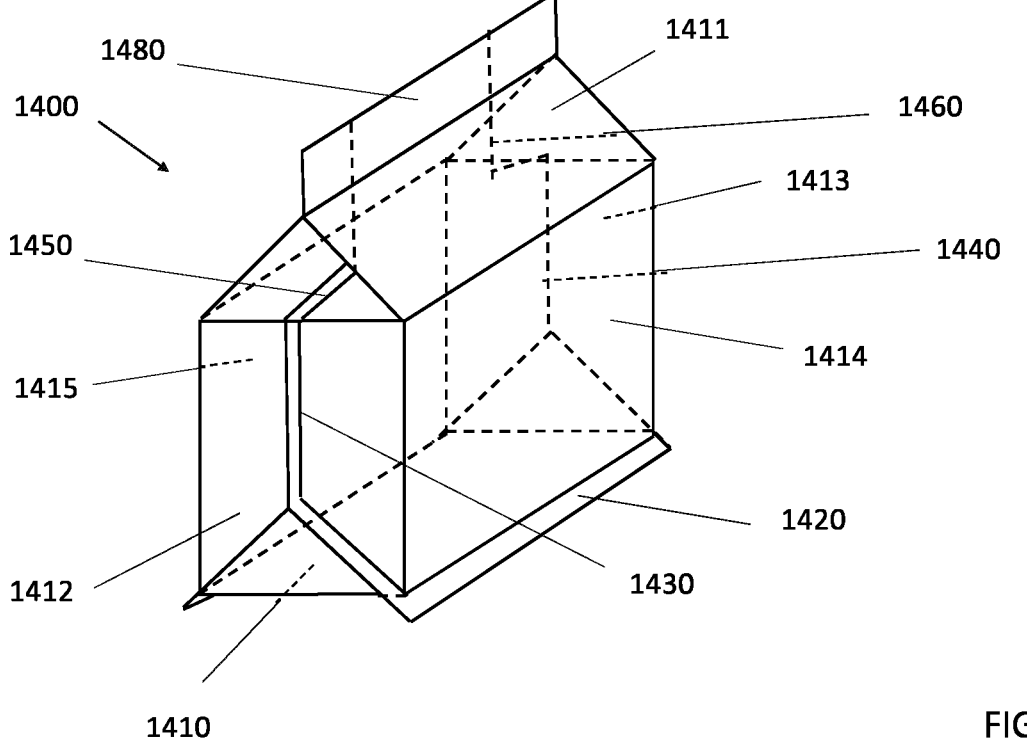
FIG. 4A is a schematic representation showing another package in accordance with the present disclosure.
Figure 4B:
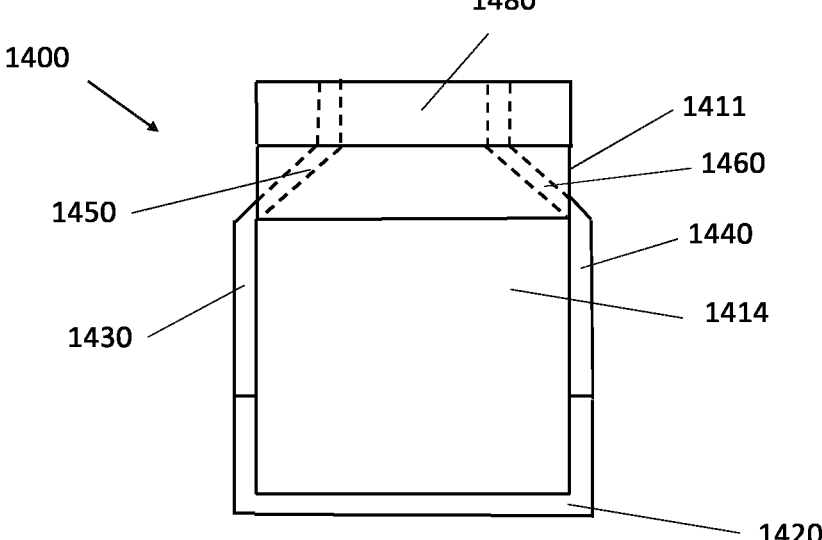
FIG. 4B is a schematic representation showing a rotated view of the package of FIG. 4A.

In an example, a Totani™ style bag may be utilized. The Totani™ style of bag may comprise seams/seals which are overt. Referring to FIGS. 4A and 4B, a Totani™ style package 1400 is shown. The package 1400 may be configured in generally a cuboid shape. The package 1400 may comprise a first panel 1411, opposing second and third panels 1412 and 1413, opposing fourth and fifth panels 1414 and 1415, and a sixth panel 1410 opposing the first panel 1411. As shown, between the fourth panel 1414 and the sixth panel 1410, a first seal 1420 extends outward. The first seal 1420 forms a sort of foot for the package 1400. A second seal may extend outward between the fifth panel 1415 and the sixth panel 1410 in a similar fashion to the first seal 1420. It is worth noting that in some forms, the first panel 1411 may lay flat much like the sixth panel 1410.

The first seal 1420 can extend such that a portion of the first seal 1420 is on the second panel 1412 and another portion of the first seal 1420 is disposed on the third panel 1413. Similarly, a portion of the second seal may be disposed on the second panel 1412 and another portion may be disposed on the third panel 1413. The first seal 1420 and the second seal may be provided where the sixth panel 1410 is formed from a discrete piece of material which is subsequently joined to the fourth panel 1414 and fifth panel 1415.

Of course forms where the sixth panel 1410 is unitary with the fourth panel 1414 and fifth panel 1415 are also contemplated.

A third seal 1430 and a fourth seal 1440 may extend outward from the second panel 1412 and the third panel 1413, respectively. It is worth noting that the first seal 1420, second seal, third seal 1430, and fourth seal 1440 collectively may comprise the hoop seal discussed heretofore. So, one, all or any combination, of these seals may exhibit the tensile strength for the hoop seal as described herein.

As shown, the package 1400 may further comprise a fifth seam 1450 and a sixth seam 1460 which are disposed on the sixth panel 1411. The fifth seam 1450 and sixth seam 1460 can extend into a seal fin 1480. It is worth noting that the package 1400 and the seams associated therewith, may be assembled as described herein regarding adhesives, films, and/or combinations of films and adhesives. However, the construction of the package 1400 is particularly well suited for the creation of seams via oner or more barrier film layers on an inner surface of the package material. In such configurations, the one or more barrier film layers may form a barrier that reduces the likelihood or at least the amount of moisture vapor through the package material to the absorbent articles therein.

The packages of the present disclosure may comprise a plurality of compressed articles, e.g. compressed disposable absorbent articles. For example, packages of the present disclosure may be used for accommodating feminine hygiene pads. As shown in FIG. 4, the package 1 defines an interior space 1002 in which a plurality of absorbent articles 1004 are situated. The plurality of absorbent articles 1004 may be arranged in one or more stacks 1006. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages. Despite lacking the stretch properties of conventional plastic packaging material, the inventors have surprisingly found the package materials of the present disclosure are able to withstand the processing and distribution rigors, as mentioned heretofore, even with absorbent articles which are compressed within the package. This is particularly unexpected as the materials of the present disclosure do not display the stretch properties of presently used conventional plastic films.

Accordingly, packages of the absorbent articles of the present disclosure may have an In-Bag Stack Height of less than about 150 mm, less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, according to the In-Bag Stack Height Test described herein. Alternatively, packages of the absorbent articles of the present disclosure may have an In-Bag Stack Height of from about 70 mm to about 150 mm, from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, according to the In-Back Stack Height Test described herein.

Figure 5:
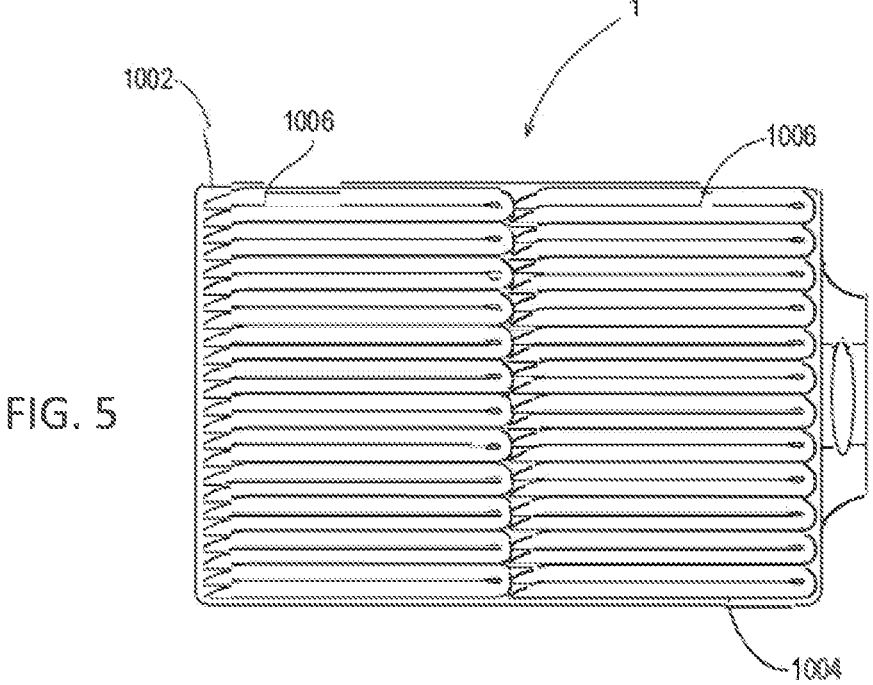
FIG. 5 is a cross-sectional view of an example package showing absorbent articles therein.

It is worth noting that the absorbent articles within the packages of the present disclosure can be arranged in a myriad of configurations. For example, absorbent articles of the present disclosure may be disposed within the package such that they are oriented in a vertical orientation, or the absorbent articles may be arranged such that they are arranged in a horizontal configuration, for example as shown in FIG. 5. Forms are contemplated where a combination of horizontal and vertically oriented articles are provided in the package.

Additionally, the absorbent articles within the package may be oriented such that one longitudinal peripheral edge of each of the plurality of articles is more proximal to the consumer-facing panel than another longitudinal peripheral edge. For example, where the number of absorbent articles within the package is relatively high, e.g. greater than nine, the absorbent articles may be arranged within the package as described heretofore. However, where the number of absorbent articles within the package is lower than, for example nine, the absorbent articles may be arranged such that a topsheet or a backsheet of an absorbent article is more proximal to the consumer-facing panel. Additional absorbent articles may be stacked behind the absorbent article which is closest to the consumer-facing panel. Forms are contemplated where there is a combination of orientations within the package. For example, at least one absorbent article can be arranged such that one of its longitudinal peripheral side edges is more proximal the consumer-facing panel than another, and at least one absorbent article can be arranged such that its topsheet or backsheet is more proximal to the consumer-facing panel. The remainder of the absorbent articles, if any, can assume either of those configurations.

Absorbent Articles

Figure 6:
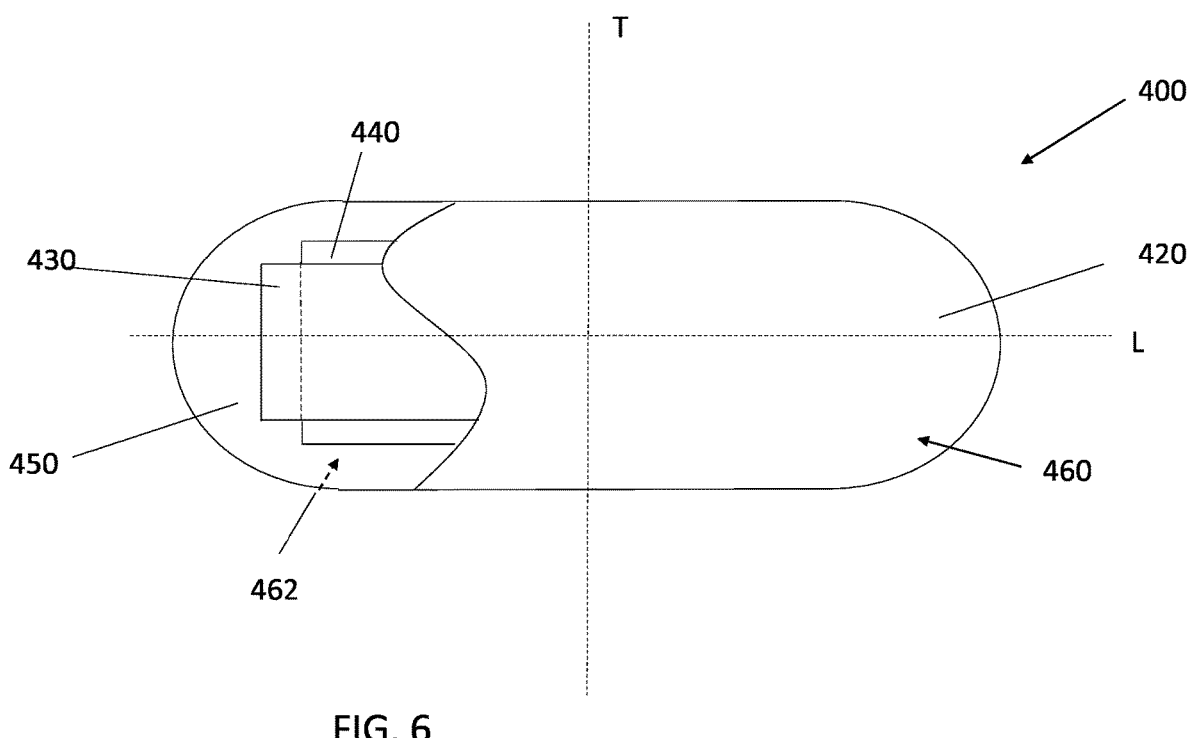
FIG. 6 is a schematic representation of an absorbent article of the present disclosure showing a partial-cutaway-view of the article.
Figure 7A:
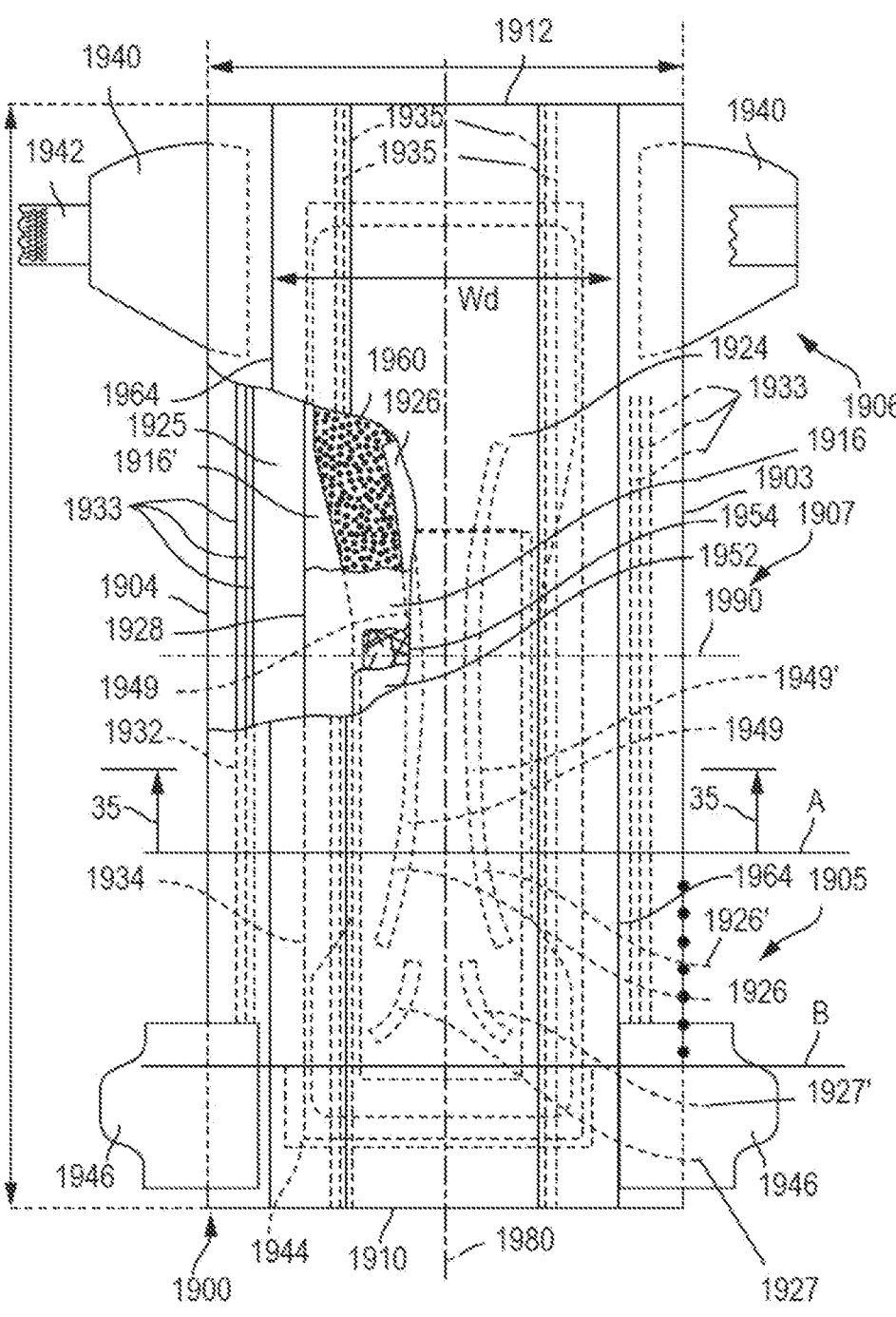
FIG. 7A shows a plan view of a diaper constructed in accordance with the present disclosure.
Figure 7B:
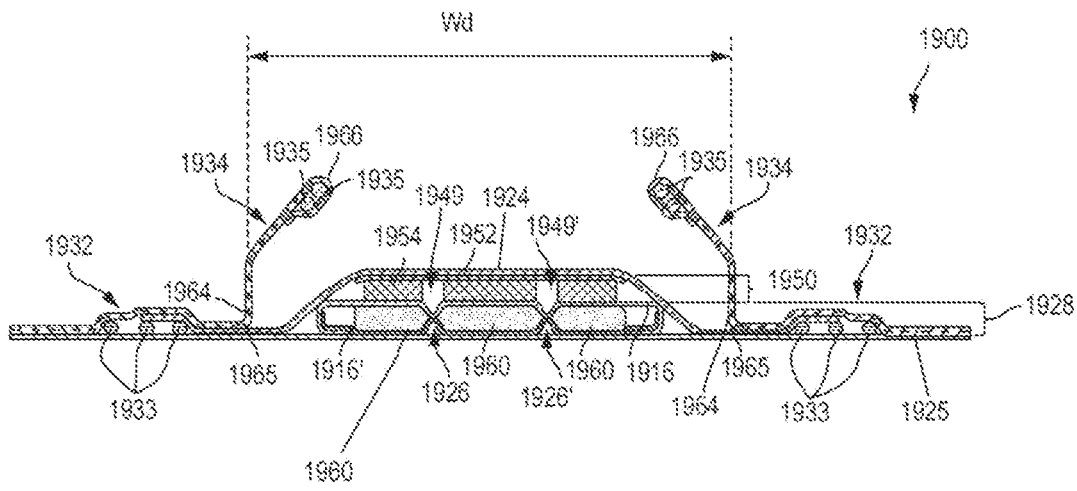
FIG. 7B shows a cross section of the diaper of FIG. 7A taken along lines 35-35.
Figure 7C:
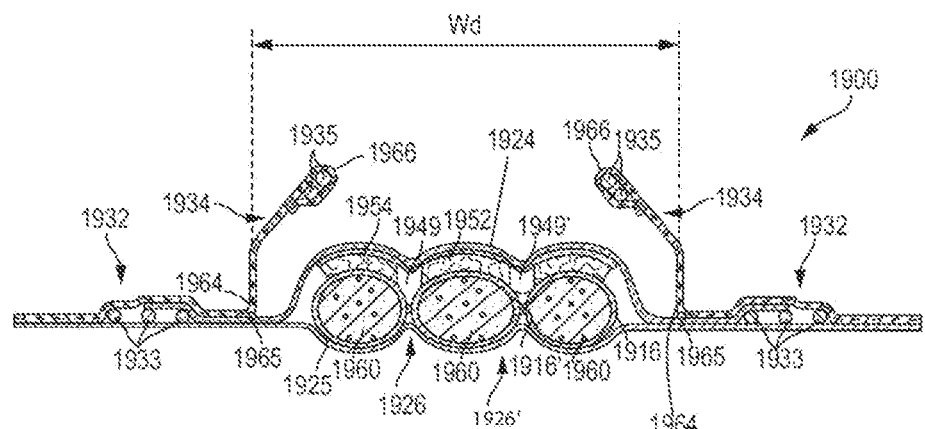
FIG. 7C shows a cross section of the diaper of FIG. 7B in an expanded state.

As noted previously, the absorbent articles which can be packaged within the package material of the present disclosure are numerous. Two specific examples are provided in FIGS. 6 through 7C. However, the package material and packages of the present disclosure may be utilized to contain a multitude of absorbent articles as described previously. FIGS. 6 through 7C are merely examples of absorbent articles which may be contained with the package material/packages of the present disclosure.

In FIG. 6 an example feminine hygiene pad 400 is illustrated. The feminine hygiene pad 400 may comprise a topsheet 420, a backsheet 450, and an absorbent core 440 disposed between the topsheet 420 and the backsheet 450. A fluid management layer 430 may be disposed between the topsheet 420 and the absorbent core 440. The absorbent article has a wearer-facing surface 460 and an opposing garment-facing surface 462. The wearer-facing surface 460 primarily comprises the topsheet 420 while the garment-facing surface 462 primarily comprises the backsheet 450. Additional components may be included in either the wearer-facing surface 460 and/or the garment-facing surface 462. For example, where the absorbent article is an incontinence pad, a pair of barrier cuffs which extend generally parallel to a longitudinal axis L of the absorbent article 400, may also form a portion of the wearer-facing surface 460. Similarly, a fastening adhesive may be present on the backsheet 450 and form a portion of the garment-facing surface 462 of the absorbent article.

The topsheet 420 may be joined to the backsheet 450 by attachment methods such as those known in the art. The topsheet 420 and the backsheet 450 may be joined directly to each other in the article periphery and may be indirectly joined together by directly joining them to the absorbent core 440, the fluid management layer 430, and/or additional layers disposed between the topsheet 420 and the backsheet 450. This indirect or direct joining may be accomplished by attachment methods which are well known in the art.

The topsheet 420 may be compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, may also provide for the transfer or migration of the lotion composition onto an external or internal portion of a wearer's skin.

A suitable topsheet 420 can be made of various materials such as woven and nonwoven materials; apertured film materials including apertured formed thermoplastic films, apertured plastic films, and fiber-entangled apertured films; hydro-formed thermoplastic films; porous foams; reticulated foams; cotton; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975, and U.S. Pat. No. 4,324,246, issued to Mullane et al. on Apr. 13, 1982.

Nonlimiting examples of woven and nonwoven materials suitable for use as the topsheet include fibrous materials made from natural fibers, e.g., cotton, including 100 percent organic cotton, modified natural fibers, synthetic fibers, or combinations thereof. These fibrous materials can be either hydrophilic or hydrophobic, but it is sometimes desirable that the topsheet be hydrophobic or rendered hydrophobic. As an option, portions of the topsheet can be rendered hydrophilic, using any known method for making topsheets containing hydrophilic components. Nonwoven fibrous topsheets 20 may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

The topsheet 420 may be formed from a combination of an apertured film and a nonwoven. For example, a film web and a nonwoven web can be combined as described in U.S. Pat. No. 9,700,463. Alternatively, a film may be extruded onto a nonwoven material which is believed to provide enhanced contact between the film layer and the nonwoven material. Example processes for such a combination are described in U.S. Pat. Nos. 9,849,602 and 9,700,463.

The backsheet 450 may be positioned adjacent a garment-facing surface of the absorbent core 440 and may be joined thereto by attachment methods such as those known in the art. For example, the backsheet 450 may be secured to the absorbent core 440 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are generally known in the art.

The backsheet 450 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet may prevent, or at least inhibit, the exudates absorbed and contained in the absorbent core from wetting articles of clothing which contact the incontinence pad such as undergarments. However, the backsheet may permit vapors to escape from the absorbent core (i.e., is breathable) while in some cases the backsheet may not permit vapors to escape (i.e., non-breathable). Thus, the backsheet may comprise a polymeric film such as thermoplastic films of polyethylene or polypropylene. A suitable material for the backsheet is a thermoplastic film having a thickness of from about 0.012 mm (0.5 mil) to about 0.051 mm (2.0 mils), for example. Any suitable backsheet known in the art may be utilized with the present disclosure.

The backsheet 450 acts as a barrier to any absorbed bodily fluids that may pass through the absorbent core 440 to the garment surface thereof with a resulting reduction in risk of staining undergarments or other clothing. A preferred material is a soft, smooth, compliant, liquid and vapor pervious material that provides for softness and conformability for comfort, and is low noise producing so that movement does not cause unwanted sound.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness.

The backsheet may be a nonwoven web having a basis weight between about 20 gsm and about 50 gsm. The backsheet has a garment-facing side and an opposite body-facing side. The garment-facing side of the backsheet comprises a non-adhesive area and an adhesive area. The adhesive area may be provided by any conventional means. Pressure sensitive adhesives have been commonly found to work well for this purpose.

The absorbent core 440 may comprise any suitable shape including but not limited to an oval, a discorectangle, a rectangle, an asymmetric shape, and an hourglass. For example, in some forms of the present disclosure, the absorbent core 440 may comprise a contoured shape, e.g. narrower in the intermediate region than in the end regions. As yet another example, the absorbent core may comprise a tapered shape having a wider portion in one end region of the pad which tapers to a narrower end region in the other end region of the pad. The absorbent core may comprise varying stiffness in the MD and CD.

The configuration and construction of the absorbent core may vary (e.g., the absorbent core 440 may have varying caliper zones, a hydrophilic gradient, a super absorbent gradient, or lower average density and lower average basis weight acquisition zones). Further, the size and absorbent capacity of the absorbent core 440 may also be varied to accommodate a variety of wearers. However, the total absorbent capacity of the absorbent core 440 should be compatible with the design loading and the intended use of the disposable absorbent article or incontinence pad.

In some forms of the present disclosure, the absorbent core may comprise a plurality of multi-functional layers that are in addition to the first and second laminates. For example, the absorbent core may comprise a core wrap useful for enveloping the first and second laminates and other optional layers. The core wrap may be formed by two nonwoven materials, substrates, laminates, films, or other materials. In a form, the core wrap may only comprise a single material, substrate, laminate, or other material wrapped at least partially around itself. The absorbent core may comprise one or more adhesives, for example, to help immobilize the SAP or other absorbent materials within the first and second laminates.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen. These may be used to configure the super absorbent layers.

Any suitable fluid management layer may be utilized in conjunction with the feminine hygiene pad 400. The fluid management layer may be separate and apart from the absorbent system. Additionally, the fluid management layer is disposed beneath the topsheet and on the wearer-facing surface of the core. The fluid management layer may have a basis weight from about 40 gsm to about 100 gsm, from about 45 gsm to about 75 gsm, or from about 50 gsm to about 65 gsm. In some forms, the fluid management layer may comprise a homogeneous mix of fibers whereas in other forms, the fluid management layer may comprise a heterogeneous mix of fibers.

Another example of an absorbent article which can be included in the packages of the present disclosure are diapers. As shown in FIG. 7A, a plan view of an example absorbent article that is a diaper 1900 in its flat-out, uncontracted state (i.e., with elastic induced contraction pulled out) with portions of the structure being cut-away to more clearly show the construction of the diaper 1900 and with its wearer-facing surface toward the viewer. This diaper is shown for illustration purpose only as the packages of the present disclosure may be used for a wide variety of diapers and other absorbent articles.

The absorbent article may comprise a liquid permeable topsheet 1924, a liquid impermeable backsheet 1925, an absorbent core 1928 positioned at least partially intermediate the topsheet 1924 and the backsheet 1925, and barrier leg cuffs 1934. The absorbent article may also comprise a liquid management system ("LMS") 1950 (shown in FIG. 6B), which, in the example represented, comprises a distribution layer 1954 and an acquisition layer 1952 that will both be further discussed below. In various forms, the acquisition layer 1952 may instead distribute bodily exudates and the distribution layer 1954 may instead acquire bodily exudates or both layers may distribute and/or acquire bodily exudates. The LMS 1950 may also be provided as a single layer or two or more layers. The absorbent article may also comprise elasticized gasketing cuffs 1932 joined to the chassis 1982 of the absorbent article, typically via the topsheet and/or backsheet, and substantially planar with the chassis of the diaper.

The Figures also show typical taped diaper components such as a fastening system comprising adhesive tabs 1942 or other mechanical fasteners attached towards the rear edge of the absorbent article 1900 and cooperating with a landing zone 1944 on the front of the absorbent article 1900. The absorbent article may also comprise other typical elements, which are not represented, such as a rear elastic waist feature (1936 shown in FIG. 8) and a front elastic waist feature (1937 shown in FIG. 8), for example.

The absorbent article 1900 may comprise a front waist edge 1910, a rear waist edge 1912 longitudinally opposing the front waist edge 1910, a first side edge 1903, and a second side edge 1904 laterally opposing the first side edge 1903. The front waist edge 1910 is the edge of the absorbent article 1900 which is intended to be placed towards the front of the user when worn, and the rear waist edge 1912 is the opposite edge. Together the front waist edge 1910 and the rear waist edge form waist opening when the absorbent article 1900 is donned on a wearer. The absorbent article 1900 may have a longitudinal axis 1980 extending from the lateral midpoint of the front waist edge 1910 to a lateral midpoint of the rear waist edge 1912 of the absorbent article 1900 and dividing the absorbent article 1900 in two substantially symmetrical halves relative to the longitudinal axis 1980, with article placed flat and viewed from the wearer-facing surface as illustrated FIG. 7A. The absorbent article may also have a lateral axis 1990 extending from the longitudinal midpoint of the first side edge 1903 to the longitudinal midpoint of the second side edge 1904. The length L of the absorbent article 1900 may be measured along the longitudinal axis 1980 from the front waist edge 1910 to the rear waist edge 1912. The crotch width of the absorbent article 1900 may be measured along the lateral axis 1990 from the first side edge 1903 to the second side edge 1904. The absorbent article 1900 may comprise a front waist region 1905, a rear waist region 1906, and a crotch region 1907. The front waist region, the rear waist region, and the crotch region each define ⅓ of the longitudinal length of the absorbent article. Front and back portions may also be defined on opposite sides of the lateral axis 1990.

The topsheet 1924, the backsheet 1925, the absorbent core 1928, and the other article components may be assembled in a variety of configurations, in particular by gluing or heat embossing, for example.

The absorbent core 1928 may comprise an absorbent material comprising 75% to 100%, at least 80%, at least 85%, at least 90%, at least 95%, or at least 99%, all by weight, of the absorbent material, and a core wrap enclosing the absorbent material. The core wrap may typically comprise two materials, substrates, or nonwoven materials 16 and 16' for the top side and bottom side of the core.

The absorbent core 1928 may comprises one or more channels, represented in FIG. 6A as the four channels 1926, 1926' and 1927, 1927'. Additionally or alternative, the LMS 1950 may comprises one or more channels, represented in FIGS. 7A-7C as channels 1949, 1949'. In some forms, the channels of the LMS 1950 may be positioned within the absorbent article 1900 such they aligned with, substantially aligned with, overlap, or at least partially overlap, the channels of the absorbent core 1928. The channels may be areas free of absorbent material or may be embossed or compressed, but with absorbent material present. These and other components of the absorbent articles will now be discussed in more details.

The topsheet 1924 is the part of the absorbent article that is directly in contact with the wearer's skin. The topsheet 1924 may be joined to the backsheet 1925, the core 1928 and/or any other layers as is known to those of skill in the art. Usually, the topsheet 1924 and the backsheet 1925 are joined directly to each other in some locations (e.g., on or close to the periphery of the article) and are indirectly joined together in other locations by directly joining them to one or more other elements of the absorbent article 1900.

The backsheet 1925 is generally that portion of the absorbent article 1900 positioned adjacent the garment-facing surface of the absorbent core 1928 and which prevents, or at least inhibits, the bodily exudates absorbed and contained therein from soiling articles such as bedsheets and undergarments. The backsheet 1925 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm.

Example backsheet films include those manufactured by Tredegar Corporation, based in Richmond, VA, and sold under the trade name CPC2 film. Other suitable backsheet materials may include breathable materials which permit vapors to escape from the absorbent article 1900 while still preventing, or at least inhibiting, bodily exudates from passing through the backsheet 1925. Example breathable materials may include materials such as woven webs, non-woven webs, and composite materials such as film-coated nonwoven webs, microporous films, and monolithic films. In one specific example, the backsheet may comprise a film and a nonwoven, wherein the nonwoven (1971 shown in FIG. 8) forms a portion of a garment-facing surface of the article.

The backsheet 1925 may be joined to the topsheet 1924, the absorbent core 1928, and/or any other element of the absorbent article 1900 by any attachment methods known to those of skill in the art. Suitable attachment methods are described above with respect to methods for joining the topsheet 1924 to other elements of the absorbent article 1900.

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 1928 of the present disclosure may comprise an absorbent material with a high amount of super absorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 1928 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers.

The absorbent core 1928 may also comprise a generally planar top side and a generally planar bottom side. The core 1928 may have a longitudinal axis 80' corresponding substantially to the longitudinal axis 80 of the absorbent article, as seen from the top in a planar view as in FIG. 6A. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 1916, 1916' which may be at least partially sealed along the sides of the absorbent core. The core wrap may be at least partially sealed along its front side, rear side, and two longitudinal sides so that substantially no absorbent material leaks out of the absorbent core wrap. The first material, substrate, or nonwoven 1916 may at least partially surround the second material, substrate, or nonwoven 1916' to form the core wrap. The first material 1916 may surround a portion of the second material 1916' proximate to the first and second side edges 1903 and 1904.

Cores comprising relatively high amount of SAP with various core designs are disclosed in U.S. Pat. No. 5,599,335 (Goldman), and EP 1,447,066 (Busam).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 1928 may comprise a first absorbent layer and a second absorbent layer. The first absorbent layer may comprise the first material 1916 and a first layer 1961 of absorbent material, which may be 100% or less of SAP. The second absorbent layer may comprise the second material 1916' and a second layer 1962 of absorbent material, which may also be 100% or less of SAP.

The fibrous thermoplastic adhesive material 1951 may be at least partially in contact with the absorbent material 1961, 1962 in the land areas and at least partially in contact with the materials 1916 and 1916' in the junction areas. This imparts an essentially three-dimensional structure to the fibrous layer of thermoplastic adhesive material 591, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal for the core wrap does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

The absorbent article may comprise a pair of barrier leg cuffs 1934. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 1934 are delimited by a proximal edge 1964 joined directly or indirectly to the topsheet 1924 and/or the backsheet 1925 and a free terminal edge 1966, which is intended to contact and form a seal with the wearer's skin. The barrier leg cuffs 1934 extend at least partially between the front waist edge 1910 and the rear waist edge 1912 of the absorbent article on opposite sides of the longitudinal axis 1980 and are at least present in the crotch region 1907. The barrier leg cuffs 1934 may be joined at the proximal edge 1964 with the chassis of the absorbent article by a bond 1965 which may be made by gluing, fusion bonding, or combination of other suitable bonding processes. The bond 1965 at the proximal edge 1964 may be continuous or intermittent. The bond 1965 closest to the raised section of the leg cuffs 1934 delimits the proximal edge 1964 of the standing up section of the leg cuffs 1934.

The barrier leg cuffs 1934 may be integral with the topsheet 1924 or the backsheet 1925 or may be a separate material joined to the absorbent article's chassis. The material of the barrier leg cuffs 1934 may extend through the whole length of the diapers but may be "tack bonded" to the topsheet 1924 towards the front waist edge 1910 and rear waist edge 1912 of the absorbent article so that in these sections the barrier leg cuff material remains flush with the topsheet 1924.

Each barrier leg cuff 1934 may comprise one, two or more elastic strands or strips of film 1935 close to this free terminal edge 1966 to provide a better seal. It is worth noting that barrier leg cuffs may similarly be applied to a pad type of structure as described regarding FIG. 5. Such configurations may be desirable in an adult incontinence pad. Any of the configurations described herein for the barrier leg cuffs may be utilized for adult incontinence pads.

In addition to the barrier leg cuffs 1934, the absorbent article may comprise gasketing cuffs 1932, which are joined to the chassis of the absorbent article, in particular to the topsheet 1924 and/or the backsheet 1925 and are placed externally relative to the barrier leg cuffs 1934. The gasketing cuffs 1932 may provide a better seal around the thighs of the wearer. Each gasketing leg cuff may comprise one or more elastic strings or clastic elements 1933 in the chassis of the absorbent article between the topsheet 1924 and backsheet 1925 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front cars 1946 and rear cars 1940. The cars may be an integral part of the chassis, such as formed from the topsheet 1924 and/or backsheet 1925 as side panel. Alternatively, as represented on FIG. 7A, the cars (1946, 1940) may be separate elements attached by gluing, heat embossing, and/or pressure bonding. The rear cars 1940 may be stretchable to facilitate the attachment of the tabs 1942 (fasteners 1943) to the landing zone 1944 and maintain the taped diapers in place around the wearer's waist. The rear ears 1940 may also be elastic or extensible to provide a more comfortable and contouring fit by initially conformably fitting the absorbent article to the wearer and sustaining this fit throughout the time of wear well past when absorbent article has been loaded with exudates since the elasticized cars allow the sides of the absorbent article to expand and contract.

One function of the LMS 1950 is to quickly acquire the fluid and distribute it to the absorbent core 1928 in an efficient manner. The LMS 1950 may comprise one or more layers, which may form a unitary layer or may remain as discrete layers which may be attached to each other. The LMS 1950 may comprise two layers: a distribution layer 1954 and an acquisition layer 1952 disposed between the absorbent core and the topsheet, but the present disclosure is not limited to such a configuration.

The LMS 1950 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example.

The LMS 1950 may comprise a distribution layer 1954. The distribution layer 1954 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

The LMS 1950 may alternatively or additionally comprise an acquisition layer 1952. The acquisition layer 1952 may be disposed, for example, between the distribution layer 1954 and the topsheet 1924. The acquisition layer 1952 may be or may comprise a non-woven material, such as an SMS or SMMS material, comprising a spunbonded, a melt-blown and a further spunbonded layer or alternatively a carded chemical-bonded nonwoven. The acquisition layer 1952 may comprise air or wet-laid cellulosic, cross-linked cellulosic, or synthetic fibers, or blends thereof. The acquisition layer 1952 may comprise a roll-stock web of synthetic fibers (which may be processed to increase void space, such as by solid state formation), or a combination of synthetic and cellulosic fibers, bonded together to form a highloft material. Alternatively, the acquisition layer 1952 may comprise absorbent open cell foam. The nonwoven material may be latex bonded.

The LMS 1950 of the absorbent article 1900 may comprise channels that may generally enable better conformation of the absorbent article to the wearer's anatomy, leading to increased freedom-of-movement and reduced gapping. One or more of the channels of the LMS 1950 may be configured to work in concert with various channels in the absorbent core 1928, as discussed above. Furthermore, channels in the LMS 1950 may also provide increased void space to hold and distribute urine, BM or other bodily exudates within the absorbent article, leading to reduced leakage and skin contact. Channels in the LMS 1950 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

Wetness Indicator/Graphics

Figure 8:
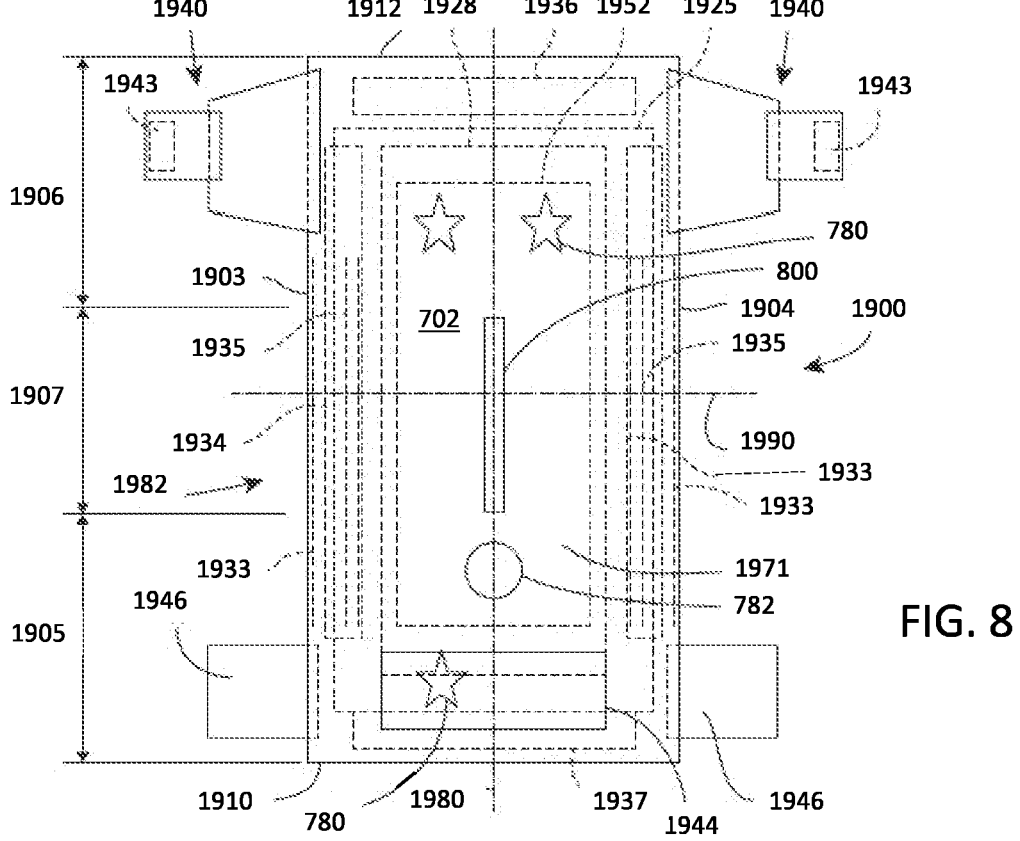
FIG. 8 shows a plan view of an example absorbent article in the form of a taped diaper, garment-facing surface facing the viewer, in a flat laid-out state.

Referring to FIGS. 7A and 8, the absorbent articles 1900 of the present disclosure may comprise graphics 780 and/or wetness indicators 800 that are visible from the garment-facing surface 702. The graphics 780 may be printed on the landing zone 740, the backsheet 1925, and/or at other locations. The wetness indicators 800 are typically applied to the absorbent core facing side of the backsheet 1925, so that they can be contacted by bodily exudates within the absorbent core 1928. In some instances, the wetness indicators 800 may form portions of the graphics 780. For example, a wetness indicator may appear or disappear and create/remove a character within some graphics. In other instances, the wetness indicators 800 may coordinate (e.g., same design, same pattern, same color) or not coordinate with the graphics 780.

Other Products within the Packages of the Present Disclosure

Many suitable products may be placed within the packages and package materials of the present disclosure, such as consumer products. As an example, packages of the present disclosure may comprise or have contained therein, one or more moisture labile products, humidity labile products, moisture sensitive products, or water vapor sensitive products including unit dose products, unit dose pouches, articles meant for single use, pouches, pouches with fibrous wall materials, pouches with soluble film wall materials, pouches comprising a single layer or ply, and combinations thereof. These unit dose or pouch form products are delivery vehicles comprising active agents or additives designed and intended to provide a benefit to something, such as providing a benefit to an environment external to the unit dose or pouch. One embodiment may comprise a unit dose article or pouch where active agents are contained on the internal volume of the unit dose article or pouch. Another embodiment may comprise a unit dose or pouch comprising a single layer or ply where the active agent is contained within the single layer or ply, coated or embedded on the surface of the layer or ply, or a combination of these two configurations.

Active agents may be any suitable additive that produces an intended effect under intended use conditions of the unit dose article or pouch. For example, the active agent may be selected from the group consisting of: personal cleansing and/or conditioning agents, such as hair care agents such as shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; liquid and/or powder dishwashing agents (for hand dishwashing and/or automatic dishwashing machine applications), hard surface care agents, and/or conditioning agents and/or polishing agents; other cleaning and/or conditioning agents such as antimicrobial agents, antibacterial agents, antifungal agents, fabric hueing agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, clay soil removing agents, anti-redeposition agents, polymeric soil release agents, polymeric dispersing agents, alkoxylated polyamine polymers, alkoxylated polycarboxylate polymers, amphilic graft copolymers, dissolution aids, buffering systems, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, teeth whitening agents, tooth care agents, mouthwash agents, periodontal gum care agents, edible agents, dietary agents, vitamins, minerals; water-treatment agents such as water clarifying and/or water disinfecting agents, surfactants, anionic surfactants, cationic surfactants, nonionic surfactants, zwitterionic surfactants, amphoteric surfactants, one or more silicones, one or more alkali metal or alkaline-earth metal carbonates, alkali metal carbonates (e.g. sodium carbonate, potassium carbonate, etc.), alkali metal hydrogen carbonates (e.g., sodium hydrogen carbonate, potassium hydrogen carbonate, etc.), ammonium carbonate, organic acids (e.g., hydroxy-carboxylic acids [citric acid, tartaric acid, malic acid, lactic acid, gluconic acid, etc.], saturated aliphatic carboxylic acids [acetic acid, succinic acid, etc.], unsaturated aliphatic carboxylic acids [e.g., fumaric acid, etc.]. and mixtures thereof.

Example unit dose articles or pouches of the present disclosure include those described in U.S. Pat. Appl. Pub. No. 2013/0172226, U.S. Pat. Appl. Pub. No. 2015/0071572, U.S. Pat. Appl. Pub. No. 2018/0216285, U.S. Pat. Appl. Pub. No. 2018/0216286, U.S. Pat. Appl. Pub. No. 2018/0216287, U.S. Pat. Appl. Pub. No. 2018/0216288, and PCT publications WO 2022/117853, WO 2022/117854, WO 2022/117855, WO 2022/117856, WO 2022/117858, WO 2022/117859, WO 2022/117860, WO 2022/117861.

Handles

The various packages of the present disclosure may comprise one or more handles. The handles may be discrete components attached to outer surfaces of the packages or may be integrally formed with the package materials. In the instance in which the handles are discrete components, the discrete handles may be formed of the same or similar materials as the packages or may be formed of different materials as the packages. As an example, the discrete handles may comprise natural fibers and/or may comprise polyolefins, or laminates of the same, for example. The handles may aid a consumer in picking up and transporting the packages. As an example, a handle may be placed on or formed with the consumer-facing panel 32 and another handle may be placed on the back panel 34. In another instance, a handle may be placed on or formed with only the back panel 34 to allow for a better presentation of graphics, brands, claims, and/or images on the consumer facing panel 32. The handles may also be placed on the other portions of the packages, such as the top or bottom panel, for example.

Figures 9A, 9B, 9C:
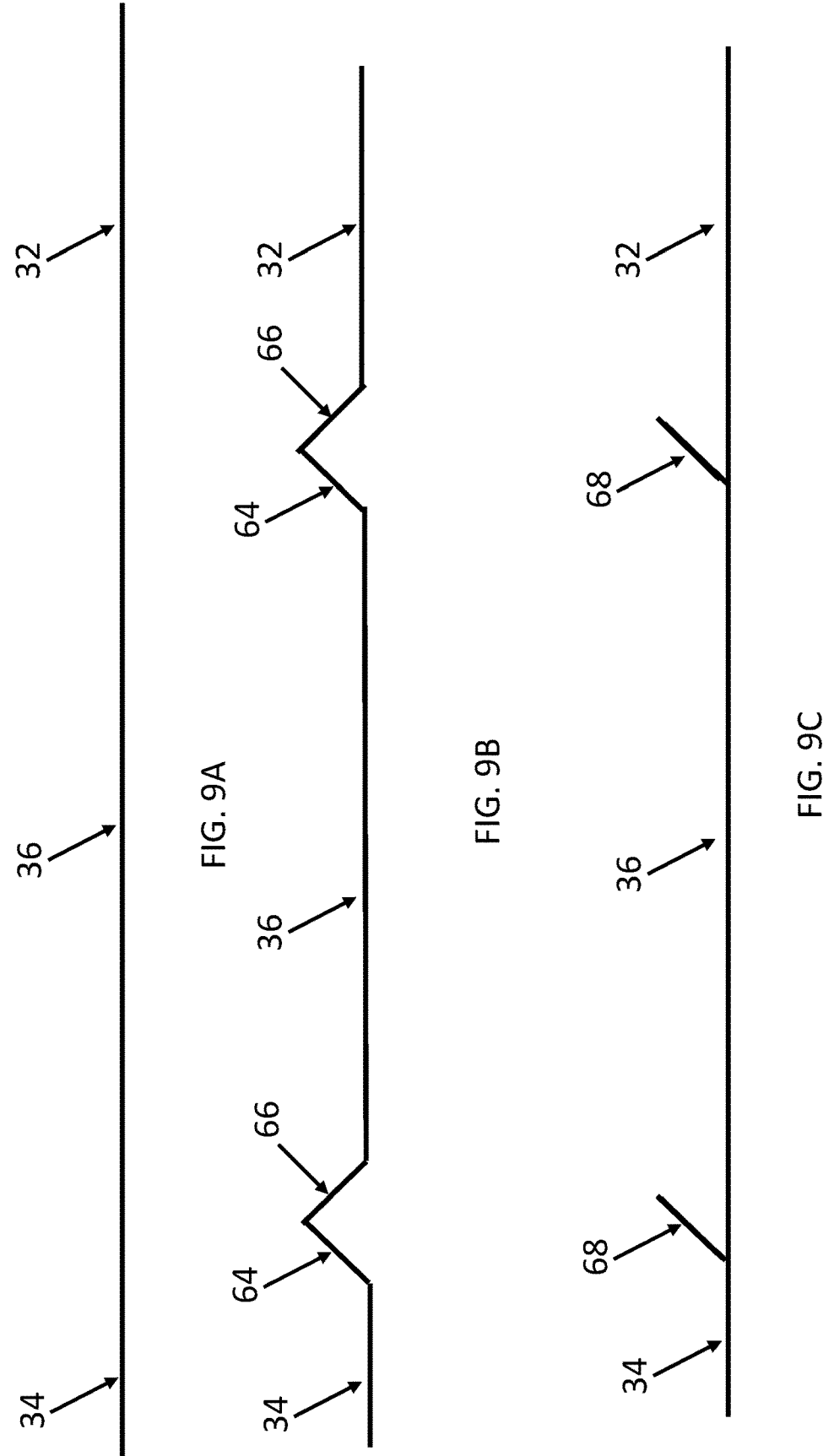
FIG. 9A is an example side view of the package material of FIG. 2G.
FIG. 9B is an example of a fold being formed in the package material of FIG. 9A to create a first handle fold portion and a second handle fold portion.
FIG. 9C is an example handle formed from the first handle fold portion and the second handle fold portion.

FIG. 9A is an example side view of the package material of FIG. 2G. FIG. 9B is an example of a fold being formed in the package material of FIG. 9A to create a first handle fold portion and a second handle fold portion. FIG. 9C is an example handle formed from the first handle fold portion being joined, sealed, seamed, and/or bonded to the second handle fold portion. Referring generally to FIGS. 9A-9C, the consumer-facing panel 32, the bottom panel 36 and the back panel 34 are illustrated. The package material is folded to create a first handle fold portion 64 and a second folded portion 66. The first handle fold portion 64 and the second handle fold portion 66 are joined, sealed, seamed, and/or bonded together to form a handle 68. Although a handle 68 is illustrated as being formed in the consumer-facing panel 32 and the back panel 34, the handle 68 may only be formed in one of the consumer-facing panel 32 or the back panel 34. In an example, a handle may also be formed in the bottom panel 36, although not illustrated in FIGS. 9A-9C.

Figure 10:
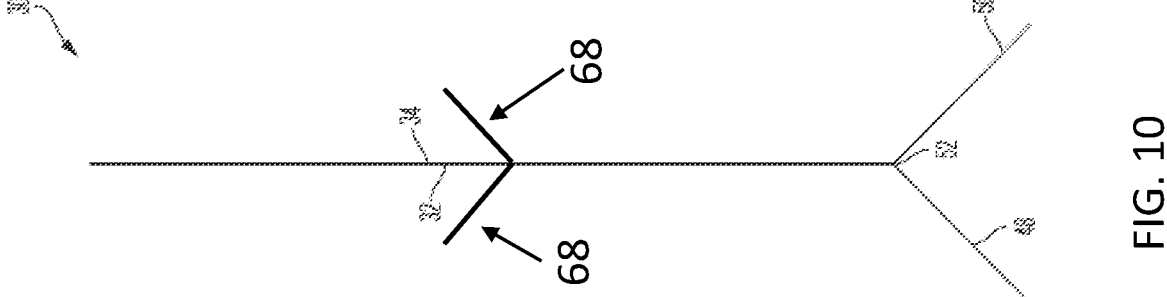
FIG. 10 is an example of the package of FIG. 2D with handles formed in the consumer-facing panel and the back panel.

FIG. 10 is an example of the package 30 of FIG. 2D with handles 68 formed in the consumer-facing panel 32 and the back panel 34. Although the handles 68 are illustrated extending in a direction away from fold line 52, they could also extend towards fold line 52. In an example, the handle 68 on the consumer-facing panel 32 may extend towards the fold line 52 and the handle 68 on the back panel 34 may extend away from the fold line 52, or vice versa. By having the handles 68 extending in different directions, when a number of unfilled packages are placed adjacent each other on wickets, less of bulge will form in the areas of the handles compared to when the handles extend in the same direction. The one or more handles may also be folded flat to the package until a consumer grasps them to aid in shipping and distribution. In the event that the packages only have one handle 68, either on the consumer-facing panel 32 or the back panel 34, alternating bags on a wicket may have a handle extending toward the fold line 52 and a handle extending away from the fold line 52. This altering of the handle's direction of extension may reduce the size of a bulge being formed when a number of folded packages are placed on a wicket adjacent each other. The handles 68 may be placed on any portion of the consumer-facing 32 and the back panels 34, such as at or towards the top, at or towards the bottom, and/or in the middle.

Figure 11:
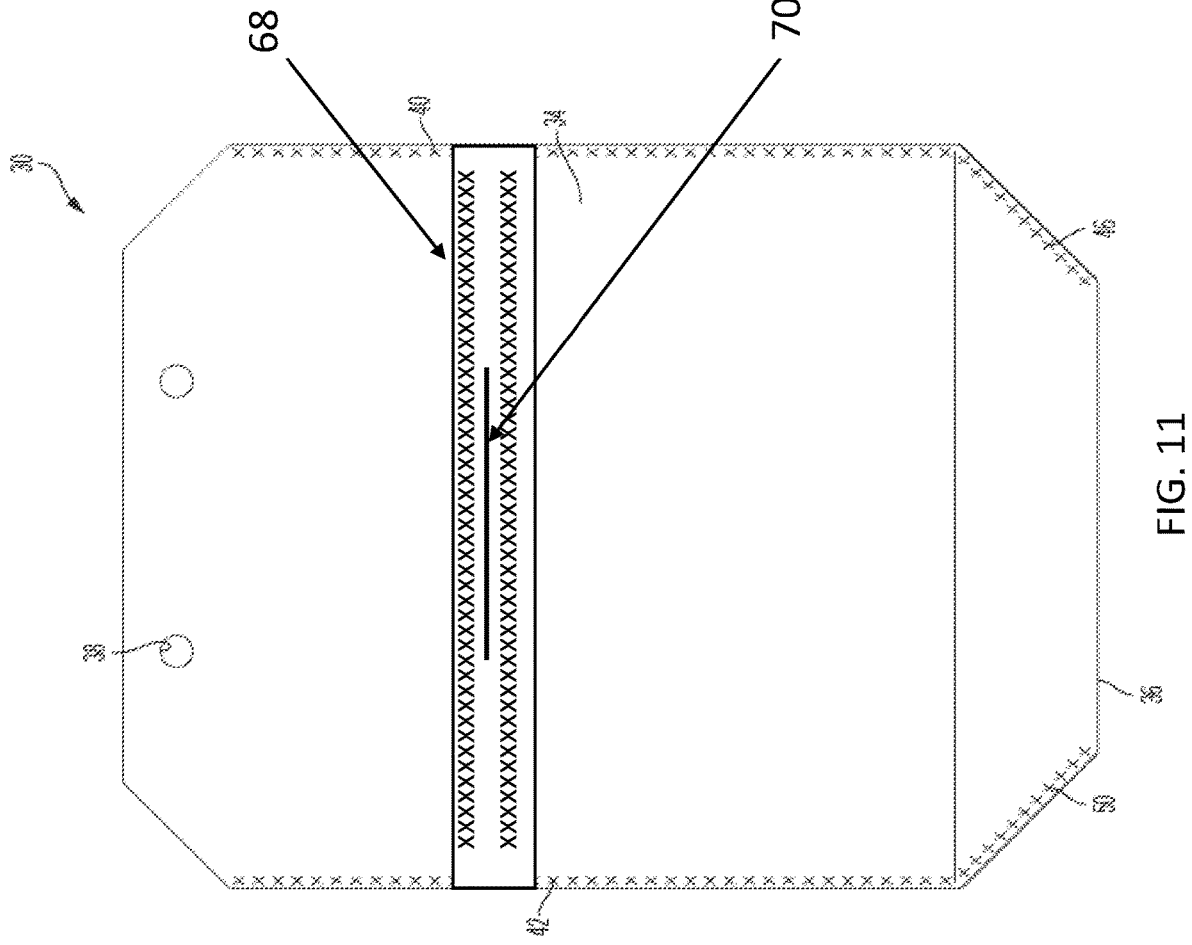
FIG. 11 is a back view of the package with a handle.

FIG. 11 is a back view of a package 30 with a handle 68. A front view of the package 30 would be similar if a handle is provided on the consumer-facing panel 32. In FIG. 11 it is illustrated how the first handle fold portion 64 is sealed or bonded (indicated by X's in FIG. 11) to the second handle fold portion 66. The sealing may be accomplished in the same or a similar way as the various seams discussed herein, such as scams 40, 42, 46, or 50, for example. A slit or slot 70 may be cut or perforated into the handle 68 to form an opening through which a consumer's fingers may slide to grasp the package 30 by the handle 68.

Figure 12A:
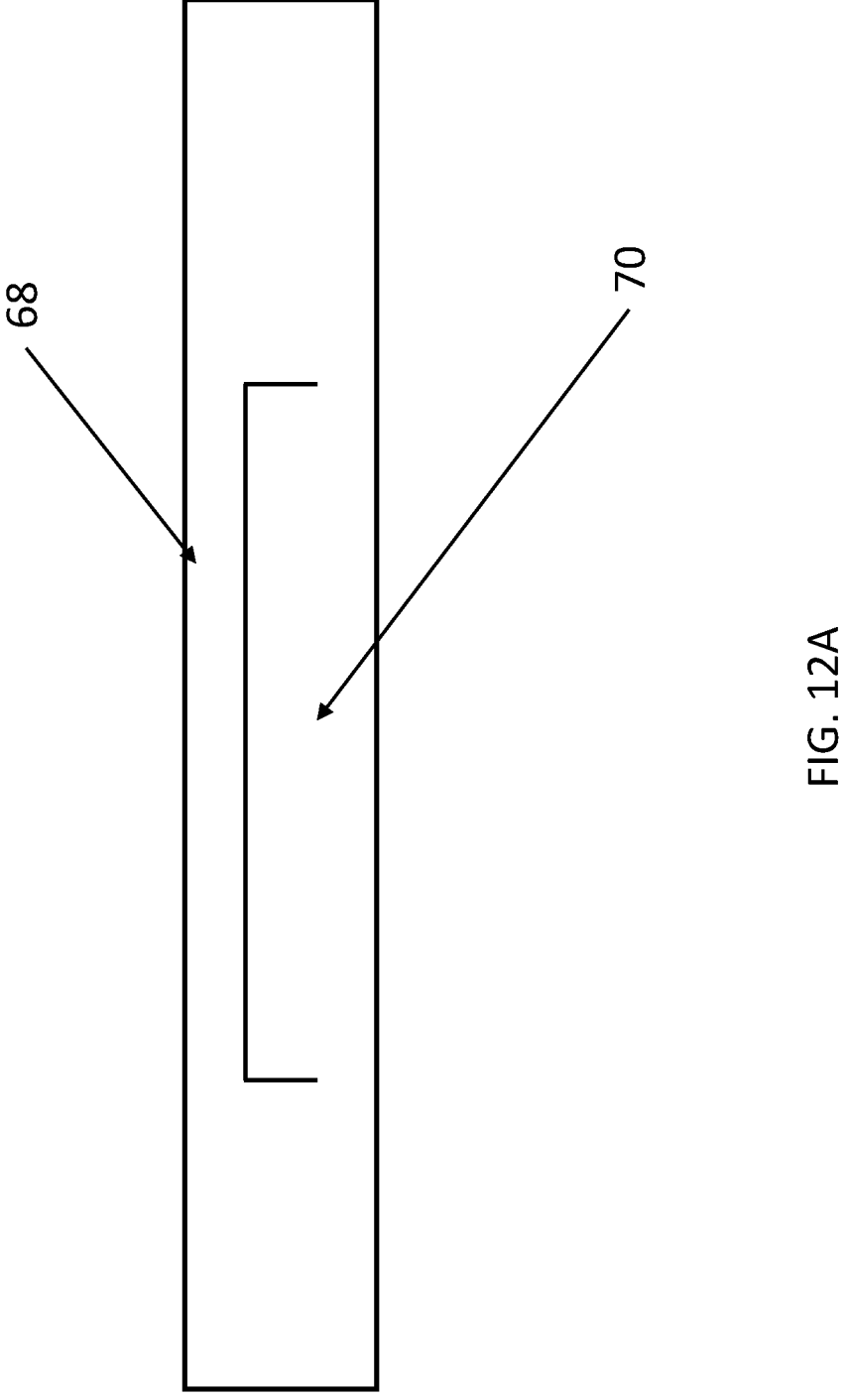
FIG. 12A illustrates a handle with a U-shaped slit or slot that is cut or perforated to form an opening through which a consumer's fingers may slide to grasp the package by the handle.
Figure 12B:
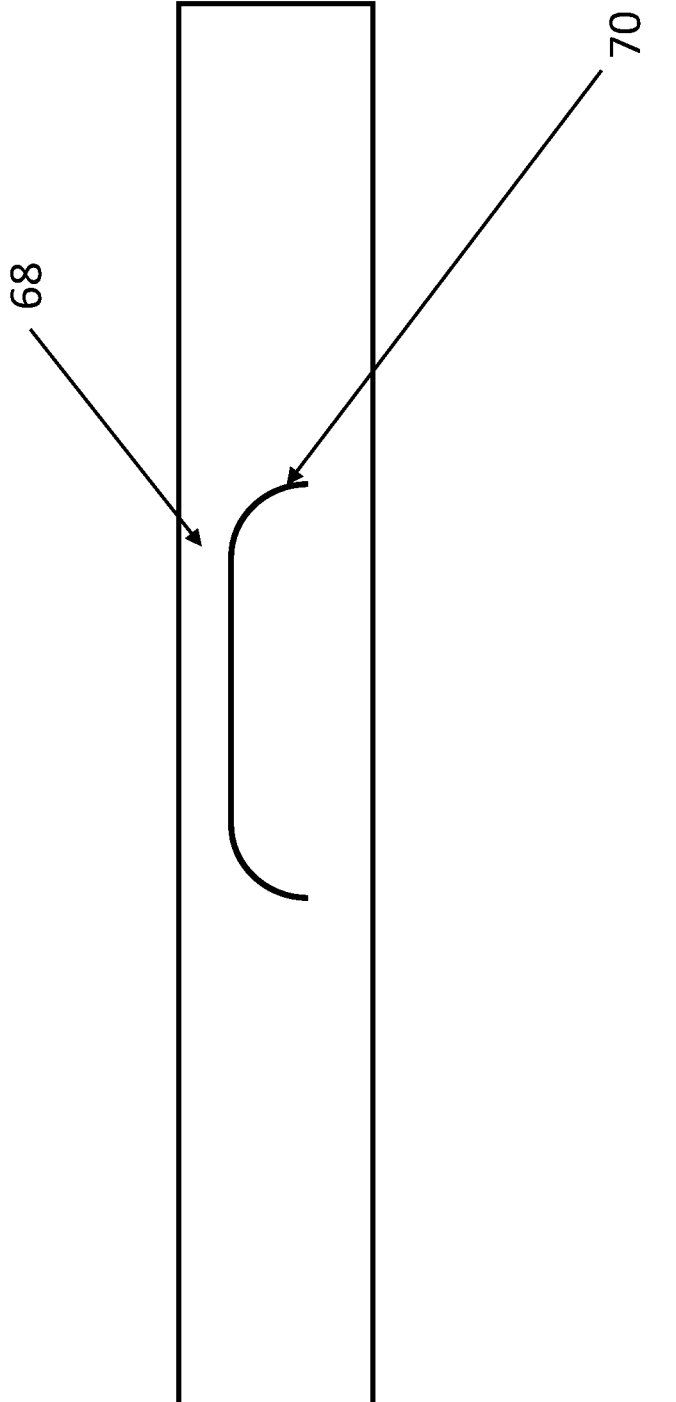
FIG. 12B illustrates a handle with a half oval shape slit or slot that is cut or perforated to form an opening through which a consumer's fingers may slide to grasp the package by the handle.
Figure 12C:
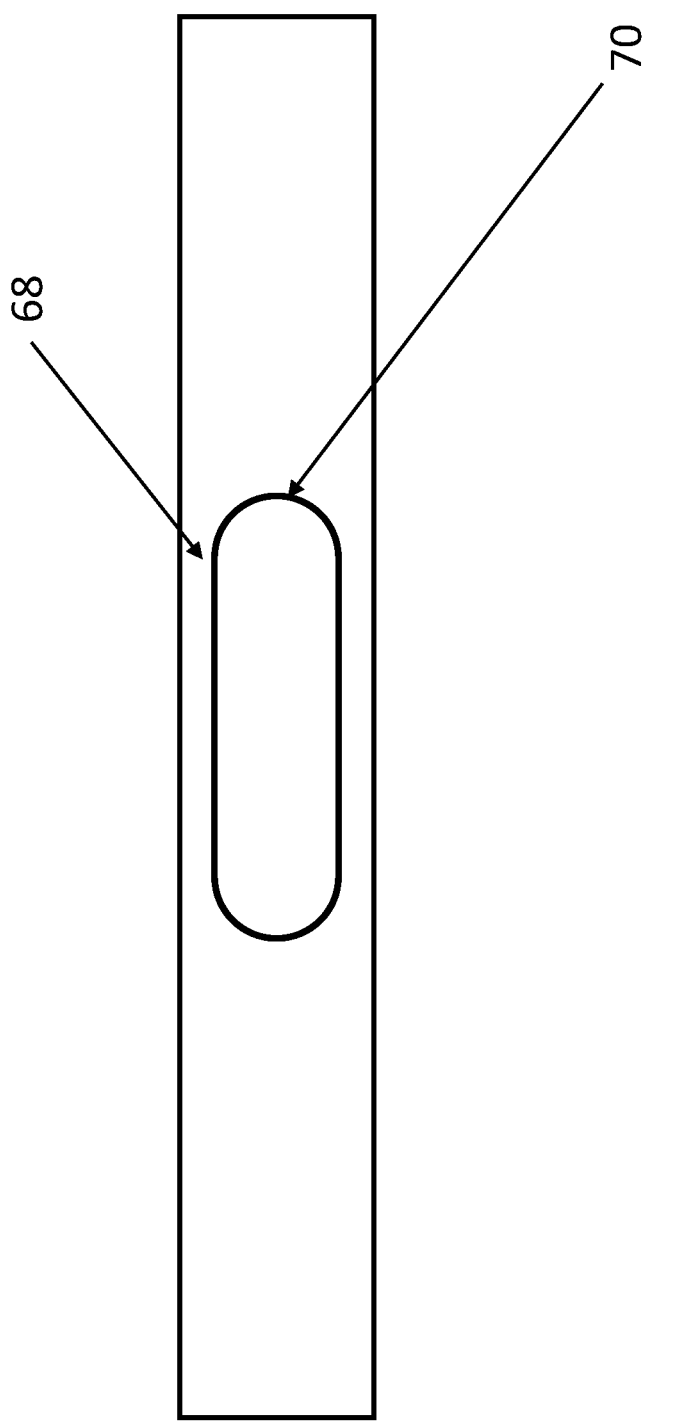
FIG. 12C illustrates a handle with an oval shaped slit or slot that is cut or perforated to form an opening through which a consumer's fingers may slide to grasp the package by the handle.
Figure 12D:
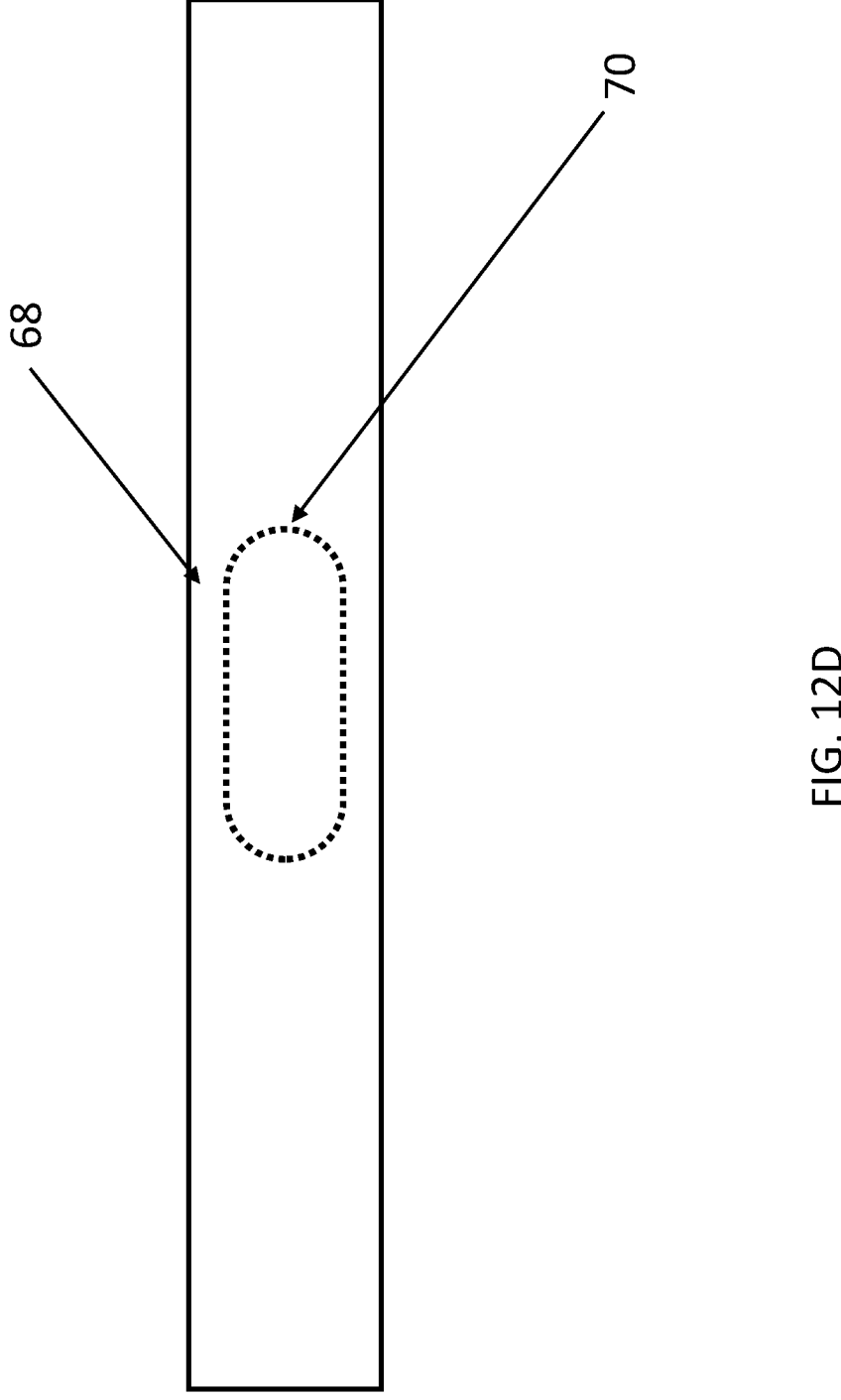
FIG. 12D illustrates a handle with an oval shaped slit or slot that is perforated to form an opening through which a consumer's fingers may slide to grasp the package by the handle.

FIG. 12A illustrates a handle 68 with a U-shaped slit or slot 70 that is cut or perforated to form an opening through which a consumer's fingers may slide to grasp the package 30 by the handle 68. FIG. 12B illustrates a handle 68 with a half oval shape slit or slot 70 that is cut or perforated to form an opening through which a consumer's fingers may slide to grasp the package by the handle 68. FIG. 12C illustrates a handle 68 with an oval shaped slit or slot 70 that is cut or perforated to form an opening through which a consumer's fingers may slide to grasp the package by the handle 68. FIG. 12D illustrates a handle 68 with an oval shaped slit or slot 70 that is perforated to form an opening through which a consumer's fingers may slide to grasp the package by the handle 68. Portions of, or all of, the slit or slot 70 (in any configuration) may be perforated, cut, and/or scored. For example, a first portion of the slit or slot 70 may be perforated while a second portion may be cut or scored. The handles 68 of FIGS. 12A-12D are illustrated without the remainder of the package and without any trim removed for simplicity. Trim removal is optional. The slit or slot 70 may have other configurations as well, such as a cut out circle, rectangle, trapezoid, or curved slit or slot, for example.

Figure 13:
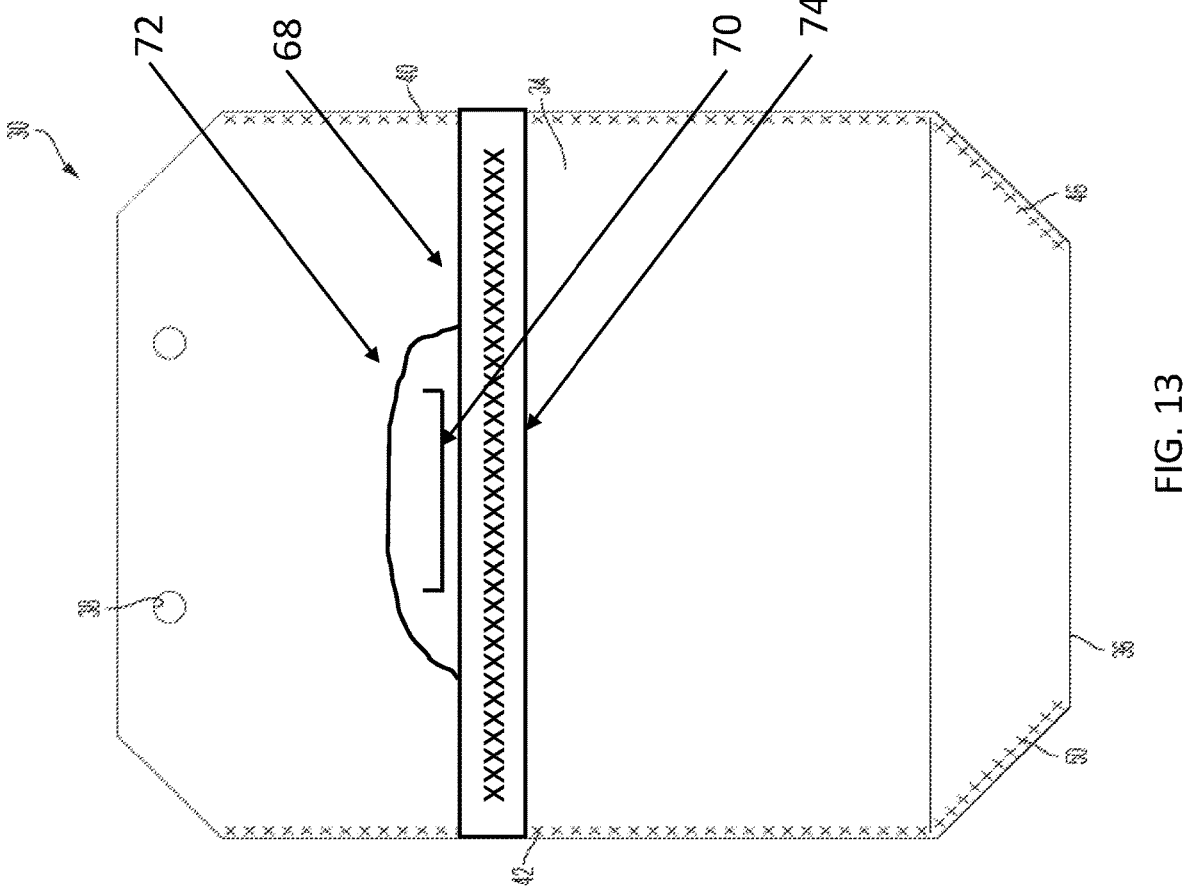
FIG. 13 is a back view of a package with a handle.

FIG. 13 is a back view of a package with a handle. FIG. 13 illustrates a handle 68 similar to FIG. 12A, but where trim is cut away to leave only a handle portion 72 extending from a base 74 of the handle 68 and with the slit or slot 70 formed in the opposite direction. The base 74 is left intact to provide strength to the handle 68. The base 74 and the handle portion 72 are formed of the first handle fold portion 64 and the second handle fold portion 66 which are sealed, seamed, joined, and/or bonded together. The trim may be cut away by a laser or other suitable methods. Any suitable portion of the trim may be removed for aesthetic or other reasons.

Test Methods

ISO 1924-3—Tensile Properties (Tensile Strength, Stretch, Energy Absorption)

The tensile properties (tensile strength, stretch and energy absorption) of a test sample are calculated from measured force and elongation values obtained using a constant rate of elongation test until the sample breaks. The test is run in accordance with compendial method ISO 1924-3, with modifications noted herein. Measurements are made on a constant rate of extension tensile tester using a load cell for which the forces measured are within 1% to 99% of the limit of the cell. A suitable instrument is the MTS Alliance using Test Suite Software, available from MTS Systems Corp., Eden Prairie, MN, or equivalent. All measurements are performed in a laboratory maintained at 23° C.±2° C. and 50%±2% relative humidity and test samples are conditioned in this environment for at least 2 hours prior to testing.

Measurements are made on both MD (machine direction) and CD (cross direction) test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample is cut to a width of 25.4 mm with a length that can accommodate a test span of 50.8 mm. The long side of the sample is parallel to the direction of interest (MD, CD). Normally in finished packages, the MD runs from the bottom to the top of the package, but this can be verified by determining the fiber orientation if in doubt. Ten replicate test samples should be prepared from the MD and ten additional replicates from the CD.

Program the tensile tester for a constant rate of extension uniaxial elongation to break as follows. Set the gauge length (test span) to 50.8 mm using a calibrated gauge block and zero the crosshead. Insert the test sample into the grips such that the long side is centered and parallel to the central pull axis of the tensile tester. Raise the crosshead at a rate of 25.4 mm/min until the test sample breaks, collecting force (N) and extension (mm) data at 100 Hz throughout the test. Construct a graph of force (N) versus extension (mm). Read the maximum force (N) from the graph and record as Peak Force to the nearest 0.1 N, noting MD or CD. Read the extension at the maximum force (N) from the graph and record as Elongation at Break to the nearest 0.01 mm, noting MD or CD. From the graph, determine the point (z) where the tangent to the curve, with a slope equal to the maximum slope of the curve, intersects the elongation axis. Now calculate the area under the force vs elongation curve from point z up to the point of maximum force and report to the nearest 0.1 mJ, noting MD or CD. [Refer to FIG. 2 in ISO 1924-3 for a depiction of a typical force vs elongation curve where point z is denoted.]

Calculate the arithmetic mean Peak Force for all MD replicates and then all CD replicates and record respectively as Mean MD Peak Force and Mean CD Peak Force to the nearest 0.1 N. Calculate the arithmetic mean Elongation at Break for all MD replicates and then all CD replicates and record respectively as Mean MD Elongation at Break and Mean CD Elongation at Break to the nearest 0.01 mm. Calculate the arithmetic mean area under the force vs elongation curve for all MD replicates and then all CD replicates and record respectively as Mean Area Under MD Curve and Mean Area Under CD Curve to the nearest 0.1 mJ.

Tensile strength is calculated by dividing the Mean Peak Force (N) by the width of the test sample (25.4 mm). Calculate the tensile strength for the MD replicates and then the CD replicates and report respectively as MD Tensile Strength and CD Tensile Strength to the nearest 0.1 kN/m.

Stretch at break is calculated by dividing the Mean Elongation at Break (mm) by the initial test length (test span) of 50.8 mm, and then multiplying by 100. Calculate the stretch at break for the MD replicates and then the CD replicates and report respectively as MD Stretch at Break and CD Stretch at Break to the nearest percent.

ISO 2758—Burst Strength

Burst strength is the maximum uniformly distributed pressure that a test sample can withstand. Burst strength is measured in accordance with compendial method ISO 2758 using a test apparatus as described within the method. A suitable instrument is the 13-60 Burst Tester for Paper and Foils available from Testing Machines, Inc (New Castle, DE), or equivalent. The instrument is calibrated and operated as per the manufacturer's instructions. All measurements are performed in a laboratory maintained at 23° C.+/−2° C. and 50%+/−2% relative humidity, and test samples are conditioned in this environment for at least 2 hours prior to testing.

Measurements are made on test samples taken from rolls or sheets of the raw material, or test specimens obtained from a finished package. When excising a test sample from a finished package, use care to not impart any contamination or distortion to the test sample during the process. The test sample must be larger than the clamps used to hold the test sample in the instrument. The test sample should be taken from an area free of folds, wrinkles or seams.

Measure the burst strength (using a clamping pressure sufficient to prevent slippage during the test, and a pumping rate of 95±15 mL/min) for a total of 10 replicate test samples. For samples that are sided, the side of the test sample that is meant to face the inside of the package faces the pressure when placed into the clamps, and 10 replicates are tested in this orientation. For samples that are balanced (not sided), 5 replicates are tested with the inside of the package facing the pressure and 5 replicates are tested with the outside of the package facing the pressure, and the results are averaged together. Record the pressure at which each test sample bursts to the nearest 0.001 kPa. If the burst pressure is less than 70 kPa, multiple layers of the test material must be used. To obtain the burst strength, divide the burst pressure by the number of layers tested. Calculate the arithmetic mean burst pressure for all replicates and report as Burst Strength to the nearest 0.001 kPa.

ISO 534—Caliper

The caliper, or thickness, of a single-layer test sample is measured under a static load by a micrometer, in accordance with compendial method ISO 534, with modifications noted herein. All measurements are performed in a laboratory maintained at 23° C.±2° C. and 50%±2% relative humidity and test samples are conditioned in this environment for at least 2 hours prior to testing.

Caliper is measured with a micrometer equipped with a pressure foot capable of exerting a steady pressure of 70 kPa±0.05 kPa onto the test sample. The micrometer is a dead-weight type instrument with readings accurate to 0.1 micron. A suitable instrument is the TMI Digital Micrometer Model 49-56, available from Testing Machines Inc., New Castle, DE, or equivalent. The pressure foot is a flat ground circular movable face with a diameter that is smaller than the test specimen and capable of exerting the required pressure. A suitable pressure foot has a diameter of 16.0 mm. The test sample is supported by a horizontal flat reference platform that is larger than and parallel to the surface of the pressure foot. The system is calibrated and operated per the manufacturer's instructions.

Measurements are made on single-layer test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample is ideally 200 mm$^2$ and must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm per second until the full pressure is exerted onto the test sample. Wait 5 seconds and then record the caliper of the test sample to the nearest 0.1 micron. In like fashion, repeat for a total of ten replicate test samples. Calculate the arithmetic mean for all caliper measurements and report the value as Caliper to the nearest 0.1 micron.

ISO 536—Basis Weight

The basis weight of a test sample is the mass (in grams) per unit area (in square meters) of a single layer of material and is measured in accordance with compendial method ISO 536. The mass of the test sample is cut to a known area, and the mass of the sample is determined using an analytical balance accurate to 0.0001 grams. All measurements are performed in a laboratory maintained at 23° C.±2° C. and 50%±2% relative humidity and test samples are conditioned in this environment for at least 2 hours prior to testing.

Measurements are made on test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample must be as large as possible so that any inherent material variability is accounted for.

Measure the dimensions of the single layer test sample using a calibrated steel metal ruler traceable to NIST, or equivalent. Calculate the Area of the test sample and record to the nearest 0.0001 square meter. Use an analytical balance to obtain the Mass of the test sample and record to the nearest 0.0001 gram. Calculate Basis Weight by dividing Mass (in grams) by Area (in square meters) and record to the nearest 0.01 grams per square meter (gsm). In like fashion, repeat for a total of ten replicate test samples. Calculate the arithmetic mean for Basis Weight and report to the nearest 0.01 grams/square meter.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 5). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Percentage of Colorant Coverage Measurement Method

The Percentage of Colorant Coverage measurement method measures the percent area of colorant coverage on a package panel. A flatbed scanner capable of scanning a minimum of 24 bit color at 800 dpi with manual control of color management (a suitable scanner is an Epson Perfection V750 Pro from Epson America Inc., Long Beach CA, or equivalent) is used to acquire images. The scanner is interfaced with a computer running color calibration software capable of calibrating the scanner against a color reflection IT8 target utilizing a corresponding reference file compliant with ANSI method IT8.7/2-1993 (suitable color calibration software is Monaco EZColor or i1Studio available from X-Rite Grand Rapids, MI, or equivalent). The color calibration software constructs an International Color Consortium (ICC) color profile for the scanner, which is used to color correct an output image using an image acquisition program that supports application of ICC profiles. The color corrected image is then segmented via color thresholding using color analysis software (a suitable image color analysis software is MATLAB R2017b available from The Mathworks, Inc., Natick, MA).

The samples are conditioned at about 23° C.±2° C. and about 50%±2% relative humidity for 2 hours prior to testing.

The scanner is turned on 30 minutes prior to calibration and image acquisition. Deselect any automatic color correction or color management options that may be included in the scanner software. If the automatic color management cannot be disabled, the scanner is not appropriate for this application. The recommended procedures of the color calibration software are followed to create and export an ICC color profile for the scanner. The color calibration software compares an acquired IT8 target image to a corresponding reference file to create and export the ICC color profile for a scanner, which will be applied within the image analysis program to correct the color of subsequent output images.

A sample is obtained from a package or package materials with identified panels. A single panel is selected and cut along its perimeter to remove it for testing. Panels selected for testing should not contain tears or wrinkles.

The scanner lid is opened, and the sample carefully laid flat on the center of the scanner glass with the colored surface oriented toward the glass. A scan containing a panel region is acquired at 24 bit color with a resolution of 800 dpi (approximately 31.5 pixels per mm) in reflectance mode. The ICC color profile is assigned to the image producing a color corrected sRGB image. This calibrated image is saved in an uncompressed format to retain the calibrated R, G, B color values, such as a TIFF file, prior to analysis.

The calibrated image is opened in the color analysis software. The image is smoothed using a 2D Gaussian filter with a sigma of 3 to blur out any individual dots of colorant. Next, utilizing a color thresholding program, a color space to perform the color thresholding is selected, for example CIELAB with its three color values L*, a*, b*. Then a region of interest (ROI) boundary is manually drawn within a visibly discernable region of only the base color, without any colorants present, to identify its color space values. A panel with no visible base color region will be deemed to have 100% colorant coverage. The thresholding levels in all three channels of the selected color space are then manually adjusted to segment the regions of the panel that contain colorant coverage from those regions of the base color. The area of the panel containing colorant coverage is measured and the percentage of the area of the panel containing colorant coverage is calculated and recorded to the nearest whole percent.

In like manner, prepare, scan and analyze six replicate package panels. Calculate and report the arithmetic mean of the measured percent area of colorant coverage values to the nearest whole percent.

Humidity Barrier Rapid Test (HuBa Test)

The Humidity Barrier Rapid Test (HuBa Test) is used to assess the barrier properties of a sample package material. Specifically, package material raw material available as roll stock, or alternatively a package material excised from a finished product package, is used as a barrier surface of a test container placed inside a climate-controlled chamber. The time at which the environment of the container achieves quasi-equilibrium with the environment of the climate-controlled chamber is measured and reported as the HuBa parameter.

In this method, a polypropylene food storage container (hereafter the "test container") having a body and detachable lid and having an airtight seal is used to define a test volume. The detachable lid of the test container is modified so as to create a rectangular opening in the lid. An operating, untethered data logger is placed in this container. In the laboratory environment, a specimen of package material being characterized is stacked between the lid and body of the test container so as to create a barrier surface of defined area (but sealed at the edges). The closed test container assembly is then placed in a climate-controlled chamber at a temperature and relative humidity elevated from the ambient laboratory level. After 48 hours, the test container assembly is then removed from the climate chamber, and the data logger memory is retrieved and read so as to a establish relative humidity vs. time data trace. The time at which a quasi-equilibrium plateau (associated with the setpoint of the climate-controlled chamber) is reached is the HuBa parameter.

Materials and Apparatus

The test container used is formed from polypropylene, is approximately 2.6 L in volume, and measures 248 mm in length by 180 mm in width by 93 mm in depth. The removable lid's dimensions are 248 mm in length by 180 mm dimensions in width. The preferred test container is food storage container LocknLock PP Classic Vorratsdose HPL826, LocknLock Co., Scoul, Republic of Korea, or equivalent. Suitable alternative test containers must have an airtight seal and generally involve a positive snap closure, be 2.6±0.2 L in volume, and have lid area that is 446±30 cm². The lid of the test container is modified by cutting and removing a centered rectangle that is approximately 80% of the area of the lid so as to leave a bezel of approximately uniform dimension at least about 20 mm wide around the entirety of the lid.

A suitable untethered temperature and relative humidity data logger is one with % RH accuracy within 5%, range of 0% RH to 100% RH, temp range of 20° C. to 85° C., and able to sample and record once per minute for at least 48 hours. One example of a suitable data logger is the iButton DS1923, Analog Devices, Wilmington, MA, USA, or equivalent.

A suitable climate-controlled chamber is at least 250 L in volume and must be capable of controlling temperature within ±2° C. and ±2% RH over the range of 20° C. to 70° C. and 10% RH to 80% RH. An example suitable climate-controlled chamber is Model KBF 720 humidity test chamber, Binder Inc., Bohemia, NY, USA. The chamber is maintained at 50° C. and 75% RH prior to and throughout the entirety of the test.

Sampling and Setup

All package material is equilibrated for at least 24 hours to a laboratory environment of 23±2° C. and 50±5% RH, and this same environment is used for the laboratory ambient environment throughout. It is preferable to assess at least five like specimens of a package material, but as few as one specimen may be characterized. Package material to be assessed is preferably taken from raw material roll stock or unfilled flat bags, if available. In the case of roll stock, like specimens that are at least 1 cm longer and wider in each dimension as the lid of the test container are excised from the roll stock. In the case of unfilled flat bags, specimens of package material are cut so as to again be at least 1 cm longer and wider in each dimension as the lid of the test container, and the excised portions are taken to as to avoid (or if this is not possible to minimize) the inclusion of bonds, scams, or other disruptions in an otherwise, continuous, uniform extent of package material. If relevant roll stock or unfilled bag package material is not available, like specimens are cut from relevant areas of finished product packages of absorbent articles. Specimens of package material are again at least 1 cm longer and wider in each dimension as the lid of the test container, and the excised portions are taken to as to avoid (or if this is not possible to minimize) the inclusion of bonds, seams, or other disruptions in an otherwise, continuous, uniform extent of package material. In any of the above cases, specimens may be more than 1 cm longer than each of the length and the width of the lid so long as this extra material does not interfere with the positive closure of the test container. If the test container is such that specimens only 1 cm longer or wider than the lid interfere with the positive closure of the test container, the test container is not appropriate for this method, and an alternative test container allowing for 1 cm of specimen overlap must be used.

The data logger, configured to collect one temperature and percent relative humidity datum per minute, is triggered, and is then immediately placed in the body of the test container. One specimen of package material is placed centered on the opening of the test container followed by closure with the modified lid so as to create a seal with the package material around the edge of the test container, and the entire test container assembly is introduced into the climate-controlled chamber.

Measurement, Analysis, and Reporting

After 48 hours, the test container with a specimen of package material is removed from the climate-controlled chamber, and the data logger is retrieved, stopped, and read in order to establish both a % RH vs time trace and a temperature vs time trace. Qualitatively, during this period of time relative humidity reaches a quasi-equilibrium with the climate-controlled chamber, which corresponds to a plateau region of the % RH vs time trace. (If experience with a given material justifies removal prior to 48 hours, this is permissible, though the specimen is discarded and replaced with an additional like replicate in the event that it is discovered ex post facto that that expected quasi-equilibration point had not yet, in fact, been reached at time of removal.)

The analysis of the % RH vs time trace involves several steps. First, any artifact at the end of the trace that by inspection corresponds to the removal of the test container from the climate-controlled chamber or the data logger from the test container are removed so that the % RH vs time trace terminates on a plateau or upslope. Second, the first point at which the temperature exceeds 35° C. in the temperature vs time trace is deemed to be time zero, and the time axis for both the % RH vs time trace and the temperature vs time trace is shifted and absolute time defined so that zero corresponds to this point. Third, if a quasi-equilibrium plateau is visible, the approximate range of time corresponding to this time is noted, and the latter 50 percent of this time span is used to define an average plateau % RH by calculating the arithmetic mean of all % RH points in this latter span and recording it to the nearest 0.1% RH. (Because of absolute error that may be present in both the climate chamber's relative humidity setpoint and in the data logger itself, it is noted that the quasi-equilibrium plateau may not occur at exactly 75% RH. The presence and location in time of the plateau—and not its absolute value—is used in this analysis.) If no terminal plateau is visible within the 48 hour test, the analysis is terminated at this point and the HuBa parameter of the specimen is deemed to be 48.0 hours. Fourth, in the case that a plateau is observed, this average plateau value is multiplied by 0.99 and is recorded to the nearest 0.1% RH as the "plateau threshold value." Fifth, the % RH vs time trace is smoothed by applying a moving, ten-minute windowed average to the % RH data. Finally, in the case that a plateau is observed the first time in the overall % RH vs time trace at which the measured % RH exceeds the plateau threshold value is deemed to be HuBa parameter for the specimen being measured. The HuBa parameter for the specimen is recorded in hours to the nearest 0.1 hour.

The arithmetic mean of the HuBa parameters for each of specimens measured is the HuBa parameter for the package material being assessed and is reported in hours to the nearest 0.1 hour.

ASTM F88-06—Seal Tensile Strength Test

This test method determines the strength of a vertical side seal or seam or angled side seal or seam or side seam or seal in flexible packaging materials by measuring the force required to separate a test strip of material containing the seal. Seal strength is measured in accordance with compendial method ASTM F0088-06 on a constant rate of extension tensile tester, with procedural specifics noted herein. A suitable instrument is the Instron Model 5965 using Bluehill Universal Software, both available from Instron Norwood, Mass. or Zwick/Roell Materials Testing Machine Allround Tabletop Z010" using Zwick/Roell TestExpert V3 Software, or equivalent. All measurements are performed in a laboratory maintained at 23° C.±2° C. and 50%±2% relative humidity and test samples are conditioned in this environment for 2 hours prior to testing.

The preparation of the test specimens and test procedure is described in the referenced ASTM method, with the following specific details. The test specimen is cut to a width of 15 mm, the grip separation rate is 500 mm/min, and the tail-holding method is unsupported. The maximum force encountered as the test specimen is stressed to failure is recorded as force per unit width to the nearest 0.1 N/15 mm. The test is repeated for a total of at least three replicate test specimens. Calculate the arithmetic mean for maximum seal strength and report as Tensile Strength to the nearest 0.1N/ 15 mm.

Examples/Combinations

Aspect 1:

1. A package of one or more absorbent articles, the package comprising a package material, wherein the package material comprises natural fibers, wherein the package comprises a plurality of panels comprising a consumer-facing panel, wherein the package is scaled such that the one or more absorbent articles are enclosed therein;

wherein the package material exhibits a HuBa value of greater than about 5 hours, according to HuBa Test;

wherein the package is recyclable;

the package comprising a vertical side seal having a side seal strength, wherein the side seal strength is greater than about 5.1 N/15 mm to about 15 N/15 mm, according to the Seal Tensile Strength Test;

wherein the package material comprises a barrier film;

wherein the barrier film comprises a first layer most proximate to the natural fibers and a second layer most distal from the natural fibers;

wherein the first layer comprises a first polymer material;

wherein the second layer comprises a second polymer material; and wherein the first polymer material is different than the second polymer material.

2. The package of paragraph 1, wherein the first layer comprises high-density polyethylene in contact with the natural fibers.

3. The package according to paragraph 1 or 2, wherein the second layer comprises low-density polyethylene, and wherein the second layer is in contact with the first layer.

4. The package according to paragraph 3, wherein the first layer and the second layer are co-extruded.

5. The package according to any one of the preceding paragraphs, wherein a portion of an outer surface of the package material comprises a heat sealable lacquer, adhesive, and/or polymer.

6. The package according to any one of the preceding paragraphs, wherein the first and second layers are 20 weight percent or less of the package material.

7. The package according to any one of the preceding paragraphs, wherein the first and second layers are 10 weight percent or less, 5 weight percent or less, 4 weight percent or less, or 3 weight percent or less, but at least 1 weight percent of the package material.

8. The package according to any one of the preceding paragraphs, wherein each of the one or more absorbent articles comprise superabsorbent polymers (SAP) in an amount of greater than about 5 grams.

9. The package according to any one of the preceding paragraphs, wherein the package exhibits a recyclable paper percentage of at least 80 percent.

10. The package according to any one of paragraphs 1-8, wherein the package exhibits a recyclable paper percentage of between about 60 percent to about 99.9 percent.

11. The package according to any one of the preceding paragraphs, wherein the package comprises at least 50 percent by weight of the natural fibers.

12. The package according to any one of the preceding paragraphs, wherein the package material comprises about 70 percent to about 99 percent by weight of the natural fibers.

13. The package according to any one of the preceding paragraphs, wherein the natural fibers comprise wood fibers or pulp fibers.

14. The package according to any one of the preceding paragraphs, wherein the package material exhibits a HuBa value of about 5 hours to about 20 hours, preferably about 5.3 hours to about 15 hours, more preferably about 5.3 hours to about 12 hours, according to the HuBa Test.

15. The package according to any one of the preceding paragraphs, wherein the package is substantially free of adhesive.

16. The package according to any one of the preceding paragraphs, wherein the one or more absorbent articles within the package comprise taped diapers, pants, or adult incontinence products.

17. The package according to any one of the preceding paragraphs, wherein the each of the one or more absorbent articles comprise a substantially unactivated wetness indicator.

18. The package according to any one of the preceding paragraphs, wherein the one or more absorbent articles comprise a breathable film as a backsheet component.

19. The package according of any one of the preceding paragraphs, wherein the plurality of panels comprise the consumer-facing panel, a back panel, a left side panel, a right side panel, a bottom panel, a first top panel, and a second top panel.

20. The package of paragraph 19, wherein the consumer-facing panel, the back panel, the bottom panel, and the first and second top panels are formed of a continuous packaging material.

21. The package of paragraph 20, wherein the left side panel comprises a vertical left side seam and two angled left side seams, wherein the right panel comprises a vertical right side seam and two angled right side seams, wherein a length of the vertical left side seam is greater than a length of the two angled left side seams, and wherein a length of the vertical right side seam is greater than a length of the two angled right side seams.

22. The package of paragraph 21, wherein the consumer-facing panel has a consumer-facing panel height, and wherein the consumer-facing panel height is greater than the length of the vertical left side seam.

23. The package of paragraph 21, wherein the back panel has a back panel height, and wherein the back panel height is greater than the length of the vertical right side seam.

24. The package of paragraph 21, wherein the bottom panel is generally rectangular.

25. The package of paragraph 21, wherein the bottom panel, the consumer-facing panel, and the back panel are free of seams.

26. The package of any one of the preceding paragraphs, wherein the first polymer material comprises a polyolefin.

27. The package of any one of the preceding paragraphs, wherein the second polymer material comprises a polyolefin.

28. The package of any one of the preceding paragraphs, wherein the first polymer material and/or the second polymer material comprises PIR and/or PCR.

29. The package of any one of the preceding paragraphs, wherein the natural fibers comprise PIR and/or PCR.

30. The package of any one of the preceding paragraphs, comprising a handle having a cut or perforated slit or slot therethrough, wherein the handle is integral with the package material.

Aspect 2:

1. A package of one or more absorbent articles, the package comprising a package material, wherein the package material comprises natural fibers, wherein the package comprises a plurality of panels comprising a consumer-facing panel, wherein the package is sealed such that the one or more absorbent articles are enclosed therein;

wherein the package material exhibits a HuBa value of greater than about 5.3 hours to about 20 hours, according to the HuBa Test;

wherein the package is recyclable; and wherein each of the one or more absorbent articles comprises superabsorbent polymers (SAP) in an amount of greater than about 5 grams per article.

2. The package according to paragraph 1, wherein the package material comprises a barrier film layer disposed on an inner surface of the package material.

3. The package according to paragraph 2, wherein the barrier film layer comprises low density polyethylene.

4. The package according to paragraph 2, wherein the barrier film layer comprises a first layer and a second layer, wherein the first layer comprises a first polyolefin material in contact the natural fibers, wherein the second layer comprises a second polyolefin material, wherein the first polyolefin material is different than the second polyolefin material, wherein the second layer is in contact with the first layer, and wherein the second layer only overlaps about 5% to about 35% of the first layer.

5. The package of paragraph 4, wherein the first layer comprises high-density polyethylene.

6. The package according to paragraph 5, wherein the second layer comprises low-density polyethylene.

7. The package according to paragraph 4, wherein the first layer and the second layer are co-extruded.

8. The package according to any one of the preceding paragraphs, wherein a portion of an outer surface of the package material comprises a heat sealable lacquer, adhesive, and/or polymer.

9. The package according to any one of the preceding paragraphs, wherein the package comprises a vertical side seal having a side seal strength, wherein the side seal strength is greater than about 5.1 N/15 mm to about 15 N/15 mm, according to Seal Tensile Strength Test.

10. The package according to any one of paragraphs 4-9, wherein the first and second layers are 20 weight percent or less of the package material.

11. The package according to any one of paragraphs 4-9, wherein the first and second layers are 10 weight percent or less, 5 weight percent or less, 4 weight percent or less, or 3 weight percent or less, but at least 1 weight percent of the package material.

12. The package according to any one of the preceding paragraphs, wherein the package exhibits a recyclable paper percentage of at least 80 percent.

13. The package according to any one of the preceding paragraphs, wherein the package exhibits a recyclable paper percentage of between about 60 percent to about 99.9 percent.

14. The package according to any one of the preceding paragraphs, wherein the package material comprises at least 50 percent by weight of the natural fibers.

15. The package according to any one of the preceding paragraphs, wherein the package material comprises about 70 percent to about 99 percent by weight of the natural fibers.

16. The package according to any one of the preceding paragraphs, wherein the natural fibers comprise wood fibers or pulp fibers.

17. The package according to any one of the preceding paragraphs, wherein the package material exhibits a HuBa value of about 5.3 hours to about 12 hours, according to the HuBa Test.

18. The package according to any one of the preceding paragraphs, wherein the package is substantially free of adhesive.

19. The package according to any one of the preceding paragraphs, wherein the one or more absorbent articles within the package comprise taped diapers, pants, or adult incontinence products.

20. The package according to any one of the preceding paragraphs, wherein each of the one or more absorbent articles comprises a substantially unactivated wetness indicator.

21. The package of according to any one of the preceding paragraphs, wherein the one or more absorbent articles comprise a breathable film as a backsheet component.

22. The package according of any one of the preceding paragraphs, wherein the plurality of panels comprise the consumer-facing panel, a back panel, a left side panel, a right side panel, a bottom panel, a first top panel, and a second top panel.

23. The package of paragraph 22, wherein the consumer-facing panel, the back panel, the bottom panel, and the first and second top panels are formed of a continuous packaging material.

24. The package of paragraph 23, wherein the left side panel comprises a vertical left side seam and two angled left side seams, wherein the right panel comprises a vertical right side seam and two angled right side seams, wherein a length of the vertical left side seam is greater than a length of the two angled left side seams, and wherein a length of the vertical right side seam is greater than a length of the two angled right side seams.

25. The package of paragraph 24, wherein the consumer-facing panel has a consumer-facing panel height, and wherein the consumer-facing panel height is greater than the length of the vertical left side seam.

26. The package of paragraph 24, wherein the back panel has a back panel height, and wherein the back panel height is greater than the length of the vertical right side seam.

27. The package of paragraph 22, wherein the bottom panel is generally rectangular.

28. The package of paragraph 22, wherein the bottom panel, the consumer-facing panel, and the back panel are free of seams.

29. The package of any one of the preceding paragraphs, comprising a handle having a cut or perforated slit or slot therethrough, wherein the handle is integral with the package material.

30. A package configured to receive one or more absorbent articles, the package comprising a package material;

wherein the package material comprises natural fibers, wherein the package comprises a plurality of panels comprising a consumer-facing panel and a back panel having one or more wicket holes in a portion thereof, wherein the package is configured to be sealed such that the one or more absorbent articles are enclosed therein;

wherein the back panel comprises a first chamfered side edge and a second chamfered side edge in an area proximate to the one or more wicket holes; and wherein the package is recyclable.

31. The package of paragraph 30, wherein one or more slits or lines or perforation extend outwardly from the one or more wicket holes.

32. The package of paragraph 30 or 31, comprising a handle having a cut or perforated slit or slot therethrough, wherein the handle is integral with the package material.

33. The package according to paragraph 30, wherein the package material comprises a barrier layer comprising metalized paper disposed on an inner surface of the package material.

34. The package according to paragraph 30, wherein the package material comprises a barrier layer comprising an inorganic material disposed on an inner surface of the package material.

Aspect 3:

1. A package of one or more absorbent articles, the package comprising a package material, wherein the package material comprises natural fibers, wherein the package comprises a plurality of panels comprising a consumer-facing panel, wherein the package is sealed such that the one or more absorbent articles are enclosed therein;

wherein the package material exhibits a HuBa value of greater than about 5.3 hours, according to the HuBa Test;

wherein the package is recyclable; and the package comprising a vertical side seal having a side seal strength, wherein the side seal strength is greater than about 5.1 N/15 mm and less than about 15 N/15 mm, according to Seal Tensile Strength Test.

2. The package of paragraph 1, wherein the package material comprises a barrier film layer disposed on an inner surface of the package material.

3. The package of paragraph 2, wherein the barrier film layer comprises low density polyethylene.

4. The package according to paragraph 2, wherein the barrier films comprises a first layer and a second layer, wherein the first layer comprises a first polyolefin material in contact with the natural fibers, wherein the second layer comprises a second polyolefin material, wherein the first polyolefin material is different than the second polyolefin material, and wherein the second layer is in contact with the first layer.

5. The package of paragraph 4, wherein the first layer comprises high-density polyethylene.

6. The package according to paragraph 5, wherein the second layer comprises low-density polyethylene.

7. The package according to paragraph 4, wherein the first layer and the second layer are co-extruded.

8. The package according to any one of the preceding paragraphs, wherein a portion of an outer surface of the package material comprises a heat sealable lacquer, adhesive, and/or polymer.

9. The package according to any one of paragraphs 4-8, wherein the first and second layers are 20 weight percent or less of the package material.

10. The package according to any one of paragraphs 4-8, wherein the first and second layers are 10 weight percent or less, 5 weight percent or less, 4 weight percent or less, or 3 weight percent or less, but at least 1 weight percent of the package material.

11. The package according to any one of the preceding paragraphs, wherein the package exhibits a recyclable paper percentage of at least 80 percent.

12. The package according to any one of the preceding paragraphs, wherein the package exhibits a recyclable paper percentage of between about 60 percent to about 99.9 percent.

13. The package according to any one of the preceding paragraphs, wherein the package material comprises at least 50 percent by weight of the natural fibers.

14. The package according to any one of the preceding paragraphs, wherein the package material comprises about 70 percent to about 99 percent by weight of the natural fibers.

15. The package according to any one of the preceding paragraphs, wherein the natural fibers comprise wood fibers or pulp fibers.

16. The package according to any one of the preceding paragraphs, wherein the package material exhibits a HuBa value of about 5.3 hours to about 12 hours, according to the HuBa Test.

17. The package according to any one of the preceding paragraphs, wherein the package is substantially free of adhesive.

18. The package according to any one of the preceding paragraphs, wherein the one or more absorbent articles within the package comprise taped diapers, pants, or adult incontinence products.

19. The package according to any one of the preceding paragraphs, wherein the each of the one or more absorbent articles comprises a substantially unactivated wetness indicator.

20. The package according to any one of the preceding paragraphs, wherein the one or more absorbent articles comprise a breathable film as a backsheet component.

21. The package according to any one of the preceding paragraphs, wherein each of the one or more absorbent articles comprises superabsorbent polymers (SAP) in an amount of greater than about 5 grams per article.

22. The package according of any one of the preceding paragraphs, wherein the plurality of panels comprise the consumer-facing panel, a back panel, a left side panel, a right side panel, a bottom panel, a first top panel, and a second top panel.

23. The package of paragraph 22, wherein the consumer-facing panel, the back panel, the bottom panel, and the first and second top panels are formed of a continuous packaging material.

24. The package of paragraph 23, wherein the left side panel comprises a vertical left side seam and two angled left side seams, wherein the right panel comprises a vertical right side seam and two angled right side seams, wherein a length of the vertical left side seam is greater than a length of the two angled left side seams, and wherein a length of the vertical right side seam is greater than a length of the two angled right side seams.

25. The package of paragraph 24, wherein the consumer-facing panel has a consumer-facing panel height, and wherein the consumer-facing panel height is greater than the length of the vertical left side seam.

26. The package of paragraph 24, wherein the back panel has a back panel height, and wherein the back panel height is greater than the length of the vertical right side seam.

27. The package of paragraph 24, wherein the bottom panel is generally rectangular.

28. The package of paragraph 24, wherein the bottom panel, the consumer-facing panel, and the back panel are free of seams.

29. The package of any one of the preceding paragraphs, comprising a handle comprising a slit or slot therethrough, wherein the handle is integral with the package material.

30. The package according to paragraph 1, wherein the package material comprises a barrier layer comprising metalized paper disposed on an inner surface of the package material.

31. The package according to paragraph 1, wherein the package material comprises a barrier layer comprising an inorganic material disposed on an inner surface of the package material.

Aspect 4:

1. A package configured to receive one or more absorbent articles, the package comprising a package material;

wherein the package material comprises natural fibers, wherein the package comprises a plurality of panels comprising a consumer-facing panel and a back panel having one or more wicket holes in a portion thereof, wherein the package is configured to be sealed such that the one or more absorbent articles are enclosed therein;

wherein the back panel comprises a first chamfered side edge and a second chamfered side edge in an area proximate to the one or more wicket holes; and wherein the package is recyclable.

2. The package according to paragraph 1, wherein one or more slits or lines or perforation extend outwardly from the one or more wicket holes.

3. The package of paragraph 1 or 2, comprising a handle having a cut or perforated slit or slot therethrough, wherein the handle is integral with the package material.

4. The package according to any one of the preceding paragraphs, wherein the package material comprises a barrier film layer disposed on an inner surface of the package material.

5. The package according to paragraph 4, wherein the barrier film layer comprises low density polyethylene.

6. The package according to paragraph 4, wherein the barrier film layer comprises a first layer and a second layer, wherein the first layer comprises a first polyolefin material in contact the natural fibers, wherein the second layer comprises a second polyolefin material, wherein the first polyolefin material is different than the second polyolefin material, and wherein the second layer is in contact with the first layer.

7. The package of paragraph 6, wherein the second layer only overlaps about 5% to about 25% of the second layer 8. The package of paragraph 6, wherein the first layer comprises high-density polyethylene.

9. The package according to paragraph 8, wherein the second layer comprises low-density polyethylene.

10. The package according to any one of the preceding paragraphs, wherein a portion of an outer surface of the package material comprises a heat sealable lacquer, adhesive, and/or polymer.

11. The package according to any one of the preceding paragraphs, wherein the package comprises a vertical side seal having a side seal strength, and wherein the side seal strength is greater than about 5.1 N/15 mm to about 15 N/15 mm, according to Seal Tensile Strength Test.

12. The package according to any one of paragraphs 6-11, wherein the first and second layers are 10 weight percent or less, 5 weight percent or less, 4 weight percent or less, or 3 weight percent or less, but at least 1 weight percent of the package material.

13. The package according to any one of the preceding paragraphs, wherein the package exhibits a recyclable paper percentage of at least 80 percent.

14. The package according to any one of the preceding paragraphs, wherein the package exhibits a recyclable paper percentage of between about 60 percent to about 99.9 percent.

15. The package according to any one of the preceding paragraphs, wherein the package material comprises about 70 percent to about 99 percent by weight of the natural fibers.

16. The package according to any one of the preceding paragraphs, wherein the natural fibers comprise wood fibers or pulp fibers.

17. The package according to any one of the preceding paragraphs, wherein the package is substantially free of adhesive.

18. The package according to any one of the preceding paragraphs, wherein the one or more absorbent articles within the package comprise taped diapers, pants, or adult incontinence products, and wherein each of the one or more absorbent articles comprise a substantially unactivated wetness indicator.

19. The package according of any one of the preceding paragraphs, wherein the plurality of panels comprise the consumer-facing panel, a back panel, a left side panel, a right side panel, a bottom panel, a first top panel, and a second top panel.

20. The package of paragraph 19, wherein the consumer-facing panel, the back panel, the bottom panel, and the first and second top panels are formed of a continuous packaging material.

21. The package of paragraph 19, wherein the left side panel comprises a vertical left side seam and two angled left side seams, wherein the right panel comprises a vertical right side seam and two angled right side seams, wherein a length of the vertical left side seam is greater than a length of the two angled left side seams, and wherein a length of the vertical right side seam is greater than a length of the two angled right side seams.

22. The package of paragraph 19, wherein the consumer-facing panel has a consumer-facing panel height, and wherein the consumer-facing panel height is greater than the length of the vertical left side seam.

23. The package of paragraph 19, wherein the back panel has a back panel height, and wherein the back panel height is greater than the length of the vertical right side seam.

24. The package of paragraph 19, wherein the bottom panel is generally rectangular.

25. The package of paragraph 19, wherein the bottom panel, the consumer-facing panel, and the back panel are free of seams.

26. The package according to any one of paragraphs 1-3, wherein the package material comprises a barrier layer comprising metalized paper disposed on an inner surface of the package material.

27. The package according to any one of paragraphs 1-3, wherein the package material comprises a barrier layer comprising an inorganic material disposed on an inner surface of the package material.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." When ranges are disclosed herein, all numbers within those ranges are specifically recited herein but not written out for brevity. For example, if a range is 1 mm to 10 mm, 1 mm, 2 mm, 3 mm, 4 mm, 5 mm, 6 mm, 7 mm, 8 mm, 9 mm, and 10 mm are specifically recited. Also specifically recited herein are any ranges formed within the ranges, such as 3 mm to 7 mm, or 4 mm to 9 mm, for example. If a range of 1 mm to 10 mm and a range of 20 mm to 40 mm are provided, ranges formed between the two ranges are specifically recited, such as 1 mm to 40 mm or 10 mm to 20 mm, for example.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package of one or more absorbent articles, the package comprising a package material, wherein the package material comprises natural fibers, wherein the package comprises a plurality of panels comprising a first panel, wherein the package is sealed such that the one or more absorbent articles are enclosed therein;

wherein the package material exhibits a HuBa value of greater than about 5 hours, according to HuBa Test;

wherein the package is recyclable;

the package comprising a vertical side seal having a side seal strength, wherein the side seal strength is greater than about 5.1 N/15 mm to about 15 N/15 mm, according to the Seal Tensile Strength Test;

wherein the package material comprises a barrier film;

wherein the barrier film comprises a first layer most proximate to the natural fibers and a second layer most distal from the natural fibers;

wherein the first layer comprises a first polymer material;

wherein the second layer comprises a second polymer material;

wherein the first polymer material is different than the second polymer material;

wherein the first layer comprises high-density polyethylene;

wherein the second layer comprises low-density polyethylene;

wherein the first layer is in contact with the second layer; and wherein the first layer and second layer are co-extruded.

2. The package of claim 1, wherein a portion of an outer surface of the package material comprises a heat sealable lacquer, adhesive, and/or polymer.

3. The package of claim 1, wherein the first and second layers are 20 weight percent or less, 10 weight percent or less, 5 weight percent or less, 4 weight percent or less, or 3 weight percent or less, but at least 1 weight percent of the package material.

4. The package of claim 3, wherein each of the one or more absorbent articles comprise superabsorbent polymers (SAP) in an amount of greater than about 5 grams.

5. The package of claim 1, wherein the package exhibits a recyclable paper percentage of between about 60 percent to about 99.9 percent, or at least about 80%.

6. The package of claim 1, wherein the package material comprises about 70 percent to about 99 percent by weight of the natural fibers, and wherein the natural fibers comprise wood fibers or pulp fibers.

7. The package of claim 1, wherein the package material exhibits a HuBa value of about 5 hours to about 20 hours, about 5.3 hours to about 15 hours, or about 5.3 hours to about 12 hours, according to the HuBa Test.

8. The package of claim 1, wherein the package is substantially free of adhesive.

9. The package of claim 1, wherein the one or more absorbent articles within the package comprise taped diapers, pants, or adult incontinence products.

10. The package of claim 1, wherein one or more absorbent articles comprise a substantially unactivated wetness indicator, and wherein the one or more absorbent articles comprise a breathable film as a backsheet component.

11. The package of claim 1, wherein the plurality of panels comprise the first panel, a back panel, a left side panel, a right side panel, a bottom panel, a first top panel, and a second top panel.

12. The package of claim 11, wherein the first panel, the back panel, the bottom panel, and the first and second top panels are formed of a continuous packaging material.

13. The package of claim 12, wherein the left side panel comprises a vertical left side seam and two angled left side seams, wherein the right panel comprises a vertical right side seam and two angled right side seams, wherein a length of the vertical left side seam is greater than a length of the two angled left side seams, and wherein a length of the vertical right side seam is greater than a length of the two angled right side seams.

14. The package of claim 13, wherein the first panel has a first panel height, and wherein the first panel height is greater than the length of the vertical left side seam.

15. The package of claim 14, wherein the back panel has a back panel height, wherein the back panel height is greater than the length of the vertical right side seam, wherein the bottom panel, the first panel, and the back panel are free of seams, and wherein the bottom panel is generally rectangular.

16. The package of claim 1, wherein the high-density polyethylene and/or the low-density polyethylene comprises PIR and/or PCR.

17. The package of claim 1, comprising a handle having a cut or perforated slit or slot therethrough, wherein the handle is integral with the package material.

18. A package of one or more absorbent articles, the package comprising a package material, wherein the package material comprises natural fibers, wherein the package comprises a plurality of panels comprising a first panel, wherein the package is sealed such that the one or more absorbent articles are enclosed therein;

wherein the package material exhibits a HuBa value of greater than about 5 hours, according to HuBa Test;

wherein the package is recyclable;

the package comprising a vertical side seal having a side seal strength, wherein the side seal strength is greater than about 5.1 N/15 mm to about 15 N/15 mm, according to the Seal Tensile Strength Test;

wherein the package material comprises a barrier film;

wherein the barrier film comprises a first layer most proximate to the natural fibers and a second layer most distal from the natural fibers;

wherein the first layer comprises high-density polyethylene;

wherein the second layer comprises low-density polyethylene;

wherein the first layer is in contact with the second layer.

* * * * *